US008828668B2

(12) United States Patent
Axtell et al.

(10) Patent No.: US 8,828,668 B2
(45) Date of Patent: Sep. 9, 2014

(54) MARKERS FOR DETERMINATION OF PATIENT RESPONSIVENESS

(75) Inventors: Robert C. Axtell, Menlo Park, CA (US); Lawrence Steinman, Stanford, CA (US); May H. Han, Menlo Park, CA (US); Brigit A. de Jong, Nijmegen (NL); Chander Raman, Birmingham, AL (US); Michael Walker, Carlsbad, CA (US); Jing Shi, Carlsbad, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 40 days.

(21) Appl. No.: 13/026,173

(22) Filed: Feb. 11, 2011

(65) Prior Publication Data

US 2011/0243893 A1   Oct. 6, 2011

Related U.S. Application Data

(60) Provisional application No. 61/303,590, filed on Feb. 11, 2010, provisional application No. 61/315,743, filed on Mar. 19, 2010, provisional application No. 61/401,045, filed on Aug. 6, 2010, provisional application No. 61/402,757, filed on Sep. 2, 2010.

(51) Int. Cl.
*G01N 33/53* (2006.01)
*A61K 39/395* (2006.01)
*A61K 38/00* (2006.01)

(52) U.S. Cl.
USPC ...... 435/7.1; 530/387.1; 514/21.2; 424/146.1

(58) Field of Classification Search
CPC .................. G01N 2800/285; G01N 33/6863; G01N 2800/60; G06F 19/3443; G06F 19/345
See application file for complete search history.

(56) References Cited

U.S. PATENT DOCUMENTS

| | | | |
|---|---|---|---|
| 6,849,719 | B2 | 2/2005 | Shi et al. |
| 2005/0186245 | A1 | 8/2005 | Hunter et al. |
| 2006/0094056 | A1 | 5/2006 | Chappell et al. |
| 2007/0269428 | A1 | 11/2007 | Christie et al. |
| 2008/0227847 | A1 | 9/2008 | Nilsson et al. |
| 2008/0248025 | A1 | 10/2008 | Roark et al. |
| 2008/0292641 | A1 | 11/2008 | Sass et al. |
| 2009/0171590 | A1 | 7/2009 | Puskas et al. |
| 2009/0208481 | A1 | 8/2009 | Steinman et al. |
| 2010/0021456 | A1 | 1/2010 | Miossec et al. |

OTHER PUBLICATIONS

Bushnell S.E. et al. Neurology 79 Aug. 7, 2012, pp. 531-537.*
Cobb J.P. et al. Crit Care Med 2002 vol. 30, No. 12, pp. 2711-2721.*
Hoshikawa Y. et al. Physiol Genomics (2003) 12: 209-219.*
The Area Under and ROC Curve, from http://gim.unmc.edu/dxtests/roc3.htm, printed on Sep. 17, 2012, pp. 1-2.*
Dhib-Jalbut S. et al. Journal of Neuroimmunology 254 (2013) pp. 131-140.*
Steinman L. et al. Multiple Sclerosis Journal 19(1) (2012) pp. 5-14.*
Boniface K. et al. The Journal of Immunology Jul. 1, 2010, vol. 185 No. 1, 679-687.*
Arnason, "Immunologic therapy of multiple sclerosis", Annu Rev Med (1999), 50:291-302.
Awasthi; et al., "A dominant function for interleukin 27 in generating interleukin 10-producing anti-inflammatory T cells", Nat Immunol (2007), 8:1380-9.
Baker; et al., "Cytokines in the central nervous system of mice during chronic relapsing experimental allergic encephalomyelitis", Cell Immunol (1991), 134:505-10.
Berenson; et al., "Distinct characteristics of murine STAT4 activation in response to IL-12 and IFN-alpha". J Immunol (2006), 177:5195-203.
Bartosik-Psujek; et al., "The interleukin-10 levels as a potential indicator of positive response to interferon beta treatment of multiple sclerosis patients", Clin Neurol Neurosurg (2006), 108:644-7.
BD Pharmingen, "HumanTh1/Th17 Phenotyping Kit", Technical Data Sheet (2008), pp. 1-4.
Benveniste; et al., "Type I interferons as anti-inflammatory mediators", Sci STKE (2007), 416:pe70, pp. 1-4.
Bettellii; et al., "Reciprocal developmental pathways for the generation of pathogenic effector TH17 and regulatory T cells", Nature (2006), 441:235-8.
Eisen; et al., "Cluster analysis and display of genome-wide expression patterns", PNAS (1998), 95:14863-8.
Ferber; et al., "Mice with a disrupted IFN-gamma gene are susceptible to the induction of experimental autoimmune encephalomyelitis (EAE)", J Immunol (1996), 156:5-7.
Francisco; et al., "Beta interferon restricts the inflammatory potential of CD4+ cells through the boost of the Th2 phenotype, the inhibition of Th17 response and the prevalence of naturally occurring T regulatory cells", Molecular Immunology (2008), 45:4008-4019.
Graber; et al., "Cytokine changes during interferon-beta therapy in multiple sclerosis: correlations with interferon dose and MRI response", J Neuroimmunol (2007), 185:168-74.

(Continued)

*Primary Examiner* — Stephen Kapushoc
(74) *Attorney, Agent, or Firm* — Bozicevic, Field & Francis LLP; Pamela J. Sherwood; Kyle A. Gurley

(57) ABSTRACT

Compositions and methods are provided for prognostic classification of inflammatory diseases, e.g. inflammatory demyelinating disease, patients into subtypes, which subtypes are informative of the patient's need for therapy and responsiveness to a therapy of interest. The patterns of cytokines provides for a signature pattern that can identify patients likely to benefit from therapeutic intervention as well as discriminate patients that have a high probability of responsiveness to a therapy from those that have a low probability of responsiveness. Assessment of this signature pattern thus allows improved methods of care. In one embodiment of the invention, the autoimmune disease is multiple sclerosis or neuromyelitis optica.

19 Claims, 25 Drawing Sheets

(56) References Cited

OTHER PUBLICATIONS

Guo, B; et al., "The type I IFN induction pathway constrains Th17-mediated autoimmune inflammation in mice", J Clin Invest (2008), 118(5):1680-1690.
Haak; et al., "IL-17A and IL-17F do not contribute vitally to autoimmune neuro-inflammation in mice", J Clin Invest (2009), 119:61-9.
Harrington; et al., "Interleukin 17-producing CD4(+) effector T cells develop via a lineage distinct from the T helper type 1 and 2 lineages", Nat Immunol (2005), 6(11):1123-1132.
Hengstman; et al., "Neuromyelitis optica with clinical and histopathological involvement of the brain", Mult Scler (2007), 13:679-82.
Ishizu; et al., "Intrathecal activation of the IL-17/IL-8 axis in opticospinal multiple sclerosis", Brain (2005), 128:988-1002.
Ke; et al., "Anti-inflammatory role of IL-17 in experimental autoimmune uveitis", J Immunol (2009), 182:3183-90.
Komiyama; et al., "IL-17 plays an important role in the development of experimental autoimmune encephalomyelitis", J Immunol (2006), 177:566-73.
Kroenke; et al., "IL-12- and IL-23-modulated T cells induce distinct types of EAE based on histology, CNS chemokine profile, and response to cytokine inhibition", J Exp Med (2008), 205:1535-41.
Langrish;et al., "IL-23 drives a pathogenic T cell population that induces autoimmune inflammation", J Exp Med (2005), 201:233-40.
Liang; et al., "An IL-17F/A heterodimer protein is produced by mouse Th17 cells and induces airway neutrophi recruitment", J Immunol (2007), 179:7791-9.
Lucchinetti; et al., "A role for humoral mechanisms in the pathogenesis of Devic's neuromyelitis optica", Brain (2002), 125:1450-61.
Mangan; et al., "Transforming growth factor-beta induces development of the T(H)17 lineage", Nature (2006), 441:231-4.
McGeachy;et al., "TGF-beta and IL-6 drive the production of IL-17 and IL-10 by T cells and restrain T(H)-17 cell-mediated pathology", Nat Immunol (2007), 8:1390-7.
McGeachy; et al., "The interleukin 23 receptor is essential for the terminal differentiation of interleukin 17-producing effector T helper cells in vivo", Nat Immunol (2009), 10(3):314-324.
McRae; et al., "Type I IFNs inhibit human dendritic cell IL-12 production and Th1 cell development", J Immunol (1998), 160:4298-304.
Nagai; et al., "Interferon-beta mediates opposing effects on interferon-gamma-dependent Interleukin-12 p70 secretion by human monocyte-derived dendritic cells", Scand J Immunol (2007), 65:107-17.
Nguyen; et al., "Interferon alpha/beta-mediated inhibition and promotion of interferon gamma: STAT1 resolves a paradox", Nat Immunol (2000), 1:70-6.
Panitch; et al., "Treatment of multiple sclerosis with gamma interferon: exacerbations associated with activation of the immune system", Neurology (1987), 37:1097-102.
Parronchi; et al., "IL-4 and IFN (alpha and gamma) exert opposite regulatory effects on the development of cytolytic potential by Th1 or Th2 human T cell clones", J Immunol (1992), 149:2977-83.
Perona-Wright; et al., "IL-10 permits transient activation of dendritic cells to tolerize T cells and protect from central nervous system autoimmune disease", Int Immunol (2007), 19:1123-34.
Pestka; et al., "Interleukin-10 and related cytokines and receptors", Annu Rev Immunol (2004), 22:929-79.
Platanias, "Mechanisms of type-I- and type-II-interferon-mediated signalling", Nat Rev Immunol (2005), 5:375-86.
Prinz; et al., "Distinct and Nonredundant In Vivo Functions of IFNAR on Myeloid Cells Limit Autoimmunity in the Central Nervous System", Immunity (2008), 28:675-686.
Shimizu;et al., "Development of extensive brain lesions following interferon beta therapy in relapsing neuromyelitis optica and longitudinally extensive myelitis", J Neurol (2008), 255:305-7.
Smith; et al., "IL-23 is required for neutrophil homeostasis in normal and neutrophilic mice", J Immunol (2007),179:8274-9.
Steinman, "A rush to judgment on Th17", J Exp Med (2008), 205:1517-22.
Stromnes; et al., "Differential regulation of central nervous system autoimmunity by T(H)1 and T(H)17 cells", Nat Med (2008), 14:337-42.
Tanabe; et al., "Cutting edge: role of STAT1, STAT3, and STAT5 in IFN-alpha beta responses in T lymphocytes", J Immunol (2005), 174:609-13.
Veldhoen; et al., "TGFbeta in the context of an inflammatory cytokine milieu supports de novo differentiation of IL-17-producing T cells", Immunity (2006), 24:179-89.
Wang; et al., "Early relapse in multiple sclerosis-associated optic neuritis following the use of interferon beta-1a in Chinese patients", Jpn J Ophthalmol (2006), 50:537-42.
Warabi; et al., "Interferon beta-1b exacerbates multiple sclerosis with severe optic nerve and spinal cord demyelination", J Neurol Sci (2007), 252:57-61.
Wensky; et al., "IFN-gamma determines distinct clinical outcomes in autoimmune encephalomyelitis", J Immunol (2005), 174:1416-23.
Willenborg; et al., "IFN-gamma plays a critical down-regulatory role in the induction and effector phase of myelin oligodendrocyte glycoprotein-induced autoimmune encephalomyelitis", J Immunol (1996), 157:3223-7.
Wong; et al., "IFN-gamma priming up-regulates IFN-stimulated gene factor 3 (ISGF3) components, augmenting responsiveness of IFN-resistant melanoma cells to type I IFNs", J Immunol (1998), 160:5475-84.
Yang; et al., "Regulation of inflammatory responses by IL-17F", J Exp Med (2008), 205:1063-75.
Zhang; et al., "Interleukin-17 causes neutrophil mediated inflammation in ovalbumin-induced uveitis in DO11.10 mice", Cytokine (2009), 46:79-91.
Zhou; et al. "IL-6 programs T(H)-17 cell differentiation by promoting sequential engagement of the IL-21 and IL-23 pathways", Nat Immunol (2007), 8:967-74.
Martin-Saavedra; et al. "Beta interferon restricts the inflammatory potential of CD4+ cells through the boost of the Th2 phenotype, the inhibition of Th17 response and the prevalence of naturally occurring T regulatory cells", Mol Immunol (Sep. 2008), 45(15):4008-4019.
Argyriou; et al. "Neuromyelitis optica: a distinct demyelinating disease of the central nervous system", Acta Neurol Scand (2008),118:209-217.
Jacob; et al. "Treatment of Neuromyelitis Optica With Mycophenolate Mofetil", Arch Neurol (Sep. 2009), 66 (9):1128-1133.
Misumi; et al. "Effects of sivelestat, a new elastase inhibitor, on IL-8 and MCP-1 production from stimulated human alveolar epithelial type II cells", J Anesth (Jan. 2006),20:159-165.

\* cited by examiner

A

B

C

MARKERS FOR DETERMINATION OF PATIENT RESPONSIVENESS

BACKGROUND

There is a long-standing interest in manipulating cells of the immune system to achieve control of autoimmune disease. While targeted antigen-specific therapy remains of great interest, there has also been considerable development of polyclonal, or non-antigen specific therapies. In addition to general immunosuppression, e.g. through the use of agents such as hydrocortisone, many therapies are now being brought to the clinic that provide for a more selective modification of the immune system, such as modulation of cytokines.

Cytokines are messenger molecules produced by B cells, T cells, macrophages, dendritic cells and other immune and host cells. Cytokines play roles in the pathogenesis of rheumatoid arthritis, multiple sclerosis and other autoimmune diseases. Cytokines and related messenger molecules include chemokines, interleukins, lymphokines, growth factors, angiogenesis factors, and other secreted and cell surface molecules that transmit signals to other cells. Blockade of several of these with biological agents have already provided therapeutic benefit in certain autoimmune diseases, while other conditions have responded to increasing cytokine activity.

Multiple sclerosis (MS) is the most common autoimmune illness of the central nervous system. For many years the inflammatory manifestations of MS were treated using only corticosteroids. However, more recently the results of clinical trials with immunomodulatory agents have changed the therapeutic approach to this disease. Interferon beta (IFNβ)-1b represents the pioneer of those therapies. There is growing evidence from clinical trials on relapsing-remitting MS and clinically isolated syndromes suggestive of MS that IFNβ-1b reduces the frequency and severity of relapses and the development of new and active brain lesions. There can be a significant benefit to treatment early in the disease, for example as shown by the Betaferon/Betaseron in Newly Emerging Multiple Sclerosis For Initial Treatment (BENEFIT) study. Irreversible axonal damage can begin early in the course of MS, and immunomodulatory treatment of MS can have a greater effect early in the disease course.

A downside to this promising therapy is the diversity of responses in patient populations. While a significant proportion of patients can respond to a particular therapy, many do not. The clinician can therefore need to prescribe sequential expensive and time-consuming therapies in order to determine which is effective for the individual patient. Furthermore, it has been reported that IFN-β can exacerbate symptoms in some individuals.

The use of disease-modifying therapies in autoimmune conditions is of great clinical interest; however these therapies suffer from the inability to determine a priori which patients will benefit. The present invention addresses this need.

Publications of interest include Guo et al. *J Clin Invest* (2008); Nagai et al. *Scand J Immunol* 65, 107-17 (2007); McRae et al. *J Immunol* 160, 4298-304 (1998); Martin-Saavedra et al. *Mol Immunol* 45, 4008-19 (2008).

SUMMARY

Compositions and methods are provided for prognostic classification of individuals into groups that are informative of the individual's responsiveness to a therapy of interest. In particular, it is shown that the efficacy of immunomodulatory treatments of inflammatory diseases having a TH17 involvement, including without limitation inflammatory demyelinating diseases, for example those of the central nervous system, e.g. multiple sclerosis, neuromyelitis optica, EAE, etc., depends on whether a patient has a predominantly TH1-type disease subtype, or a predominantly TH17-type disease subtype. Patients can be classified into subtypes by determining the levels of markers, including IL-17; endogenous β-interferon, IL-23, PDGFBB, sFAS ligand, M-CSF, MIP1a, TNF-B, IFNa, IL-1RA, MCP-1, IL-2, IL-6, IL-8, FGFb, IL-7, TGF-β, IFNβ, IL-13, IL-17F, EOTAXIN, IL-1a, MCP-3, LIF, NGF, RANTES, IL-5, MIP1b, IL-12p70, and HGF, etc. Quantitation of IL-17F is of particular interest, and in some embodiments can be compared to levels of IL-17A. Quantitation of IL-7 is also of particular interest. Determination of these cytokine levels distinguishes individuals who have a high probability of responsiveness to a therapy from those who have a low probability of responsiveness to a therapy of interest. Therapies of interest can include without limitation, alpha-interferons, beta-interferons, cytokines, cytokine antagonists, NSAIDs, statins, immunosuppressive drugs, and the like.

Assessment in a patient allows improved care, where patients classified according to responsiveness can be treated with an appropriate agent. For example, in the treatment of inflammatory central nervous system disorders, β-IFN and similar drugs can be advised or provided for patients with a TH1-type disease subtype, while patients classified as a predominantly TH17-type disease subtype can be treated with appropriate agents, e.g. IL-17 inhibitors, e.g. IL-17F inhibitors, IL-23 inhibitors, copaxone, statins, γ-IFN, etc. Patients can be classified upon initial presentation of symptoms, and can be further monitored for status over the course of the disease to maintain appropriate therapy, or can be classified at any appropriate stage of disease progression.

In one embodiment of the invention, a method is provided for determining which immunomodulatory treatment a patient, e.g. an MS patient, will be responsive/non-responsive to, the method comprising determining levels of at least one marker in the patient, where the marker(s) is indicative of the TH1/TH17 status of the patient. A patient having high levels of markers indicative of a TH17 subtype, e.g. IL-17F, IL-23, β-IFN, etc. is classified as non-responder to TH1 subtype immunotherapy, which therapies include without limitation, administration of β-IFN. Such patients can be treated with alternative therapies as described above. Based on the classification, appropriate therapy is provided.

Methods of determining responder status in a patient with an inflammatory disease having a TH17 involvement can comprise obtaining or preparing a cytokine measurement panel comprising one or more affinity reagents specific for markers, including for example, anti-IL-17, e.g. IL-17F, IL-7, β-IFN, etc.; physically contacting the panel with a patient sample such as blood, serum, cerebrospinal fluid, etc.; identifying the markers that bind to the panel; comparing the markers bound to the those bound with a control sample known to be one or more of: a non-diseased individual, an individual known to have a responder or non-responder phenotype, etc. Those patients non-responsive to TH1-therapy, such as β-IFN, can be characterized has having a level of IL-17, e.g. IL-17F, that is significantly higher than a non-diseased individual, while those patients responsive to such therapy have a level of IL-17 not significantly different than a non-diseased individual. The resulting data set provides a signature pattern from which the prognostic classification can be determined.

Quantitation of IL-7 is also of particular interest. Those patients responsive to TH1-therapy, such as β-IFN, can be characterized has having a level of IL-7, that is significantly higher than a non-diseased individual, while those patients non-responsive to such therapy have a level of IL-7 not significantly different than a non-diseased individual. The resulting data set provides a signature pattern from which the prognostic classification can be determined.

In other embodiments of the invention, methods of treating inflammatory diseases having a TH17 involvement are provided. Patients categorized as a non-responder to β-IFN can be treated with anti-IL17 as an alternative to β-IFN, where an effective dose or course of treatment of an IL-17, particularly IL-17F, inhibitor is administered to the patient. Alternatively such patients can be treated with anti-IL23 as an alternative to β-IFN, where an effective dose or course of treatment of an IL-23 inhibitor is administered to the patient. Alternatively various known therapies suitable for TH17 dominated disease can be administered, including copaxone, statins, and the like.

Patients suffering from neuromyelitis optica, which is shown herein to be an IL-17 type disease, can also be treated with an effective dose or course of treatment of an IL-17, particularly an IL-17F, inhibitor. Inhibitors include neutralizing antibodies specific for at least one IL-17, e.g. IL-17F or IL-23 protein, soluble IL-17, e.g. IL-17F, or IL-23 receptor; inactive forms of IL-17, e.g. IL-17F, or IL-23; and the like.

In other embodiments, the effectiveness of β-IFN in a patient classified as a non-responder is enhanced by administration of an effective dose of γ-IFN. The γ-IFN can be co-formulated with an effective dose of β-IFN, or can be administered as a single agent that complements endogenous β-IFN.

In other embodiments of the invention a device or kit is provided for the analysis of patient samples. Such devices or kits will include reagents that specifically identify one or more cytokines indicative of the TH1/TH17 status of the patient, e.g. IL-17, e.g. IL-17F, IL-7, IL-23, β-IFN, etc. Devices of interest include arrays, where the reagents are spatially separated on a substrate such as a slide, gel, multi-well plate, etc. Alternatively the reagents can be provided as a kit comprising reagents in a suspension or suspendable form, e.g. reagents bound to beads suitable for flow cytometry, and the like.

Also described herein is a method for assessing prognosis for responsiveness of a patient with an inflammatory disease having a TH17 involvement, e.g. an inflammatory demyelinating disease subject to a therapy of interest, comprising: obtaining a dataset associated with a sample obtained from the subject, wherein the dataset comprises quantitiative data for a marker selected from PDGFBB, sFAS ligand, M-CSF, MIP1a, TNF-B, IFNα, IL-1RA, MCP-1, IL-2, IL-6, IL-8, FGFb, IL-7, TGF-β, IFNβ, IL-13, IL-17F, EOTAXIN, IL-1a, MCP-3, LIF, NGF, RANTES, IL-5, MIP1b, IL-12p70, and HGF; and analyzing the dataset for the marker, wherein a statistically significant match with a responder pattern for the therapy of interest or a statistically significant difference from a non-responder pattern for the therapy of interest is indicative of the responsiveness of the subject to the therapy of interest.

In an embodiment, the dataset comprises quantitative data for at least two, three, four, five, six, seven, eight, nine, ten, eleven, twelve, thirteen, fourteen, fifteen, sixteen, seventeen, eighteen, nineteen, twenty or more markers selected from PDGFBB, sFAS ligand, M-CSF, MIP1a, TNF-B, IFNα, IL-1RA, MCP-1, IL-2, IL-6, IL-8, FGFb, IL-7, TGF-b, IFNβ, IL-13, IL-17F, EOTAXIN, IL-1a, MCP-3, LIF, NGF, RANTES, IL-5, MIP1b, IL-12p70, and HGF. In an embodiment, LIF, EOTAXIN, TGF-β, IL-13, and MCP-3 are associated with the responder pattern to a TH1-therapy; and IL-17F and IFNβ are associated with the responsiveness pattern to a TH1-therapy.

In an embodiment, the method is implemented on one or more computers.

In an embodiment, the method further comprises selecting a therapeutic regimen based on the analysis. In an embodiment, the method further comprises determining a treatment course for the subject based on the analysis.

In an embodiment, the data is obtained from a nucleotide-based assay or an antibody-based assay.

In an embodiment, the subject is a human subject.

In an embodiment, the method further comprises assessing a clinical factor in the mammalian subject; and combining the assessment with the analysis of the marker to the assessment of the prognosis for responsiveness of the subject to the therapy of interest.

Also described herein is a computer-implemented method for assessing prognosis for responsiveness of inflammatory diseases having a TH17 involvement, e.g. an inflammatory demyelinating disease subject to a therapy of interest, comprising: storing, in a storage memory, a dataset associated with a first sample obtained from the subject, wherein the dataset comprises data for a marker selected from PDGFBB, sFAS ligand, M-CSF, MIP1a, TNF-B, IFNα, IL-1RA, MCP-1, IL-2, IL-6, IL-8, FGFβ, IL-7, TGF-β, IFNβ, IL-13, IL-17F, EOTAXIN, IL-1a, MCP-3, LIF, NGF, RANTES, IL-5, MIP1b, IL-12p70, and HGF; and analyzing, by a computer processor, the dataset for the marker, wherein a statistically significant match with a responder pattern for the therapy of interest or a statistically significant difference from a non-responder pattern for the therapy of interest is indicative of the responsiveness of the subject to the therapy of interest.

Also described herein is a system for assessing responsiveness of an inflammatory diseases having a TH17 involvement, e.g. an inflammatory demyelinating disease subject to a therapy of interest, the system comprising: a storage memory for storing a dataset associated with a sample obtained from the subject, wherein the dataset comprises data for one or more markers selected from PDGFBB, sFAS ligand, M-CSF, MIP1a, TNF-B, IFNα, IL-1RA, MCP-1, IL-2, IL-6, IL-8, FGFβ, IL-7, TGF-β, IFNβ, IL-13, IL-17F, EOTAXIN, IL-1a, MCP-3, LIF, NGF, RANTES, IL-5, MIP1b, IL-12p70, and HGF; and a processor communicatively coupled to the storage memory for analyzing the dataset for the marker, wherein a statistically significant match with a responder pattern for the therapy of interest or a statistically significant difference from a non-responder pattern for the therapy of interest is indicative of the responsiveness of the subject to the therapy of interest.

Also described herein is a computer-readable storage medium storing computer-executable program code, the program code comprising: program code for storing a dataset associated with a sample obtained from a subject, wherein the dataset comprises data for one or more markers selected from PDGFBB, sFAS ligand, M-CSF, MIP1a, TNF-B, IFNα, IL-1RA, MCP-1, IL-2, IL-6, IL-8, FGFβ, IL-7, TGF-β, IFNβ, IL-13, IL-17F, EOTAXIN, IL-1a, MCP-3, LIF, NGF, RANTES, IL-5, MIP1b, IL-12p70, and HGF; and program code for analyzing the dataset for the marker, wherein a statistically significant match with a responder pattern for the therapy of interest or a statistically significant difference from a non-responder pattern for the therapy of interest is indicative of the responsiveness of the subject to the therapy of interest.

Also described herein is a kit for use in assessing responsiveness of an inflammatory diseases having a TH17 involvement, e.g. an inflammatory demyelinating disease subject to a therapy of interest, comprising: a set of reagents comprising a plurality of reagents for determining from a sample obtained from the subject data for one or more markers selected from PDGFBB, sFAS ligand, M-CSF, MIP1a, TNF-B, IFNα, IL-1RA, MCP-1, IL-2, IL-6, IL-8, FGFβ, IL-7, TGF-β, IFNβ, IL-13, IL-17F, EOTAXIN, IL-1a, MCP-3, LIF, NGF, RANTES, IL-5, MIP1b, IL-12p70, and HGF; instructions for using the plurality of reagents to determine data from the sample; and instuctions for statistically analyzing the data, wherein a statistically significant match with a responder pattern for the therapy of interest or a statistically significant difference from a non-responder pattern for the therapy of interest is indicative of the responsiveness of the subject to the therapy of interest.

In an embodiment, the instructions comprise instructions for conducting an antibody-based assay.

DETAILED DESCRIPTION

Figure 1:
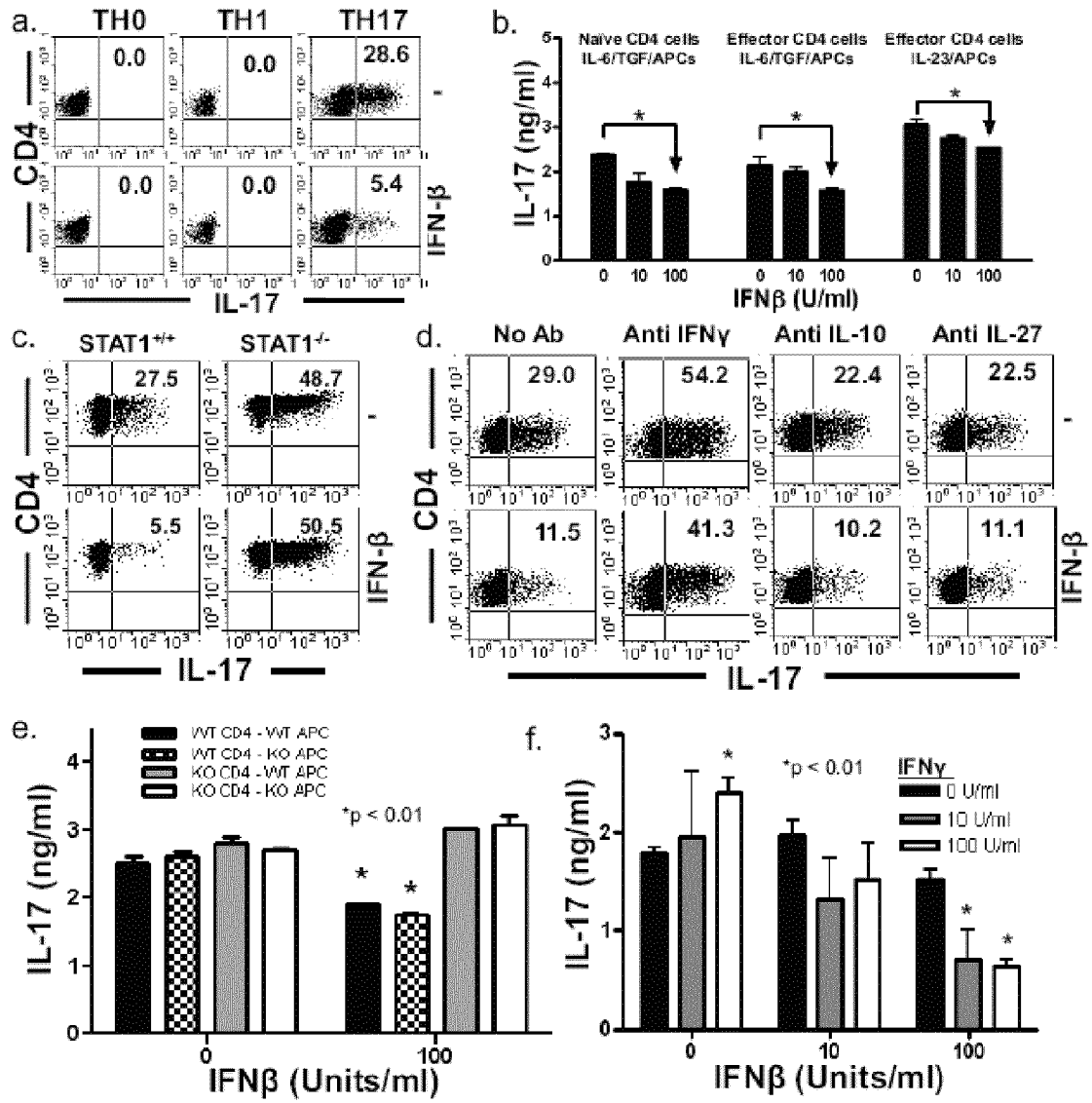
FIG. 1. Effect of IFN-β on murine TH17 differentiation. A) IFN-β inhibits TH17 differentiation. Spleen cells, depleted of CD8 T-cells, were cultured with and without IFN-β (100 U/ml) in TH0 (non-polarizing), TH1 (IL-12) and TH17 (TGFβ and IL-6) conditions. CD4 gated cells were analyzed for IL-17 production by flow cytometry. B) IFN-β inhibits early and late TH17 differentiation. Effect of IFN-β stimulation of naïve CD4 T-cells (CD62$^+$) cultured in TGF-β and IL-6 with APCs, effector/memory CD4 T-cell (CD62$^-$) cultured in TGF-β and IL-6 with APCs and effector/memory CD4 T-cell (CD62$^-$) cultured in IL-23 and APCs. All CD4 cells were cultured with APCs at a ratio of 1:5. Cytokine secretion was analyzed by ELISA. Results are the mean±SD of triplicates. Results are a representative of 3 similar experiments. C. IFN-β requires STAT1 to inhibit TH17 differentiation. STAT1$^{-/-}$ spleen cells, depleted of CD8 T-cells, were cultured with and without IFN-β (100 U/ml) in TH17 conditions. IL-17 production from CD4 gated T-cells was analyzed by flow cytometry. D) IFN-β requires IFN-γ but not IL-10 or IL-27 to inhibit TH17 differentiation. CD8-depleted spleen cells from C57BL/6 mice were cultured in TH17 conditions with or without IFN-β in the presence and absence of neutralizing antibodies to IFN-γ, IL-10 or IL-27p28. E) IFN-β requires IFN-γ signaling in CD4 T-cells and APCs to inhibit TH17 differentiation. Purified WT or IFNγR$^{-/-}$ CD4 T-cells were polarized in TH17 polarizing conditions with WT or IFNγR$^{-/-}$ in the presence or absence of IFN-β and IL-17 production was assessed by ELISA. F) IFN-β with IFN-γ directly inhibits TH17 differentiation. Purified CD4 T-cells were stimulated with plate-bound anti-CD3 and anti-CD28 in TH17 polarizing conditions in the presence or absence of IFN-β, IFN-γ or both; IL-17 production was assessed by ELISA. Results are the mean±SD of triplicates. Results are a representative of 3 similar experiments.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

It must be noted that, as used in the specification and the appended claims, the singular forms "a," "an," and "the" include plural referents unless the context clearly dictates otherwise.

Compositions and methods are provided for prognostic classification of patients having an inflammatory diseases with a TH17 involvement according to their ability to respond to specific immunomodulatory therapies using marker signature patterns. Marker signature pattern as used herein refers to the spectrum of biomarker levels, which frequently are serum levels of biomarkers, including without limitation cytokine biomarkers. Once the marker levels and pattern for a particular sample are identified, the data is used in selecting the most appropriate therapy for an individual. By analysis of marker levels on an individual basis, the specific subclass of disease is determined, and the patient can be classified based on the likelihood to respond to treatments of interest, including treatment with interferons, cytokines, cytokine antagonists, cytokine mimetics and bioequivalents, steroids, NDAIDs, statins, and the like, including β-IFN, anti-IL-17, particularly IL-17F, anti-IL-23, γ-IFN, etc. Thus, the marker signature can provide prognostic information to guide clinical decision making, both in terms of institution of and escalation of therapy as well as in the selection of the therapeutic agent to which the patient is most likely to exhibit a robust response.

Many, if not most, autoimmune and inflammatory diseases involve multiple types of T cells, e.g. TH1, TH2, TH17, and the like. As exemplified herein by analysis of response of patient groups to β-IFN; there is a differential efficacy for treatment of different inflammatory diseases having a TH17 involvement; and even in patients with the same disease. Surprisingly, it is shown herein (see Example 1) that the classification of such disease, exemplified without limitation by MS and neuromyelitis optica, according to the predominant T cell type provides a prognostic marker for responsiveness to different classes of therapeutic agents. For example, patients having a predominantly TH17 subtype can surprisingly worsen when treated with β-IFN. Biomarkers that would result from, or are associated with, different underlying T cell and T cell-related mechanisms are provided herein, which biomarkers are useful in providing a prediction of responsiveness.

The information obtained from the marker profile is used to (a) determine type and level of therapeutic intervention warranted (i.e. more versus less aggressive therapy, monotherapy versus combination therapy, type of combination therapy)), and (b) to optimize the selection of therapeutic agents. With this approach, therapeutic regimens can be individualized and tailored according to the specificity data obtained at different times over the course of treatment, thereby providing a regimen that is individually appropriate. In addition, patient samples can be obtained at any point during the treatment process for analysis.

Mammalian species that provide samples for analysis include canines; felines; equines; bovines; ovines; etc. and primates, particularly humans. Animal models, particularly small mammals, e.g. murine, lagomorpha, etc. can be used for experimental investigations. Animal models of interest include those for models of autoimmunity, graft rejection, and the like.

Inflammatory Disease.

Inflammation is a process whereby the immune system responds to infection or tissue damage. Inflammatory disease results from an activation of the immune system that causes illness, in the absence of infection or tissue damage, or at a response level that causes illness. Inflammatory disease includes autoimmune disease, which are any disease caused by immunity that becomes misdirected at healthy cells and/or tissues of the body. Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease. Autoimmune diseases include diseases that affect specific tissues as well as diseases that can affect multiple tissues, which can depend, in part on whether the responses are directed to an antigen confined to a particular tissue or to an antigen that is widely distributed in the body.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity). A cell critical in mediating and regulating these effector functions are CD4+ T cells, which can be subtyped as TH1, TH2, TH17, etc.

Th17 cells constitute a subset of effector T helper cells with distinct effector functions. Th17 cells were established as an independent subset of T helper cells by the identification of differentiation factors and transcription factors that are unique to Th17 cells (see Steinman (2008) JEM 205(7):1517-1522; and Korn et al. (2009) Ann. Rev. Imunol. 27:485-517). TH-17 cells are identified as those T cells with a cytokine 'signature' encompassing IL-17A, IL-17F, IL-22 and IL-26. One of skill in the art can readily classify a T cell based on patterns of cytokine expression, for example where one or more of IL-17A, IL-17F, IL-22 and IL-26 are upregulated relative to the levels associated with a TH1 or TH2 T cell. Th17 cells can be potent inducers of tissue inflammation and have been associated with the pathogenesis of many experimental autoimmune diseases and human inflammatory conditions. Many TH-17 cells also express the signature TH1 cytokine, interferon γ (IFN-γ).

The differentiation factors (TGF-β plus IL-6 or IL-21) and specific transcription factors (STAT3, IRF4, RORγt, and RORα) that define the Th17 transcriptional program have been identified. Differentiation of Th17 cells is driven by the simultaneous presence of transforming growth factor-beta and certain inflammatory cytokines (e.g. IL-6, IL-21), and recent studies have shown that inflammation instigated by IL-17-producing cells is central to the development and pathogenesis of several human autoimmune diseases and animal models of autoimmunity. It is the elaboration of specific cytokines from such T cells that appears to be the major mechanism by which T cells mediate their functions. Thus, characterizing the types of cytokines and the types of T cells present in a particular disease provides important information with respect to the responsiveness of the patient to agents such as β-IFN.

In addition to the exemplified MS, EAE and NO, a number of other diseases are known in the art to be associated with β-IFN or to have a role for Th17 in the pathogenesis of disease. Such diseases are linked together as conditions in which Th17 cells play a role in the pathology. In that the methods of the invention address biomarkers and therapies associated with Th17 cells, the methods of the invention broadly find use with these diseases.

Inflammatory diseases of interest include, without limitation Secondary Progressive Multiple Sclerosis (SPMS); Primary Progressive Multiple Sclerosis (PPMS); Neuromyelitis Optica (NMO); Psoriasis; Systemic Lupus Erythematosis (SLE); Ulcerative Colitis; Crohn's Disease; Ankylosing Spondylitis (see, for example, Mei et al. (2011) Clin. Rheumatol. 30:269-273; and Shen et al. (2009) Arthr. & Rheum. 60:1647-1656); Rheumatoid Arthritis (RA); Diabetes Mellitus type 1 (IDDM); Asthma; Chronic Obstructive Pulmonary Disorder (COPD); Chronic Hepatitis; Amyotrophic Lateral Sclerosis (ALS); Alzheimer's Disease (AD); Parkinson's Disease; Frontotemporal Lobar Degeneration (FTLD), atherosclerosis/cardiovascular disease, and obesity/metabolic syndrome. Applying the methods of the invention with respect to identifying mechanistic biomarkers to these other diseases leads to identification of biomarkers suitable for a diagnostic to predict response to therapy, including without limitation β-IFN treatment. In other embodiments, the application of biomarkers identified herein as useful in distinguishing between TH1 and Th17 subtypes of disease is provided for determining the responsiveness of a patient suffering from disease to β-IFN treatment, as well as other therapies relevant to TH17 associated diseases.

As discussed in Abraham and Cho (2009) Annu Rev Med. 60:97-110, the intestinal immune system has the challenge of maintaining both a state of tolerance toward intestinal antigens and the ability to combat pathogens. This balance is partially achieved by reciprocal regulation of proinflammatory, effector CD4+ T cells and tolerizing, suppressive regulatory T cells. Inflammatory bowel disease (IBD) comprises Crohn's disease (CD) and ulcerative colitis (UC). Genome-wide association studies have linked CD to a number of IL-23 pathway genes, notably IL23R (interleukin 23 receptor). Similar associations in IL-23 pathway genes have been observed in UC. IL23R is a key differentiation feature of CD4+ Th17 cells. The identification of IL-23 pathway and Th17 expressed genes in IBD pathogenesis highlights the importance of the proper regulation of the IL-23/Th17 pathway in maintaining intestinal immune homeostasis. Trials with IFN-β and other type I IFNs have shown some efficacy in ulcerative colitis (UC) (Mannon et al. (2010) Gut). A recent study of IFN-β treatment of UC assessed the biological differences between responders and non-responders. These authors observed a result that is stunning in its congruity to IFN-β responders vs non-responders in RRMS. Investigators at NIH found that prior to IFN-β therapy in UC, those patients who were nonresponders to IFN-β had significantly higher IL-17 production from lamina propria T cells compared to responders.

In most other autoimmune disorders, including SLE, psoriasis, RA and NMO, type I IFN contributes to the pathogenesis of the disease (see, for example, Bennett et al. (2003) J Exp Med 197 (6), 711-723; van der Pouw Kraan et al. (2007) Ann Rheum Dis 66 (8), 1008-1014; van der Fits et al. (2004) J Invest Dermatol 122 (1), 51-60). It now emerges that TH17 also plays a pivotal role in these diseases (see van Hamburg et al. (2010) Arthritis Rheum. 63 (1), 73-83; Shah et al. (2010) Arthritis Res Ther 12 (2), R53; Fujishima et al. (2010) Arch Dermatol Res 302 (7), 499-505; Watanabe et al. (2009) J Invest Dermatol 129 (3), 650-656; Ishizu, et al. (2005) Brain 128 (Pt 5), 988-1002).

In the dermatological disease, psoriasis, keratinocytes proliferate in an abnormal manner in response to a chronic inflammatory reaction. The IL-23/TH17 pathway has been implicated in the pathogenesis of psoriasis (see Wilson et al. (2007) Nat Immunol 8 (9), 950-957; Ortega et al. (2009) J Leukoc Biol 86 (2), 435-443). Genetic studies have identified polymorphisms in IL-23/12p40 and IL-23R as risk factors for developing psoriasis (see Cargill et al. (2007) Am J Hum Genet 80 (2), 273-290; Nair et al. (2008) J Invest Dermatol 128 (7), 1653-1661). In mice intradermal injections of IL-23 induces inflammation in the epidermis that resembles psoriasis. Moreover, monoclonal antibody (mAb) therapy that blocks IL-23 signaling have been successful in clinical trials of psoriasis (see Krueger et al. (2007) N Engl J Med 356 (6), 580-592; Kimball et al. (2008) J Am Acad Dermatol; Segal, B. M. et al. (2008) Lancet Neurol 7 (9), 796-804). Other TH17 cytokines identified in psoriasis include IL-17A, IL-22, IL-8 and also IL-17F (Coimbra et al. Br J Dermatol 163 (6), 1282-1290). Neutralizing IL-17 with mAb, as with anti-IL-23, is showing promise as a treatment for psoriasis (Hueber et al. Sci Transl Med 2 (52), 52ra72). In addition to TH17, type I IFN has also been implicated as an important mediator of inflammation in psoriasis. Like SLE, the transcriptional signature of type I IFN is activated within the psoriatic plaques. The cellular source of type I IFN is likely plasmacytoid dendritic cells (pDC). Among the first events that occurs in this disease, is the recruitment of pDCs to the preplaque area where they are activated and secrete large quantities of IFNβ and IFN-$\alpha_{55}$. Experiments using blocking antibodies and knockout mice have demonstrated that that type I IFNs play a pathogenic role in psoriasis (Hida et al. (2000) Immunity 13 (5), 643-655). Type I IFN has been identified as a key component for the pathology in several cases of psoriasis that developed in RRMS patients and in Hepatitis C patients who received type I IFN as a treatment for their disease (Seckin et al. (2004) Pediatr Dermatol 21 (5), 577-579; Downs and Dunnill (2000) C. Clin Exp Dermatol 25 (4), 351-352). As a whole, the observations encompassing these examples from pre-clinical experiments in mice to clinical studies in human diseases suggest that type I IFN and TH17 are a dangerous combination in autoimmune diseases, where endogenous expression or therapeutic administration of IFN-β in conditions with a Th17 bias, only worsens the disease.

In one embodiment of the invention, the disease is rheumatoid arthritis (see, for example, Wang et al. (2011) Rheum. Int., and Shen et al., supra.). Disease modifying anti-rheumatoid drugs (DMARD) of interest include, without limitation, cytokine blocking agents, e.g. anti-TNFα antibodies, soluble TNFα receptor, soluble IL-1 receptor (Anakinra), and anti-IL-6R antibodies (Tocilizumab); T cell targeted therapies (CTLA4-Ig [Abatacept]), B cell targeted therapies (anti-CD20 [Rituximab]), chemotherapeutic drugs, and the like. One of the monoclonal anti-TNF antibodies is infliximab (REMICADE®). Infliximab is a chimeric human/mouse monoclonal anti-TNFα antibody composed of the constant regions of human (Hu) IgG1κ, coupled to the Fv region of a high-affinity neutralizing murine anti-huTNFa antibody. D2E7, also known as adalumimab (HUMIRA™), was generated by phage display technology and is fully human. Etanercept (sTNF-RII:Fc; ENBREL™) is the best studied of the sTNF-R and is approved for the treatment of rheumatoid arthritis in adults and in children.

In systemic lupus erythematosus (SLE), Interleukin 17 (IL-17) was recently linked to pathogenesis (see Mok et al. (2010) J Rheumatol. 37(10):2046-52; Crispin and Tsokos (2010) Curr Opin Rheumatol. 22(5):499-503; and Nalbandian et al. (2009) Clin Exp Immunol. 157(2):209-15). SLE patients had higher serum IL-17 levels than healthy controls. Elevated serum IL-23 was found in patients with inflammatory manifestations including cutaneous involvement and serositis. The lack of correlation between Th17, Th1, and Th2 cytokines suggested independent regulatory mechanisms for these cytokines. IL-17 has also been implicated in the related disease, cutaneous lupus erythematosus (see Tanasescu et al. (2010) Eur J Intern Med. 21(3):202-7). IL-17 isoforms (IL-17A and IL-17F) are implicated in SLE but also in DLE and SCLE immunopathogenesis.

In Parkinson's disease, regulatory T cells have been shown to attenuate TH17 cell mediated nigrostriatal dopaminergic neurodegeneration (see, for example, Reynolds et al. J Immunol. 2010 Mar. 1; 184(5):2261-71). In models of Parkinson's disease, adaptive immune responses to antigenic epitopes exacerbate neuroinflammation and nigrostriatal degeneration. Such neuroimmune degenerative activities, in significant measure, are Th17 cell-mediated, with CD4$^+$CD25$^+$ regulatory T cell (Treg) dysfunction.

Th17 cells have been recently shown to induce antigen-specific cell-mediated proliferative glomerulonephritis (see Ooi et al. (2010) Nephrology (Carlton) 15(5):513-21). There is increasing evidence implicating Th17 cells in anti-glomerular basement membrane disease, lupus nephritis and pauci-immune glomerulonephritis.

In type 1 Diabetes Mellitus (IDDM) there is evidence of IL-17 production by monocytes and that IL-8 granulocyte chemokine that is associated with IL-17 and seen in NMO and psoriasis (see van Sickle et al. (2009) Cytokine 48:290-294).

Asthma is characterized by chronic airway inflammation with intense eosinophil and lymphocyte infiltration, mucus hyperproduction, and airway hyperresponsiveness. Antigen-specific Th2 cells and their cytokines such as IL-4, IL-5, and IL-13 orchestrate these pathognomonic features of asthma. IL-17-producing CD4$^+$ T cells (Th17 cells) and IL-23, an IL-12-related cytokine that is essential for survival and functional maturation of Th17 cells, are involved in antigen-induced airway inflammation. IL-23 and Th17 cells are involved not only in causing antigen-induced neutrophil recruitment into the airways but also in the enhancement of Th2 cell-mediated eosinophil recruitment into the airways. (see Nakajima et al. (2010) Immune Network 10:1).

Accumulating evidences indicate that chronic inflammatory responses and adaptive immunity play important roles in the development and progression of chronic obstructive pulmonary disease (COPD) (see Hong and Lee (2010) Imm. Net. 10(4):109). Recently, it has been shown that Th17 cells, which have been implicated in the pathogenesis of several inflammatory and autoimmune diseases, are involved in airway inflammation and COPD. Peripheral blood CD4 T cells from patients with COPD have higher level of IFN-γ but not IL-13 in response to elastin peptides, major constituents of the extracellular matrix in lung. Further study showed that Th17 cells are present in lung parenchyma of patients with emphysema, and elastin peptides stimulation could differentiate both Th1 and Th17 cells.

Interleukin-17 (IL-17)-producing CD4$^+$ T cells (Th17)-mediated immune response is also associated with chronic hepatitis B virus (HBV) infection (see Wu et al. Journal of Gastroenterology and Hepatology 25 (2010) 750-757; Zhang et al. (2010) Hepatology (2010) 51:81-91). Th17 cells are highly enriched in both peripheral blood and liver of CHB patients, and exhibit a potential to exacerbate liver damage during chronic HBV infection. The induction of IL-10 can be one mechanism of constraining pro-inflammatory Th17 responses.

Atherosclerosis has been linked to TH17 cells (see Chen et al. (2010) J Innate Immun. 2(4):325-33).

A pathological transactive response DNA-binding protein is the major disease protein in amyotrophic lateral sclerosis (ALS) and frontotemporal lobar degeneration (FTLD) with ubiquitin-positive inclusions (now known as FTLD-TDP) (See, for example, Geser et al. (2010) Neuropathology 30(2): 103-12). The discovery of pathological TDP-43 solidified the idea that these disorders are multi-system diseases, leading to the concept of a TDP-43 proteinopathy as a spectrum of disorders comprised of different clinical and pathological entities extending from ALS to ALS with cognitive impairment/dementia and FTLD-TDP without or with motor neuron disease (FTLD-MND). These align along a broad disease continuum sharing similar pathogenetic mechanisms linked to pathological TDP-43.

There is evidence that immunological factors can be involved in pathogenetic mechanisms of amyotrophic lateral sclerosis (ALS) (see Rentzos et al. (2010) Acta Neurol Scand. 122(6):425-9. IL-17 and IL-23 serum levels were higher in patients with ALS as compared with patients with NIND. IL-17 and IL-23 CSF levels were also increased in patients with ALS.

Increased activity of Th-17 and Th-9 lymphocytes and a skewing of the post-thymic differentiation pathway are seen in Alzheimer's disease (Saresella ET AL. (2010) Brain Behav Immun.) Cytokines (IL-21, IL-6, IL-23) and TF (RORγ) involved in the differentiation of Th-17 cells), as well as cytokines (IL-21, IL-22) generated by such cells, and IL-9, produced by Th-9 cells, are significantly increased in AD. This is accompanied by a shift of post-thymic differentiation pathways favoring the accumulation of differentiated, effector T lymphocytes.

Frontotemporal Lobar Degeneration (FTLD) (see Hu et al. (2010) Neurology) shows CSF levels of multiple analytes that differ between FTLD-TDP and FTLD-tau, including Fas, neuropeptides (agouti-related peptide and adrenocorticotropic hormone), and chemokines (IL-23, IL-17).

Atherosclerosis is an inflammatory disease in which interferon (IFN)-γ, the signature cytokine of Th1 cells, plays a central role. Interleukin (IL)-17, the signature cytokine of Th17 cells, is also associated with human coronary atherosclerosis. IL-17 is produced concomitantly with IFN-γ by coronary artery-infiltrating T cells and that these cytokines act synergistically to induce proinflammatory responses in vascular smooth muscle cells. (see Eid et al. Circulation. 2009; 119:1424-1432.) Gao et al. J. Immun., 2010, 185: 5820-5827 evaluated the production and function of Th17 and Th1 cells in atherosclerotic-susceptible ApoE mice. The proportion of Th17 cells, as well as Th1, increased in atherosclerotic mice compared with nonatherosclerotic wild-type littermates. Treatment of the mice with neutralizing anti-IL-17 Ab dramatically inhibited the development of atherosclerotic plaque, whereas rIL-17 application significantly promoted the formation of atherosclerotic plaque.

Obesity is associated with numerous inflammatory conditions including atherosclerosis, autoimmune disease and cancer (see Winer et al. (2009) Eur. J. Immunol. 39: 2629-2635). Obesity selectively promotes an expansion of the Th17 T-cell sublineage, a subset with prominent pro-inflammatory roles. T-cells from diet-induced obese mice expand Th17 cell pools and produce progressively more IL-17 than lean littermates in an IL-6-dependent process. The well-described association of obesity with inflammatory and autoimmune disease is mechanistically linked to a Th17 bias. Increased activity of interleukin-23/interleukin-17 is also seen in obese women, (see Sumarac-Dumanovic et al. (2009) International Journal of Obesity 33, 151-156). Blood concentrations of IL-17, IL-23, MIF and leptin, but not IL-12 or IFN-γ, were higher in obese compared with lean women. The interleukin-23/IL-17 axis was stimulated in obese women independently of the increase in abdominal fat, insulin resistance, leptin and MIF levels.

Inflammatory Demyelinating Disease.

The term "inflammatory" response is the development of a humoral (antibody mediated) and/or a cellular (mediated by antigen-specific T cells or their secretion products) response. Inflammatory demyelinating diseases of the central nervous system are of particular interest and include, without limitation, multiple sclerosis (MS), neuromyelitis optica (NO), and experimental acquired encephalitis (EAE). Demyelinating inflammatory diseases of the peripheral nervous system include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy.

Multiple sclerosis is characterized by various symptoms and signs of CNS dysfunction, with remissions and recurring exacerbations. Classifications of interest for analysis by the methods of the invention include relapsing remitting MS (RRMS), primary progressive MS (PPMS) and secondary progressive MS (SPMS). The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat can accentuate symptoms and signs.

The course is highly varied, unpredictable, and, in most patients, remittent. At first, months or years of remission can separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, per year. Over 10 to 20 years, approximately 50% of RR MS patients develop secondary progressive MS (SP MS) which is characterized by incomplete recovery between attacks and accumulation of neurologic deficits resulting in increasing disability.

Secondary Progressive Multiple Sclerosis (SPMS) (see Kappos et al. (2004) Neurology 63(10):1779-87) in a study with interferon beta-1b (IFNB-1b) in secondary progressive multiple sclerosis (SPMS) showed divergent results with regard to their primary outcome of sustained Expanded Disability Status Scale (EDSS) progression. Certain patients were found to benefit from the treatment, where pronounced disability progression and continuing relapse activity might help in identifying those patients in the secondary progressive phase of the disease who are more likely to benefit from treatment.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, can show plaques. It can also detect treatable nondemyelinating lesions at the junction of the spinal cord and medulla (eg, subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions can also be visible on contrast-enhanced CT scans; sensitivity can be increased by giving twice the iodine dose and delaying scanning (double-dose delayed CT scan).

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Neuromyelitis optica (NMO), or Devic's disease, is an autoimmune, inflammatory disorder of the optic nerves and spinal cord. Although inflammation can affect the brain, the disorder is distinct from multiple sclerosis, having a different pattern of response to therapy, possibly a different pattern of autoantigens and involvement of different lymphocyte subsets.

The main symptoms of Devic's disease are loss of vision and spinal cord function. As for other etiologies of optic neuritis, the visual impairment usually manifests as decreased visual acuity, although visual field defects, or loss of color vision can occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelinization), but they differ from MS pattern II lesions in their prominent perivascular distribution. Therefore, the pattern of inflammation is often quite distinct from that seen in MS.

Attacks are treated with short courses of high dosage intravenous corticosteroids such as methylprednisolone IV. When attacks progress or do not respond to corticosteroid treatment, plasmapheresis can be used. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study.

The disease can be monophasic, i.e. a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike MS, Devic's disease rarely has a secondary progressive phase in which patients have increasing neurologic decline between attacks without remission. Instead, disabilities arise from the acute attacks.

Studies have suggested a role for Th17 T cells and autoantigens, including aquaporin and myelin proteins in the pathology of NO. See, for example, Kira (2010) Pathophysiology, "Neuromyelitis optica and opticospinal multiple sclerosis: Mechanisms and pathogenesis."

T helper 17 cells (Th17) are a subset of T helper cells, characterized by their production of interleukin 17 (IL-17).

They are considered developmentally distinct from Th1 and Th2 cells and excessive amounts of the cell are thought to play a key role in autoimmune disease.

In humans, a combination of TGF-β, IL-1β and IL-23 induces Th17 differentiation from naive T cells. Both interferon gamma (IFNγ) and IL-4, the main stimulators of Th1 and Th2 differentiation respectively, negatively regulate Th17 differentiation.

Th17 cells primarily produce two main members of the IL-17 family; IL-17A and IL-17F, which are involved in the recruitment, activation and migration of neutrophils. These cells also secrete IL-21 and IL-22.

T helper 1 cells (Th1). Proliferating helper T cells that develop into effector T cells differentiate into two major subtypes of cells known as Th1 and Th2 cells. Th1 cells primarily produce IFN-γ and TNF-β cytokines. IFN-γ increases the production of interleukin-12 by dendritic cells and macrophages, and via positive feedback, IL-12 stimulates the production of IFN-γ in helper T cells, thereby promoting the Th1 profile. IFN-γ also inhibits the production of cytokines such as IL-4. Conditions that polarize to the TH1 type include antigen presenting cells and IL-12.

Interleukin-17 (IL-17) refers to a group of cytokines called the IL-17 family. IL-17 shows high homology to viral IL-17 encoded by an open reading frame of the T lymphotropic rhadinovirus Herpesvirus saimiri. To elicit its functions, IL-17 binds to a type I cell surface receptor called IL-17R of which there are at least three variants IL17RA, IL17RB, and IL17RC. Inhibitors of IL-17 include, without limitation, antibodies specific for the cytokine and/or its receptor. For example, AIN457, is a fully human antibody to interleukin-17A. "IL-17F" as used herein refers to IL-17F monomers or multimers containing at least one IL-17F monomer. "IL-17A" as used herein refers to IL-17A monomers or multimers containing at least one IL-17A monomer. "IL-17" as used herein can refer to either IL-17F or IL-17A.

In response to β-IFN, human T cells produce increased amounts of IL-17F, but not IL-17A, which can be accounted for by the presence of putative Type I interferon elements upstream of IL-17F but not IL-17A. In some embodiments of the invention, classification of β-IFN responsiveness in NMO or MS relies on a determination of IL-17F levels, which are optionally compared with levels of IL-17A. Increased levels of Il-17F and baseline levels of IL-17A are indicative of NMO or β-IFN non-responsive MS.

Members of the IL-17 family include IL-17B, IL-17C, IL-17D, IL-17E (also called IL-25), and IL-17F. All members of the IL-17 family have a similar protein structure, with four highly conserved cysteine residues critical to their 3-dimensional shape, although with no sequence similarity to any other known cytokines. IL-17A is a 155 amino acid protein that is a disulfide linked, homodimeric, secreted glycoprotein with a molecular mass of 35 kDa. Each subunit of the homodimer is approximately 15-20 KDa. The structure of IL-17 consists of a signal peptide of 23 amino acids (aa) followed by a 123 aa chain region characteristic of the IL-17 family. IL-17F is structurally similar to the cysteine knot family of proteins that includes the neurotrophins. The cysteine knot fold is characterized by two sets of paired β-strands stabilized by three disulfide interactions. However, in contrast to the other cysteine knot proteins, IL-17F lacks the third disulfide bond. Instead, a serine replaces the cysteine at this position. This unique feature is conserved in the other IL-17 family members. IL-17F also dimerizes in a fashion similar to nerve growth factor (NGF) and other neurotrophins. The genetic sequence of IL-17F can be accessed at Genbank, NM_052872. Also see Ely et al. (2009) Nat. Immunol. 10 (12), 1245-1251; Kawaguchi e al. (2002) J. Biol. Chem. 277 (18), 15229-15232; Starnes et al. (2001) J. Immunol. 167 (8), 4137-4140; and Hymowitz et al. (2001) EMBO J. 20 (19), 5332-5341, each herein specifically incorporated by reference.

Numerous immune regulatory functions have been reported for the IL-17 family. Most notably, IL-17 is involved in inducing and mediating proinflammatory and allergic responses. IL-17 induces the production of many other cytokines and prostaglandins from various cell types (fibroblasts, endothelial cells, epithelial cells, keratinocytes and macrophages). Each member of the IL-17 family has a distinct pattern of cellular expression. The expression of IL-17A and IL-17F appear to be restricted to a small group of activated T cells, and upregulated during inflammation.

An N-linked glycosylation site on the protein was first identified after purification of the protein revealed two bands, one at 15 KDa and another at 20 KDa. Comparison of different members of the IL-17 family revealed four conserved cysteines that form two disulfide bonds.[5] IL-17 is unique in that it bears no resemblance to other known interleukins. Furthermore, IL-17 bears no resemblance to any other known proteins or structural domains.[4]

The IL-17 receptor family consists of five, broadly distributed receptors that present with individual ligand specificities. Within this family of receptors, IL-17R is the best described. IL-17R binds both IL-17A and IL-17F and is expressed in multiple tissues: vascular endothelial cells, peripheral T cells, B cell lineages, fibroblast, lung, myelomonocytic cells and marrow stromal cells.

IL-7. For sequence information of the human protein, see Goodwin et al. (1989) Proc Natl Acad Sci USA. 86:302-306, herein specifically incorporated by reference. The gene for human IL-7 is located on chromosome 8q12-13, spans 6 exons, and has open-reading frame of 534 base pairs (177 amino acids), including a 25-amino acid signal peptide. Homology between the human and the murine IL-7 sequence is 81% in the coding regions and approximately 60% to 70% in the 5' and 3' noncoding regions. The sequence of human IL-7 predicts a molecular weight of 17.4 kd, but glycosylation results in an active protein of 25 kd. IL-7 is classified as a type 1 short-chain cytokine of the hematopoietin family. IL-7 is essentially a tissue-derived cytokine, with the primary sources stromal and epithelial cells in various location.

IL-7 is a member of the family of cytokines that signal through the common cytokine gamma chain (γc). IL-7 also uses a second component, the IL-7 receptor alpha chain (IL-7Rα) (CD127). Signaling through the IL-7R requires both IL-7Rα and the γc component.

IL-23 alpha subunit is a protein encoded by the IL23A gene (see Oppmann et al. (2001) *Immunity* 13 (5): 715-25). This gene encodes the p19 subunit of the heterodimeric cytokine interleukin 23 (IL23). IL23 is composed of this protein and the p40 subunit of interleukin 12. The receptor of IL23 is formed by the beta 1 subunit of IL12 (IL12RB1) and an IL23 specific subunit, IL23R. Both IL23 and IL12 can activate the transcription activator STAT4, and stimulate the production of interferon-gamma (IFNG). In contrast to IL12, which acts mainly on naive CD4(+) T cells, IL23 preferentially acts on memory CD4(+) T cells.

Inhibitors of IL-23 include, without limitation, antibodies that selectively bind to one or both subunits of the heterodimeric cytokine, antibodies that bind to and block the IL-23 receptor, and the like. Antibodies of interest include, without limitation, IL12/23 p40 neutralising antibody, ustekinumab.

Interferon beta-1a is a drug in the interferon family used to treat multiple sclerosis (MS). It is produced by mammalian cells while Interferon beta-1b is produced in modified *E. coli*. Interferons have been shown to have about a 18-38% reduction in the rate of MS relapses, and to slow the progression of disability in MS patients. Commercially available products include Avonex (Biogen Idec); Rebif (EMD Serono); and CinnoVex (CinnaGen). Closely related is Interferon beta-1b, which is marketed in the US as Betaseron, or Extavia. β-IFN find use in the treatment of patients classified by the methods of the invention as responsive to β-interferon.

Copaxone, manufactured by Teva Marion Partners, is the brand name for a synthetic chemical used to modify the course of multiple sclerosis. The generic name of Copaxone is Glatiramer Acetate which is often shortened to GA. In early trials of the drug, it was known as Copolymer-1 and Cop-1. Copaxone is a random chain of amino acids—Glutamic acid, Lysine, Alanine and Tyrosine (hence GLATiramer). It is synthesized in solution from these amino acids a ratio of approximately 5 parts Alanine to 3 of Lysine, 1.5 of Glutamic acid and 1 of Tyrosine using N-carboxyamino acid anhydrides.

Copaxone has been shown in clinical trials to reduce the average relapse rate in people with the relapsing-remitting (RRMS) form of the disease. Copaxone has also been shown to limit the formation of new MS-related lesions in the central nervous system and to reduce brain atrophy. Copaxone finds use in the treatment of patients classified by the methods of the invention as unresponsive to β-interferon.

Simvastatin, the lipid-lowering drug first marketed as Zocor, has been investigated for use in multiple sclerosis, and shown to inhibit Th17 cell differentiation in patients with relapsing-remitting multiple sclerosis. Experiments suggest that simvastatin alters CD45RA+ cells undergoing Th17 differentiation. Simvastatin and other statins find use in the treatment of patients classified by the methods of the invention as unresponsive to β-interferon.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response. An "immunogen" is capable of inducing an immunological response against itself on administration to a mammal or due to autoimmune disease.

The terms "biomarker," "biomarkers," "marker" or "markers" refer to, without limitation, cytokines, chemokines, growth factors, proteins, peptides, nucleic acids, oligonucleotides, and metabolites, together with their related metabolites, mutations, variants, polymorphisms, modifications, fragments, subunits, degradation products, elements, and other analytes or sample-derived measures. Markers can also include mutated proteins, mutated nucleic acids, variations in copy numbers and/or transcript variants. Markers also encompass non-blood borne factors and non-analyte physiological markers of health status, and/or other factors or markers not measured from samples (e.g., biological samples such as bodily fluids), such as clinical parameters and traditional factors for clinical assessments. Markers can also include any indices that are calculated and/or created mathematically. Markers can also include combinations of any one or more of the foregoing measurements, including temporal trends and differences. Markers can include PDGFBB, sFAS ligand, M-CSF, MIP1a, TNF-B, IFNa, IL-1RA, MCP-1, IL-2, IL-6, IL-8, FGFb, IL-7, TGF-b, IFNb, IL-13, IL-17F, EOTAXIN, IL-1a, MCP-3, LIF, NGF, RANTES, IL-5, MIP1b, IL-12p70, and/or HGF.

A "subject" or "patient" in the context of the present teachings is generally a mammal. Mammals other than humans can be advantageously used as subjects that represent animal models of inflammation. A subject can be male or female.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis to, e.g., determine whether a subject is a responder or a non-responder to a therapy (e.g., an IFN treatment as described herein).

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring, PCR, microarray, one or more primers, one or more probes, antibody binding, or ELISA. The phrase also encompasses receiving a set of data, e.g., from a third party that has processed the sample to experimentally determine the dataset. Additionally, the phrase encompasses mining data from at least one database or at least one publication or a combination of databases and publications.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUC or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC (area under the curve) of at least about 0.7, at least about 0.75, at least about 0.8, at least about 0.85, at least about 0.9, or higher.

As is known in the art, the relative sensitivity and specificity of a predictive model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of inflammatory disease can be accomplished by administration of the agent prior to development of a relapse. The treatment of ongoing disease, where the treatment stabilizes or improves the clinical symptoms of the patient, is of particular interest.

Methods

Cytokines are messenger molecules produced by B cells, T cells, macrophage, dendritic cells and other immune and host cells. Cytokines play roles in the pathogenesis of inflammatory diseases, including without limitation multiple sclerosis, neuromyelitis optica, and the like. Cytokines include chemokines, lymphokines, growth factors, angiogenesis factors, and other secreted and cell surface molecules that transmit signals to other cells. Markers of the present methods include cytokines. Markers of interest for the methods of the invention include, without limitation, IL-17F, IL-17A, β-IFN, γ-IFN, IL-23, PDGFBB, sFAS ligand, M-CSF, MIP1a, TNF-B, IFNα, IL-1RA, MCP-1, IL-2, IL-6, IL-8, FGFβ, IL-7, TGF-β, IL-13, IL-17F, EOTAXIN, IL-1a, MCP-3, LIF, NGF, RANTES, IL-5, MIP1b, IL-12p70, and HGF. While serum levels of IL-17F are found to be increased in some patient samples, in some cases serum levels of IL-17A can be normal. Serum levels of IL-7 are also of interest, and in some patient samples have been shown to inversely correlate with IL-17F serum levels.

In one embodiment of the invention, a method is provided for determining which immunomodulatory treatment a patient, e.g. an MS patient, will be non-responsive to, the method comprising determining levels of at least one marker in a patient, where the marker(s) is indicative of the TH1/TH17 status of the patient. A patient having high levels of markers indicative of a TH17 subtype, e.g. IL-17F, IL-5, IL-8, IL-23, β-IFN, etc., or low levels of a marker, e.g. IL-7, indicative of a TH1-subtype, relative to a non-diseased individual or a patient with a known responder phenotype, is classified as non-responder to TH1 subtype immunotherapy, which therapies include without limitation, administration of β-IFN. Such non-responder patients can be treated with alternative therapies, including, without limitation, treatment with an IL-17 and/or IL-23 inhibitor, γ-IFN, and the like. Patients of a TH1-subtype can be treated with an appropriate therapy, including without limitation administration of β-IFN.

The differential presence of these markers is shown to provide for prognostic evaluations to detect individuals having clinical subtypes that correspond to responsiveness or non-responsiveness to treatments of interest. In general, such prognostic methods involve determining the presence or level of cytokines in an individual sample. A variety of different assays can be utilized to quantitate the presence of such markers. Many such methods are known to one of skill in the art, including ELISA, protein arrays, eTag system, bead based systems, tag or other array based systems etc. Examples of such methods are set forth in the art, including, inter alia, chip-based capillary electrophoresis: Colyer et al. (1997) J Chromatogr A. 781(1-2):271-6; mass spectroscopy: Petricoin et al. (2002) Lancet 359: 572-77; eTag systems: Chan-Hui et al. (2004) Clinical Immunology 111:162-174; microparticle-enhanced nephelometric immunoassay: Montagne et al. (1992) Eur J Clin Chem Clin Biochem. 30(4):217-22; antigen arrays: Robinson et al. (2002) Nature Medicine, 8:295-301; the Luminex XMAP bead array system; and the like, each of which are herein incorporated by reference. Detection can utilize one or a panel of specific binding members, e.g. a panel or cocktail of binding members specific for one, two, three, four, five or more markers.

The signature pattern can be generated from a biological sample using any convenient protocol, for example as described below. The readout can be a mean, average, median or the variance or other statistically or mathematically-derived value associated with the measurement. The marker readout information can be further refined by direct comparison with the corresponding reference or control pattern. A binding pattern can be evaluated on a number of points: to determine if there is a statistically significant change at any point in the data matrix; whether the change is an increase or decrease in the binding; whether the change is specific for one or more physiological states, and the like. The absolute values obtained for each marker under identical conditions will display a variability that is inherent in live biological systems and also reflects the variability inherent between individuals.

Following obtainment of the signature pattern from the sample being assayed, the signature pattern is compared with a reference or control profile to make a prognosis regarding the phenotype of the patient from which the sample was obtained/derived. Typically a comparison is made with a sample or set of samples from an unaffected, normal source. Additionally, a reference or control signature pattern can be a signature pattern that is obtained from a sample of a patient known to be responsive or non-responsive to the therapy of interest, and therefore can be a positive reference or control profile.

In certain embodiments, the obtained signature pattern is compared to a single reference/control profile to obtain information regarding the phenotype of the patient being assayed. In yet other embodiments, the obtained signature pattern is compared to two or more different reference/control profiles to obtain more in depth information regarding the phenotype of the patient. For example, the obtained signature pattern can be compared to a positive and negative reference profile to obtain confirmed information regarding whether the patient has the phenotype of interest.

Samples can be obtained from the tissues or fluids of an individual. For example, samples can be obtained from whole blood, tissue biopsy, serum, etc. Other sources of samples are body fluids such as lymph, cerebrospinal fluid, and the like. Also included in the term are derivatives and fractions of such cells and fluids. Diagnostic samples are collected any time after an individual is suspected to have an inflammatory disease or has exhibited symptoms that predict such a disease.

Various immunoassays designed to quantitate markers can be used in screening. Measuring the concentration of the target protein in a sample or fraction thereof can be accomplished by a variety of specific assays. For example, a conventional sandwich type assay can be used in an array, ELISA, RIA, etc. format.

Other immunoassays are known in the art and can find use as diagnostics. Ouchterlony plates provide a simple determination of antibody binding. Western blots can be performed on protein gels or protein spots on filters, using a detection system specific for the markers as desired, conveniently using a labeling method.

For multiplex analysis of markers, arrays containing one or more anti-cytokine affinity reagents, e.g. antibodies can be generated. Such an array can be constructed comprising antibodies against markers.

Arrays provide a high throughput technique that can assay a large number of markers in a sample. Arrays can be created by spotting a probe onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena et al. (1995) *Science* 270(5235):467-70; Shalon et al. (1996) *Genome Res*. 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

The detection reagents can be provided as part of a kit. Thus, the invention further provides kits for detecting the presence of a panel of specific markers of interest in a biological sample. Procedures using these kits can be performed by clinical laboratories, experimental laboratories, medical practitioners, or private individuals. The kits of the invention for detecting markers comprise affinity reagents useful for generating a prognostic signature pattern, which can be provided in solution or bound to a substrate. The kit can optionally provide additional components that are useful in the procedure, including, but not limited to, buffers, developing reagents, labels, reacting surfaces, means for detection, control samples, standards, instructions, and interpretive information.

In addition to the above components, the subject kits will further include instructions for practicing the subject methods. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that can be present is a website address which can be used via the internet to access the information at a removed site. Any convenient means can be present in the kits.

Assessment of Patient Outcomes

Patient outcomes and responder status can be assessed using imaging-based criteria such as radiographic scores, clinical and laboratory criteria. Multiple different imaging, clinical and laboratory criteria and scoring systems have been and are being developed to assess disease activity and response to therapy in inflammatory diseases, including without limitation inflammatory demyelinating disease, e.g. multiple sclerosis, neuromyelitis optica, etc.

A responder or non-responder pattern can be obtained as a dataset. The dataset comprises quantitative data for the presence in serum of at least 1 marker, usually IL-17F and/or IL-7, and can further contain quantitative data for IL-17A, γ-IFN, IL-5, IL7, IL-8, IL-23, β-IFN, etc. Other markers are described herein. The dataset optionally quantitative data for the presence in a clinical sample of other markers, including T cell presence or specificity, clinical indices, and the like. Clinical factors are described in more detail below.

In order to identify profiles that are indicative of responsiveness, a statistical test will provide a confidence level for a change in the expression, titers or concentration of markers between the test and control profiles to be considered significant, where the control profile can be for responsiveness or non-responsiveness. The raw data can be initially analyzed by measuring the values for each marker, usually in duplicate, triplicate, quadruplicate or in 5-10 replicate features per marker.

A test dataset is considered to be different than a control dataset if one or more of the parameter values of the profile exceeds the limits that correspond to a predefined level of significance.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering can be performed, where the Pearson correlation is employed as the clustering metric. One approach is to consider a patient disease dataset as a "learning sample" in a problem of "supervised learning". CART is a standard in applications to medicine (Singer (1999) Recursive Partitioning in the Health Sciences, Springer), which can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that can be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

These tools and methods can be applied to several classification problems. For example, methods can be developed from the following comparisons: i) all cases versus all controls, all cases versus nonresponsive controls, iii) all cases versus responsive controls.

In a second analytical approach, variables chosen in the cross-sectional analysis are separately employed as predictors. Given the specific outcome, the random lengths of time each patient will be observed, and selection of proteomic and other features, a parametric approach to analyzing responsiveness can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models can be used, especially since reductions of numbers of covariates to manageable size with the lasso will significantly simplify the analysis, allowing the possibility of an entirely nonparametric approach to survival.

These statistical tools are applicable to all manner of marker expression data. A set of data that can be easily determined, and that is highly informative regarding detection of individuals with clinically significant responsiveness to therapy is provided.

Also provided are databases of signature patterns for responsiveness. Such databases will typically comprise signature patterns of individuals having responsive phenotypes, non-responsive phenotypes, etc., where such profiles are as described above.

The analysis and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data can be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer can be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

Clinical Factors

In some embodiments, one or more clinical factors in a subject can be assessed. In some embodiments, assessment of one or more clinical factors in a subject can be combined with a marker analysis in the subject to identify responder v. non-responder status of the subject.

Various clinical factors are generally known one of ordinary skill in the art to be associated with the disease in question, e.g. MS. In some embodiments, clinical factors known to one of ordinary skill in the art to be associated with the disease, can include age, gender, race, family history, and/or medications. In some embodiments, a clinical factor can include age at onset of disease, duration of therapeutic treatment, and/or the relapse rate of the subject. Other examples of clinical factors are described in the Example section, e.g., Tables 1-2.

Informative Gene Groups

In addition to the specific, exemplary markers identified in this application by name, accession number, or sequence, included within the scope of the invention are all operable markers and methods for their use to determine responder v. non-responder status using expression values of variant sequences having at least 90% or at least 95% or at least 97% or greater identity to the exemplified marker nucleotide sequences or that encode proteins having sequences with at least 90% or at least 95% or at least 97% or greater identity to those encoded by the exemplified markers. The percentage of sequence identity can be determined using algorithms well known to those of ordinary skill in the art, including, e.g., BLASTN, and BLASTP, as described in Stephen F. Altschul et al., *J. Mol. Biol.* 215:403-410 (1990) and available at the National Center for Biotechnology Information website maintained by the National Institutes of Health.

Sequences of proteins discussed herein are publicly available, for example at Genbank, Swissprot, and the like. As a reference, exemplary Genbank accession numbers include: IL-17a Genbank accession no. Q16552; IL-17F Genbank accession no. Q96PD4; IFN-beta Genbank accession no. NP_002167; IL-23 Genbank accession no. AAH67512; PDGFB Genbank accession no. CAG30424; IL-7 Genbank accession no. NP_000871; IL-8 Genbank accession no. AAH13615; IL-6 Genbank accession no. AAH15511; TGF-beta Genbank accession no. AAA36738; IL-13 Genbank accession no. AAB01681; Eotaxin Genbank accession no. CAB07027; IL-1 a Genbank accession no. AAH13142; MCP3 Genbank accession no. AAH92436; LIF Genbank accession no. AAA51699; IL-5 Genbank accession no. NP_000870.

In accordance with an embodiment of the present invention, all operable markers and methods for their use in determining responder v. non-responder status now known or later discovered to be highly correlated with the expression of an exemplary marker can be used in addition to or in lieu of that exemplary marker. For the purposes of the present invention, such highly correlated markers or haplotypes are contemplated to be within the literal scope of the claimed inventions or alternatively encompassed as equivalents to the exemplary markers or haplotypes. Identification of markers or haplotypes having expression values that are highly correlated to those of the exemplary markers or haplotypes, and their use as a component for determining responder v. non-responder status is well within the level of ordinary skill in the art.

Therapeutic Agents

In one embodiment of the invention, modulators of T cell activity are used in the treatment of inflammatory diseases.

Various modulators know in the art find use in therapeutic methods guided by biomarker analysis of the present invention.

In various embodiments the therapeutic agent is a biological, e.g. a cytokine, antibody, soluble cytokine receptor, anti-sense oligonucleotide, siRNA, etc. Such biological agents encompass muteins and derivatives of the biological agent, which derivatives can include, for example, fusion proteins, pegylated derivatives, cholesterol conjugated derivatives, and the like as known in the art. Also included are antagonists of cytokines and cytokine receptors, e.g. traps and monoclonal antagonists, e.g. IL-1Ra, IL-1 Trap, sIL-4Ra, etc. Also included are biosimilar or bioequivalent drugs to the active agents set forth herein.

The method also provide for combination therapy, where the combination can provide for additive or synergistic benefits. Combinations of agents can be obtained with a second agent selected from one or more of the general classes of drugs commonly used in the treatment of the disease of interest, for example including corticosteroids and disease modifying drugs, antigen-specific agents, etc. Corticosteroids have a short onset of action, but many disease modifying drugs take several weeks or months to demonstrate a clinical effect. These agents include methotrexate, leflunomide (Arava™), etanercept (Enbrel™) infliximab (Remicade™), adalimumab (Humira™), anakinra (Kineret™), rituximab (Rituxan™) CTLA4-Ig (abatacept), antimalarials, gold salts, sulfasalazine, d-penicillamine, cyclosporin A, cyclophosphamide azathioprine; and the like. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

In some embodiments of the invention the therapeutic agent is a beta-interferon, including without limitation the currently approved drugs AVONEX™ (IFNβ 1A), BETASERON™ (IFN-β1B); EXTAVIA™ (IFN-β1B), REBIF™ (IFNβ 1A), and bioequivalents and derivatives, e.g. pegylated derivatives, thereof. Conditions that can be treated with β-interferons include MS, EAE, etc. Such diseases can also be treated with glatiramer acetate (Copaxone).

In some embodiments of the invention the therapeutic agent is a cytokine or an antagonist, agonist, mimetic, bioequivalent, or derivative thereof. Cytokines of interest include, without limitation, IL-1β; IL-2; IL-4; IL-5; IL-6; IL-7; IL-8; IL-10; IL-11; IL-12; IL-13; IL-15; IL-17 (including IL-17A, B, C, D, E, F separately and in combination, such as IL-17A/F); IL-18; IL-20; IL-21; IL-23; and IL29.

Antagonists of interleukins which can be soluble receptors, antibodies, small molecule drugs, etc. include, without limitation, anti-IL-1, e.g. canakinumab, anakinra, rilonacept, AMG108, XOMA052; anti-IL-4, AMG317; anti-IL-5, mepolizumab, reslizumab, SCH55700, MEDI-563 (receptor); anti-IL6, siltuximab, tocilizumab (receptor), CNTO 136; anti-IL-8, ABX-IL8; anti-IL-9, MEDI-528; anti-IL-12 and IL-23, ustekinumab, briakinumab; anti-IL-13, CAT-354, QAX576; anti-IL-15, AMG 714; anti-IL-17, AlN457, LY2439821, NI-1401; anti-IL-18, GSK1070806; anti-IL-20, NNC109-0012; anti-IL-22, fezakinumab; anti-IL-23, LY2525623. STA-5326 (also called apilimod) is a small molecule inhibitor of IL-12/23 function. LY2439821 and secukinumab (AlN457) are examples of anti-IL-17 monoclonal antibodies.

Antagonists of cytokines include antagonists of IFNα (anti-IFNα); IFNβ (anti-IFNβ); IFNγ (anti-IFNγ); G-CSF (anti-G-CSF); GM-CSF (anti-GM-CSF); Groα (anti-Groα); etc. Agonists of TNFα (anti TNFα), e.g. Enbrel (etanercept), Arcalyst (rilonacept), Amevive (alefacept), find use, for example in the treatment of rheumatic diseases. As used herein, rheumatic diseases can include Ankylosing Spondylitis, Gout, Rheumatoid Arthritis, acute and subacute Bursitis, Kawasaki Syndrome, Relapsing Polychondritis, Bursitis and Tendinitis, Juvenive Idiopathic Arthritis (Juvenile Rheumatoid Arthritis), Sjogren's Syndrome, Cryopyrin-associated Periodic Syndromes, Osteoarthritis, Systemic Sclerosis, Dermatomyositis, Polymyalgia Rheumaticia, Systemic Lupus Erythematous, Epicondylitis, Polymyositis, acute non-specific Tenosynovitis, Fibromyalgia, Psoriatic Arthritis and Vasculitis. Therapies known for rheumatic diseases also include Abatacept (Orencia); Adalimumab (Humira); Anakinra (Kineret); Aspirin (Ecotrin); Auranofin (Ridura); Aurothioglucose (Solganal); Azathioprine (Imuran); Celecoxib (Celebrex); Cyclosporin (Neoral); Etanercept (Enbrel); Gold sodium thiomalate (Myochrysine); Hydroxychloroquine Sulfate (Plaquenil); Infliximab (Remicade); Intravenous Immunoglobulin (Gammagard S/D); Leflunomide (Arava); Methylprednisolone acetate (Depo-Medrol); Methotrexate (Rheumatrex, Trexall); Penicillamine (Cuprimine); Prednisolone (Prednisone (Corticosteroids); Rilonacept (Arcalyst); Rituximab (Rituxan); Sulfasalazine (Azulfidine (Azulfidine EN-Tabs); Triamcinolone acetonide (Kenalog); Triamcinolone diacetate (Aristospan); Diclofenac (Voltaren (Cataflam (Arthrotec (combined with misoprostol)); Diflunisal (Dolobid); Etodolac (Lodine (Lodine XL); Fenoprofen (Nalfon (Nalfon 200); Flurbiprofen (Ansaid); Ibuprofen (Motrin, Tab-Profen, Vicoprofen, combined with hydrocodone) (Combunox, combined with oxycodone); Ibuprofen (Children's Advil); Indomethacin (Indocin, Indocin SR, Indo-Lemmon); Ketoprofen (Oruvail, Orudis); Meloxicam (Mobic); Nabumetone (Relafen); Naproxen (Naprosyn, Anaprox, Anaprox DS, EC-Naprosyn, Naprelan); Oxaprozin (Daypro); Piroxicam (Feldene); Sulindac (Clinoril); Tolmetin (Tolectin, Tolectin DS, Tolectin 600).

Agents that find use in the treatment of chronic hepatitis include, for example, ALFERON N™ INJECTION (IFN-αN3); INFERGEN™ (IFN-αCON-1); INTRON A™ (IFN-α2B); PEGASYS™ (PEG IFN-α2A); PEGINTERFERON™ (PEGIFN-α2A; RIBAVIRIN); PEGINTRON™ (PEGIFN-α2B); ROFERON A™ (IFN-α2A).

Agents that have been found useful in treating inflammatory diseases also include statins, e.g. pravastatin, simvastatin, lovastatin, fluvastatin, atorvistatin, pitavastatin, rosuvastatin, etc.

Monoclonal antibodies in use include, without limitation, ACTEMRA™ (tocilizumab); ARZERRA™ (ofatumumab); BEXXAR™ (tositumomab; $^{131}$I tositumomab); CAMPATH™ (alemtuzumab); CIMZIA™ (certolizumab pegol); HUMIRA™ (adalimumab); ILARIS™ (canakinumab); PROLIA™ (denosumab); REMICADE™ (infliximab); RITUXAN™ (rituximab); SIMPONI™ (golimumab); SIMULECT™ (basiliximab); STELARA™ (ustekinumab); TYSABRI™ (natalizumab); XGEVA™ (denosumab); XOLAIR™ (omalizumab); ZENAPAX™ (daclizumab). Monoclonal antibodies specific for amyloid include LY2062430 (solanezumab), PF-04360365, MABT5102A, bapineuzumab, gantenerumab.

Other therapeutic agents of interest include lenalidomide (Revlimid); fingolimod (Gilenya); teriflunomide; cladribine; and BG-12 (Panaclar, BG-00012, FAG-201); JAK inhibitors and Syk inhibitors, which include without limitation the JAK-3 inhibitor tasocitinib (CP-690,550); Syk inhibitor fostamatinib (R788) etc.

Patients categorized as TH17 type are generally non-responsive to β-IFN, but can be treated with, for example, copaxone, certain statins, an IL17 inhibitor, and IL-23 inhibitor, etc. as an alternative to β-IFN, where an effective dose or course of treatment of an agent is administered to the patient. Of particular interest are inhibitors of IL-17F. Alternatively such patients can be treated with an inhibitor of IL-23 as an alternative to β-IFN, where an effective dose or course of treatment of an IL-23 inhibitor is administered to the patient. Patients suffering from neuromyelitis optica can also be treated with an effective dose or course of treatment of an IL-17F inhibitor. Inhibitors include neutralizing antibodies specific for at least IL-17F or IL-23 protein, soluble IL-17F or IL-23 receptor; inactive forms of IL-17F or IL-23; and the like.

Clinical trials describing various therapeutic agents, appropriate dosage regimens, and the like for MS are as follows: O'Connor et al., A Phase II study of the safety and efficacy of teriflunomide in multiple sclerosis with relapses, Neurology, 2006 Mar. 28; 66(6):894-900; Kappos et al, A placebo-controlled trial of oral fingolimod in relapsing multiple sclerosis, N Engl J Med. 2010 Feb. 4; 362(5):387-401. Epub 2010 Jan. 20; Cohen et al, Oral fingolimod or intramuscular interferon for relapsing multiple sclerosis, N Engl J Med. 2010 Feb. 4; 362(5):402-15. Epub 2010 Jan. 20. All of these references are herein incorporated by reference.

In other embodiments, the effectiveness of β-IFN in a patient classified as a non-responder is enhanced by administration of an effective dose of γ-IFN. The γ-IFN can be co-formulated with an effective dose of β-IFN, or can be administered as a single agent that complements endogenous β-IFN.

In some embodiments the therapeutic agents are antibodies. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made in an immortalized B cell or hybridoma thereof, or can be made by recombinant DNA methods.

The monoclonal antibodies herein include hybrid and recombinant antibodies produced by splicing a variable (including hypervariable) domain of an anti-H5N1 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, $F(ab')_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antigen specific therapeutic methods include administration of an antigen or epitope specific therapeutic agent. One method to induce immune tolerance is tolerizing DNA vaccines (Garren et al. (2001) Immunity, 15:15-22; Robinson et al. (2003) Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of a targeted antigen in order to induce immune tolerance to the encoded epitopes. To enhance the ability of such plasmids to induce immune tolerance, the immunostimulatory CpG sequences (Krieg et al. (1998) Trends Microbiol. 6:23-27) can be reduced in number or completely removed from the plasmid vector. Additionally, immunoinhibitory GpG sequences can be added to the vector (see Ho et al. (2005) J. Immunology, 175:6226-34). Tolerizing DNA plasmids are delivered intramuscularly to induce immune tolerance to an antigen, thereby reducing T cell and autoantibody responses to reduce autoimmune destruction of the myelin sheath.

As an alternative, or in addition to DNA tolerization, specific peptides, altered peptides, or proteins can be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Al teration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Active ingredients in pharmaceutical compositions formulated for the treatment of various disorders are as described above. The active ingredient is present in a therapeutically effective amount, i.e., an amount sufficient when administered to substantially modulate the effect of the targeted protein or polypeptide to treat a disease or medical condition mediated thereby. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that can be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which are composed of the packaged active ingredient with a suppository base. Suitable suppository bases include natural or synthetic triglycerides or paraffin hydrocarbons. In addition, it is also possible to use gelatin rectal capsules, which are composed of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which can be present during the synthesis or purification process. Compositions for parental administration are also preferably sterile, substantially isotonic and made under GMP conditions.

The compositions can be administered in a single dose, or in multiple doses, usually multiple doses over a period of time, e.g. daily, every-other day, weekly, semi-weekly, monthly etc. for a period of time sufficient to reduce severity of the inflammatory disease, which can comprise 1, 2, 3, 4, 6, 10, or more doses.

Determining a therapeutically or prophylactically effective amount an agent can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of protein, as applicable. In a further embodiment, the effective amount contains between about 10 mg and about 50 mg of the nucleic acid or protein, as applicable. The effective dose will depend at least in part on the route of administration. The agents can be administered orally, in an aerosol spray; by injection, e.g. i.m., s.c., i.p., i.v., etc. In some embodiments, administration by other than i.v. can be preferred. The dose can be from about 0.1 µg/kg patient weight; about 1 µg/kg; about 10 µg/kg; to about 100 µg/kg.

The compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of compositions of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Treating, treatment, or therapy of a disease or disorder shall mean slowing, stopping or reversing the disease's progression by administration of treatment according to the present invention. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration of a composition to prevent the occurrence or onset of a disease or disorder or some or all of the symptoms of a disease or disorder or to lessen the likelihood of the onset of a disease or disorder.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

Example 1

TH1 and TH17 Pathways Determine Opposite Results of IFN-β Treatment of Experimental Autoimmune Encephalomyelitis and Relapsing Remitting Multiple Sclerosis Interferon-β is the major treatment for multiple sclerosis (MS). However, this treatment is not always effective. Here we see a striking congruence in outcome between responses to IFN-β in experimental autoimmune encephalomyelitis (EAE) and relapsing remitting MS. IFN-β is effective in reducing EAE induced by Th1 cells, but exacerbated disease induced by Th17. Effective treatment in Th1 EAE correlated with increased IL-10 in spleens. In Th17 disease, IL-10 was unchanged by treatment, though unexpectedly IFN-β still reduced IL-17 without benefit. Both inhibition of IL-17 and induction of IL-10 depended on IFN-γ. The absence of IFN-γ signaling resulted in ineffective IFN-β therapy in EAE. In RRMS, IFN-β non-responders had higher IL-17F in serum compared to responders. Non-responders had worse disease with more steroid usage and more relapses than responders. These results demonstrate that IFN-β is pro-inflammatory in Th17 induced EAE and high IL-17F in serum predict non-responsiveness to IFN-β in RRMS.

For more than a decade, MS and Experimental Autoimmune Encephalomyelitis (EAE), a collection of various animal models with many features of MS, were considered to be TH1 diseases. However, subsequent studies demonstrated that IFN-γ has a protective role in EAE, despite the fact that it worsens MS. This paradox provided a key impetus for the discovery of the TH17 lineage of effector cells from experiments in EAE. TH17 differentiation is strongly inhibited by IFN-γ and therefore with some logic, TH17 was promoted to the position of the major pathogenic T helper subset in autoimmune diseases like EAE and MS. However, recent data dispute the primacy of IL-17 in the pathogenesis of EAE. It is now accepted that TH1 and TH17 are both involved in the pathogenesis of EAE and perhaps relapsing remitting MS (Kroenke et al. J Exp Med 205, 1535-41 (2008); Stromnes et al. Nat Med 14, 337-42 (2008)).

There are many reported immunosuppressive effects of IFN-β. Several reports support the hypothesis that IFN-β reduces TH1 pathologies by blocking the pro-inflammatory properties of IFN-γ and IL-12, the hallmark TH1 cytokines. More recently, it has been shown that IFN-β inhibits the differentiation of TH17 cells. In addition to inhibiting inflammatory pathways, IFN-β treatment has been connected with an increase in regulatory cytokines, including IL-10, IL-27 and IL-4. Despite these associations with IFN-β inhibition of TH1 and TH17 and its role in enhancing immuno-regulatory cytokines, the mechanism underlying IFN-β therapy in MS is still unknown, and it remains unclear why some patients respond, while others do not.

Results

Figure 6:
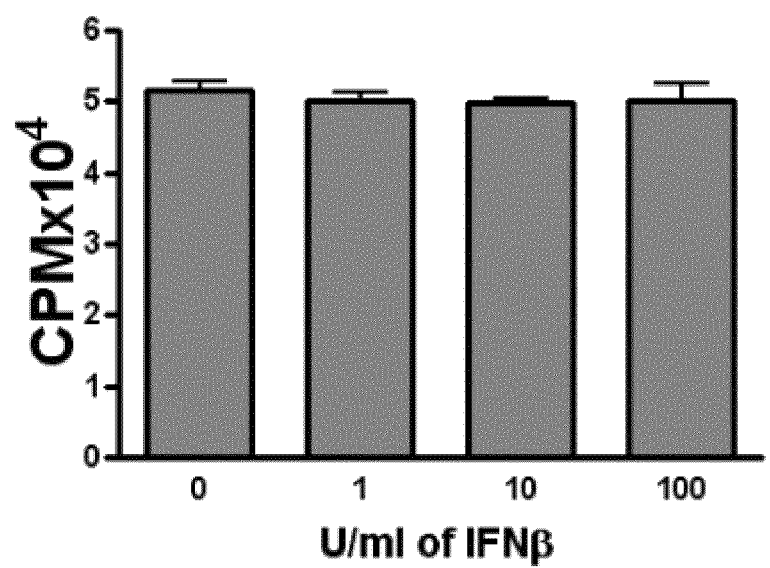
FIG. 6. IFN-β does not affect proliferation of CD4 T-cells. Spleen cells, depleted of CD8 cells, were stimulated with 1 μg/ml of anti-CD3 and treated IFN-β; proliferation was assessed by tritiated thymidine incorporation during the last 18 hrs of a 72 hr culture. Results are the mean±SD of triplicates.

IFN-β blocks the differentiation of Murine TH17 cells through STAT1 activation. It has been demonstrated that IFN-β can effect TH17 differentiation, however, the mechanism has not been defined. To address this question, we analyzed the effect of exogenous IFN-β on the differentiation of murine CD4 T-cells stimulated in the presence of IL-6, TGF-β and antigen presenting cells (APCs), conditions that favor TH17 differentiation. We observed that IFN-β significantly inhibited the generation of IL-17 expressing CD4 T-cells in TH17 conditions (FIG. 1a). This decrease in TH17 differentiation is not due to inhibition of T-cell proliferation, since IFN-β did not affect the proliferation in response to anti-CD3 stimulation (FIG. 6).

There are fundamental differences in the requirements for of IL-17 expression in naïve and effector/memory CD4 T-cells in mice. IL-23 has an important role in driving the inflammatory effects of TH17 cells by acting on effector/memory cells. However, naïve cells respond weakly to IL-23 and require IL-6 and TGF-β to produce large amounts of IL-17. We found that IFN-β decreased IL-17 production from naïve CD4 T-cells stimulated with either IL-6 and TGF-β in presence of APC's (FIG. 1b). Similarly, IFN-β attenuated IL-17 production in effector/memory cells stimulated with either IL-6 and TGF-β or IL-23 alone (FIG. 1b). These data demonstrate that IFN-β decreases IL-17 production at early and late stages of TH17 differentiation.

IFN-β can signal through a variety of JAK/STAT pathways, but the major signaling pathway activated by IFN-β is through ISGF3, a transcription factor complex containing STAT1, STAT2 and IRF9[31]. Moreover, the immunosuppressive effect of IFN-β has been attributed to the activation of ISGF3. We found that IFN-β failed to suppress TH17 differentiation of STAT1$^{-/-}$ CD4 T-cells, which implies that this effect is mediated by ISGF3 signaling (FIG. 1c).

Figure 7:
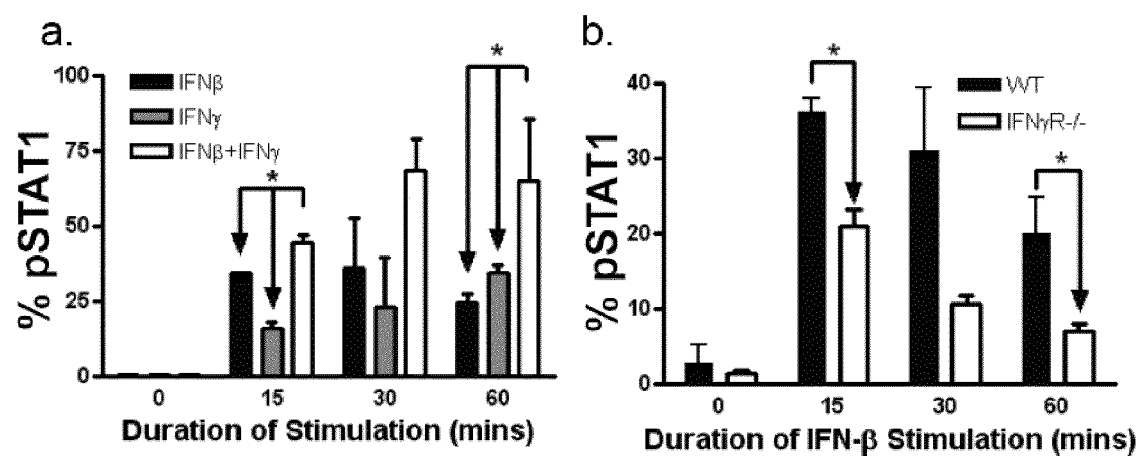
FIG. 7.a) Synergy of IFN-β and IFN-γ for STAT1 activation. Spleen cells C57BL/6 were stimulated with IFN-β or IFN-γ or both for 0, 15, 30 and 60 mins and phosphorylation of STAT1 in CD4 T-cells was assessed by flow cytometry. b) IFN-β requires IFN-γ for optimal STAT1 signaling. C57BL/6 and IFNγR−/−spleen cells were stimulated with IFN-β 0, 15, 30 and 60 mins and phosphorylation of STAT1 in CD4 T-cells was assessed by flow cytometry.

IFN-β requires IFN-γ to inhibit Murine TH17 differentiation. Studies have demonstrated that there is a cross-talk between the IFN-β and IFN-γ signaling pathways. For instance, IFN-γ has been shown to amplify the IFN-β mediated anti-viral response in melanoma cells by increasing the expression of STAT1 and STAT2. Nevertheless, IFN-γ dependent IFN-β signaling has not been elucidated in CD4 T-cells. We, therefore, assessed the synergistic effects of IFN-β and IFN-γ to activate STAT1. We found that IFN-β or IFN-γ alone could sufficiently induce the activation of STAT1 in CD4 cells. However, STAT1 activity was increased and prolonged when both IFN-β and IFN-γ were used together (FIG. 7a) compared to using either cytokine alone. In addition, we compared the ability of IFN-β to activate STAT1 in CD4 T-cells from WT mice and IFN-γR$^{-/-}$ mice. Compared to WT, the IFNγR$^{-/-}$ CD4 T-cells had significantly reduced intensity and duration of STAT1 phosphorylation (FIG. 7b). These data indicate that optimal activation of STAT1 by IFN-β in T-cells requires IFN-γ signaling.

Since STAT1 was required for IFN-β to attenuate IL-17 expression and we found that IFN-γ is required for optimal IFN-β activation of STAT1, we hypothesized that IFN-β requires IFN-γ signaling to inhibit the production of IL-17 in CD4 T-cells. To test this prediction, we examined the effect of IFN-β on CD4 T-cells when stimulated in IL-6 and TGF-β along with APC's and in the presence and absence of neutralizing IFN-γ antibody. Without neutralization of IFN-γ, IFN-β decreased the frequency of IL-17 expressing T-cells by 60% (FIG. 1d). When anti-IFN-γ was added to the cultures, the frequency of IL-17$^+$ CD4 cells increased, which was likely due to the inhibitory effects of IFN-γ on TH17. However, IFN-β inhibition of IL-17 was less effective when IFN-γ was neutralized, where production IL-17 was inhibited by only by only 24% (FIG. 1d). Two other cytokines have been implicated in the inhibition of TH17 differentiation, IL-10 and IL-27. In our culture system, both neutralization of IL-10 or IL-27 did not affect the ability of IFN-β to inhibit IL-17 expression (FIG. 1d).

Figure 8:
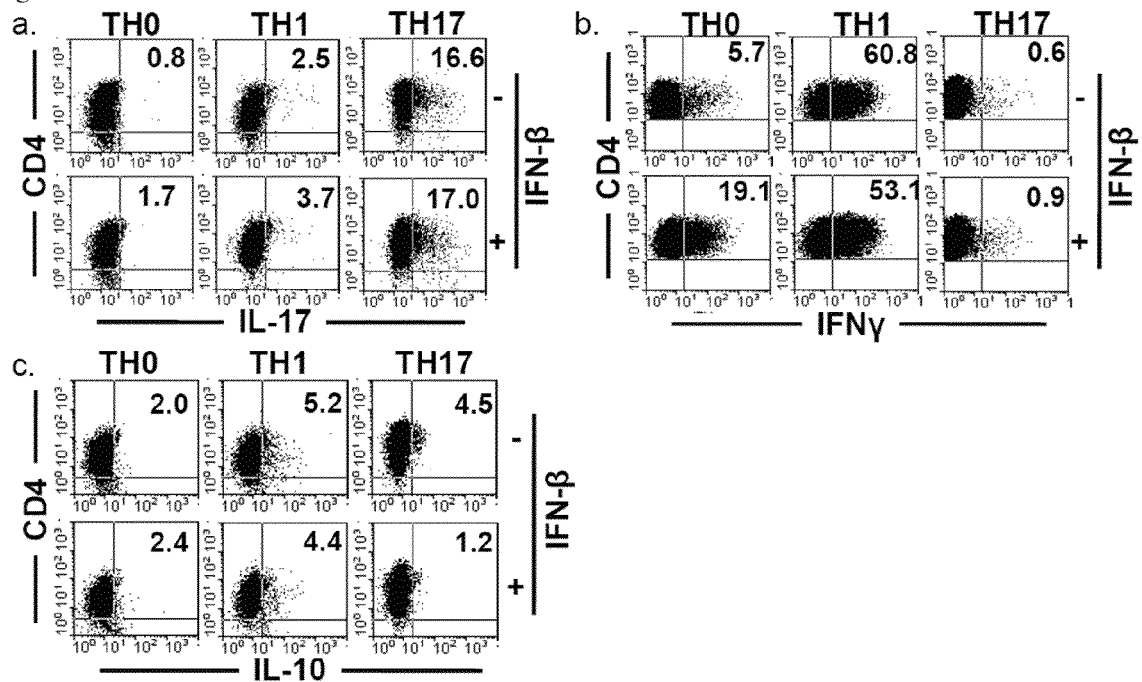
FIG. 8: Direct effect of IFN-β CD4 T-cells. Purified CD4 T-cells were stimulated with plate-bound anti-CD3 and anti-CD28 in non-polarizing, TH1 and TH17 conditions in the presence or absence of IFN-β. a) IL-17, b) IFN-γ and c) IL-10 production in CD4 cells were assessed by flow cytometry.

In the culture conditions described above, the synergistic effects of IFN-β and IFN-γ may be suppressing the production of IL-17 from CD4 T-cells by directly acting on T-cells or by acting upon APCs or other accessory cells. We found that IFN-β inhibited IL-17 in WT CD4 cells cultured with WT APCs or IFNγR$^{-/-}$ APC (FIG. 1e). In contrast IL-17 was not inhibited in IFNγR$^{-/-}$ CD4 T-cells in when cultured with either WT or IFNγR$^{-/-}$ APCs (FIG. 1e). In addition, we found IFN-β alone was insufficient to inhibit IL-17 production in purified naïve CD4 cells (FIG. 8a). We speculated that the inhibition of TH17 differentiation required the synergistic effects of IFN-β and IFN-γ. Indeed, we found that IFN-β or IFN-γ alone could not attenuate IL-17 production (FIG. 1f); however, when IFN-β and IFN-γ were used together, IL-17 production was reduced significantly (FIG. 1f). In sum, these data demonstrates that the cooperative signaling of IFN-β and IFN-γ directly affects murine CD4 T-cells and inhibits TH17 differentiation.

Effects of IFN-β on Murine TH1 differentiation. Reports have demonstrated that type 1 interferon can induce IFN-γ production in CD4 cells. We confirmed these previous findings. In non polarizing conditions, IFN-β induces the expression of IFN-γ in CD4 cells in the presence (FIG. 2a) or the absence in APC's (FIG. 8b). However, in TH1 or TH17 polarizing conditions IFN-β has no significant effect on IFN-γ production.

Figure 2:
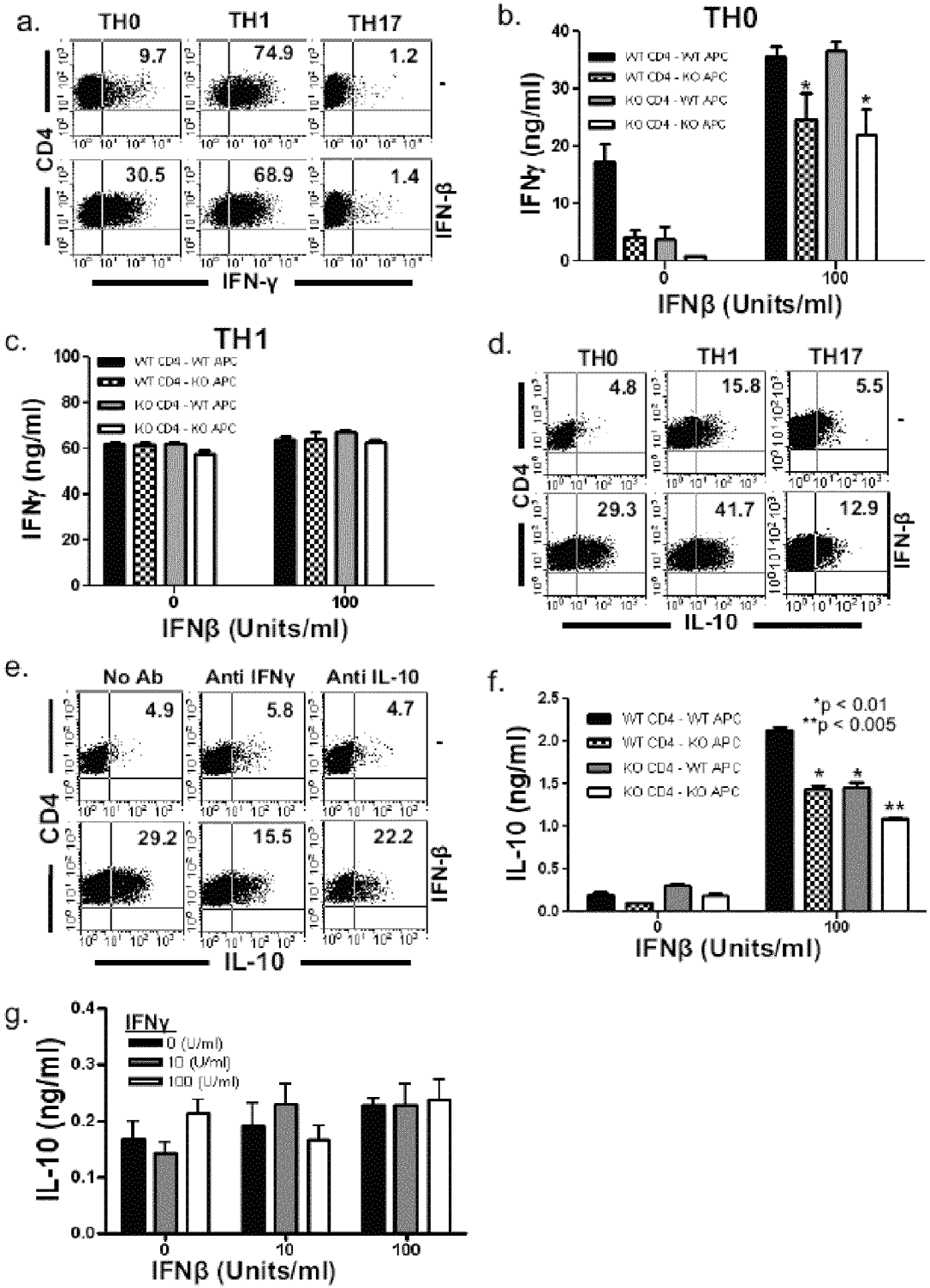
FIG. 2. (A-C) Effect of IFN-β on murine TH1 differentiation. A) Spleen cells, depleted of CD8 T-cells, were cultured with and without IFN-β (100 U/ml) in TH0 (non-polarizing), TH1 (IL-12) and TH17 (TGFβ and IL-6) conditions. CD4 gated cells were analyzed for IFN-γ production by flow cytometry. B) IFN-β requires IFN-γ signaling in CD4 T-cells to induce IFN-γ production in non-polarizing conditions. Purified WT or IFNγR$^{-/-}$ CD4 T-cells were stimulated in nonpolarizing conditions with APCs from WT or IFNγR$^{-/-}$ in the presence or absence of IFN-β. IFN-γ was assessed by ELISA. C) IFN-β and IFN-γ signaling have no effect on TH1 differentiation. Purified WT or IFNγR$^{-/-}$ CD4 T-cells were stimulated in TH1 conditions with APCs from WT or IFNγR$^{-/-}$ in the presence or absence of IFN-β. IFN-γ was assessed by ELISA. (D-G) Effect of IFN-β on IL-10 production during murine TH differentiation. D) IFN-β induces IL-10 in murine CD4 T-cells. CD8 depleted spleen cells were stimulated with or without IFN-β in TH0 (non-polarizing), TH1 (IL-12), and TH17 (TGFβ/IL-6) conditions and IL-10 expression in CD4 T-cells was analyzed by flow cytometry. E) IFN-γ signaling is necessary for optimal induction of IL-10 in murine CD4 T-cells by IFN-β. CD8 depleted spleen cells were stimulated with or without IFN-β in TH0 (non-polarizing) conditions in the presence or absence of anti-IFN-γ or anti-IL-10. F) IFN-β requires IFN-γ signaling in murine CD4 T-cells and APCs to induce IL-10. Purified WT or IFNγR$^{-/-}$ T-cells were polarized in TH17 polarizing conditions with WT or IFNγR$^{-/-}$ in the presence or absence of IFN-β and IL-10 was assessed by ELISA. G) IFN-β does not directly induce IL-10 in murine CD4 T-cells. Purified CD4 T-cells were stimulated with plate-bound anti-CD3 and anti-CD28 in non polarizing conditions in the presence or absence of IFN-β.

We next examined cooperative effects IFN-β and IFN-γ have on TH1 differentiation. We found that in non polarizing conditions, IFN-β induced the production of IFN-γ equally in WT and IFN-γR$^{-/-}$ CD4 cells cultured with WT APCs (FIG. 2b), but, IFNγ was impaired when CD4 cells were cultured with IFNγR$^{-/-}$ APCs (FIG. 2b). During TH1 polarization, IFN-γ production was not affected by IFN-β or IFN-γ signaling (FIG. 2c).

Figure 9:
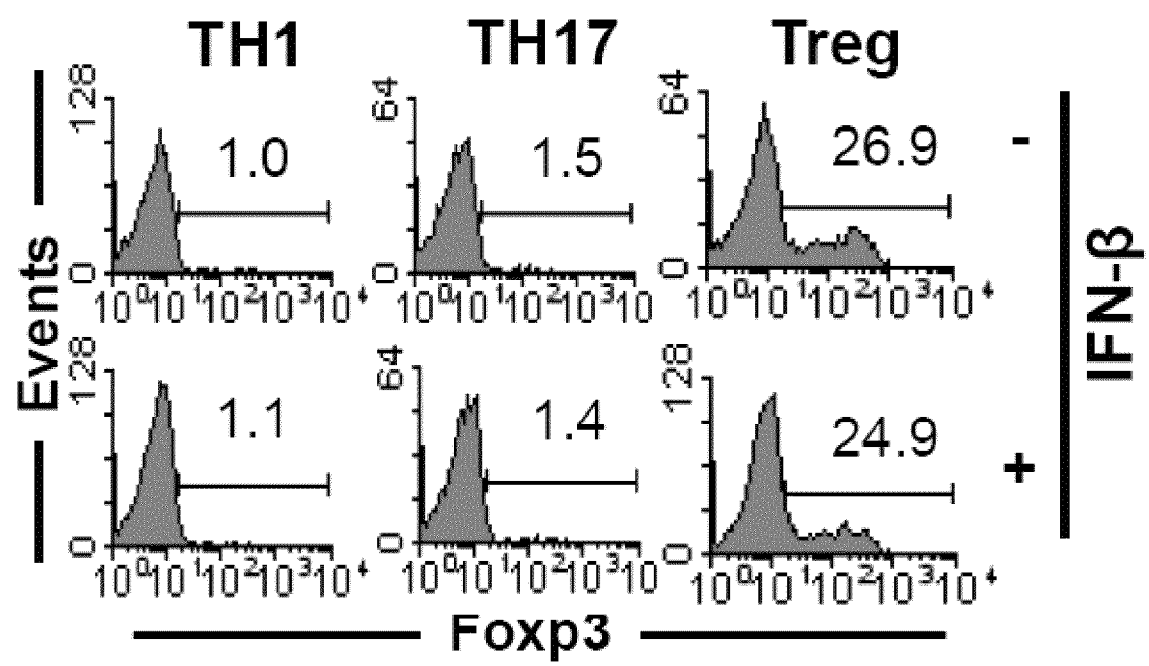
FIG. 9. IFN-β does not affect the differentiation of Foxp3+ T-regs. CD8 depleted spleen cells stimulated with or without IFN-β in TH1 (IL-12), TH17 (TGFβ/IL-6) and Treg (TGFβ) conditions and percentage of CD4+ FoxP3+ cells was assessed by flow cytometry.

IFN-β does not alter Murine TH17 differentiation to induce T-regs. TH17 cells are highly inflammatory. In order to maintain immune tolerance, the development of TH17 cells is closely linked to regulatory T-cells. TGF-β is a key factor in the differentiation of inducible FoxP3$^+$ T-reg cells; however in the context of pro-inflammatory cytokines, most notably IL-6, TGF-β induces the differentiation of the TH17. Therefore, we explored the possibility that while IFN-β inhibits TH17 differentiation, it would promote the Foxp3$^+$ T-reg development. However, we found that IFN-β does not induce the development Foxp3$^+$ T-reg cells in the TH17 polarizing conditions (FIG. 9). In fact, IFN-β had no effect on their development even in cultures with TGF-β in the absence of IL-6 (FIG. 9).

Figure 10:
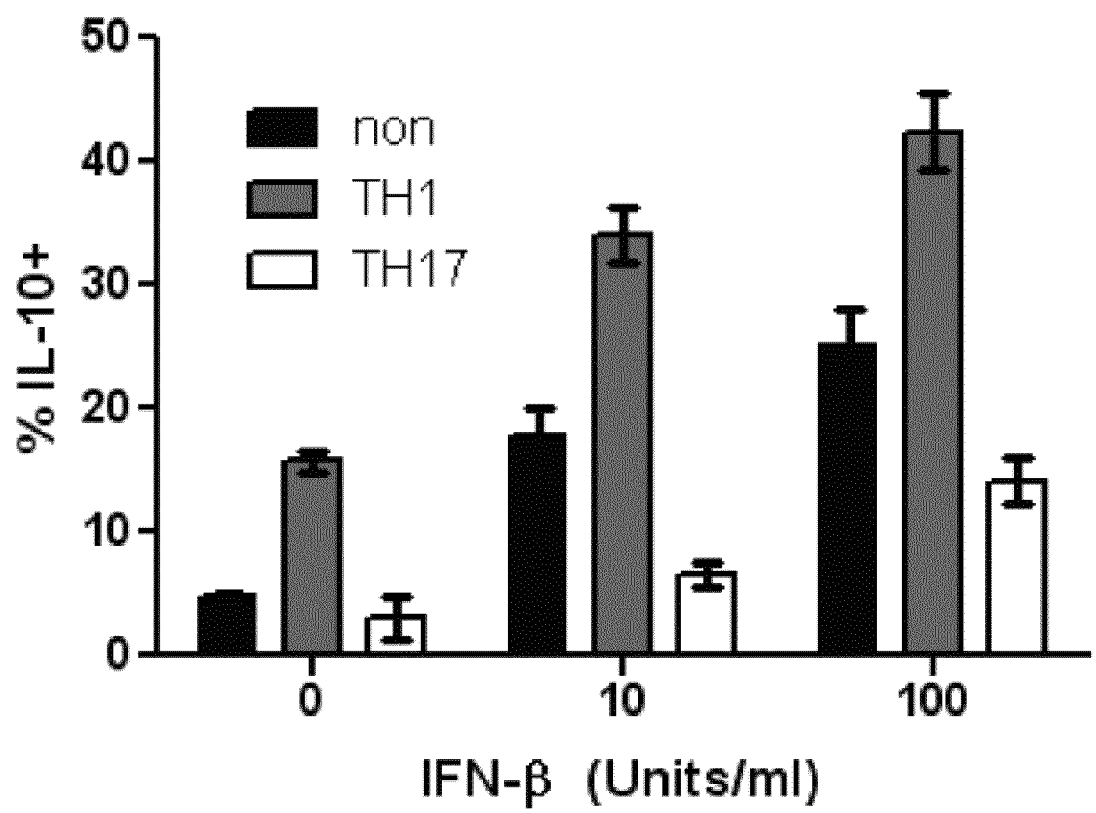
FIG. 10. Frequency of IL-10 producing CD4 T-cells after IFN-β stimulation of CD8 depleted in spleens cells cultured with non-polarizing, TH1 and TH17 polarization. Data is the mean±standard deviation of 3 independent flow cytometry experiments.

IFN-β increases IL-10 in Murine CD4 cells. MS patients who respond to IFN-β have increased serum levels of IL-10 after treatment. Therefore, we investigated the possibility that IFN-β may up-regulate IL-10 during murine CD4 T-cell differentiation. To address this, we analyzed the effect IFN-β has on IL-10 production by CD4 T-cells stimulated in the presence of APCs in non-polarizing, TH1 and TH17 conditions. We found that IFN-β did increase IL-10 in all culture conditions (FIG. 2d). However, both the TH1 and non-polarizing culture conditions showed significantly higher IL-10 levels after IFN-β compared to the TH17 condition (FIG. 2d, FIG. 10).

Figure 11:
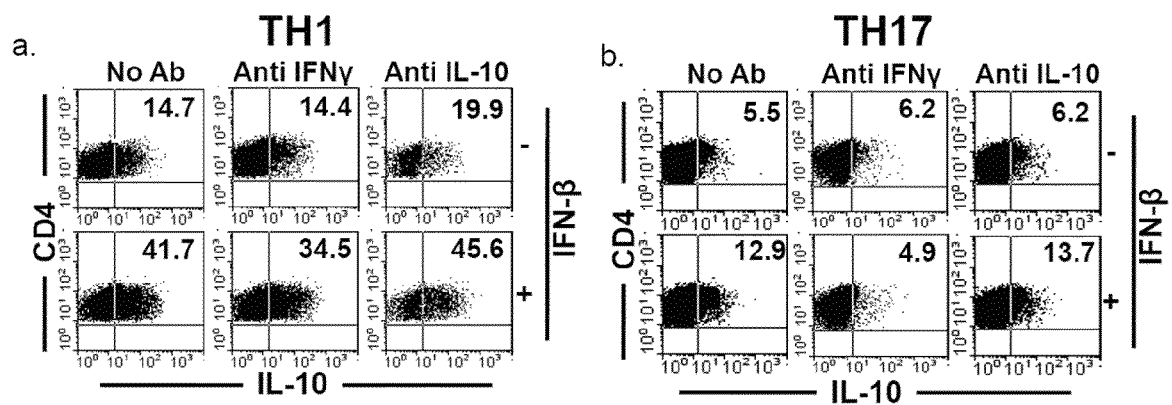
FIG. 11. Effect of inhibiting IFN-γ or IL-10 signaling during the induction of IL-10 by IFN-β in a) TH1 conditions and b) TH17 conditions. CD8 depleted spleen cells were stimulated with or without IFN-β in TH1 (IL-12) or TH17 (TGFβ/IL-6) conditions in the presence or absence of anti-IFN-γ or anti-IL-10.

The increase of IL-10 correlated to the amount of IFN-γ produced in each condition (FIG. 2a), suggesting that IFN-β can work synergistically with IFN-γ to up-regulate IL-10. When IFN-γ was neutralized in non-polarizing (FIG. 2e), TH1 (FIG. 11a), and TH17 (FIG. 11b) culture conditions, the ability of IFN-β to induce IL-10 by CD4 T-cells was impaired. Furthermore, IL-10 production was impaired in cultures where IFN-γ signaling was disrupted in either CD4 T-cells or APCs, demonstrating that IL-10 induction by IFN-β requires IFN-γ signaling in CD4 T-cells and APCs (FIG. 2f). We also considered that the up-regulation of IL-10 could provoke an autocrine loop, promoting the expression of more IL-10 in CD4 T-cells. We found that neutralizing IL-10 in these cultures had no effect on expression of IL-10 (FIG. 2e and FIG. 11).

IFN-β indirectly induces IL-10 in Murine T-cells through induction of IL-27 in APCs. Because we found that IFN-β with IFN-γ directly inhibits the production of IL-17 in CD4 cells, we hypothesized that there is a similar effect on IL-10. To address this, we tested the effect IFN-β has on purified naïve CD4 cells in non-polarizing, TH1 or TH17 conditions. We found that IFN-β alone had no effect on IL-10 production in these conditions (FIG. 8c) even from the non polarizing and TH1 polarizing condition that do produce significant amounts of IFN-γ (FIG. 8b). Furthermore we found that the addition of IFN-γ with IFN-β did not significantly increase IL-10 production from these CD4 cells (FIG. 2g).

Figure 12:
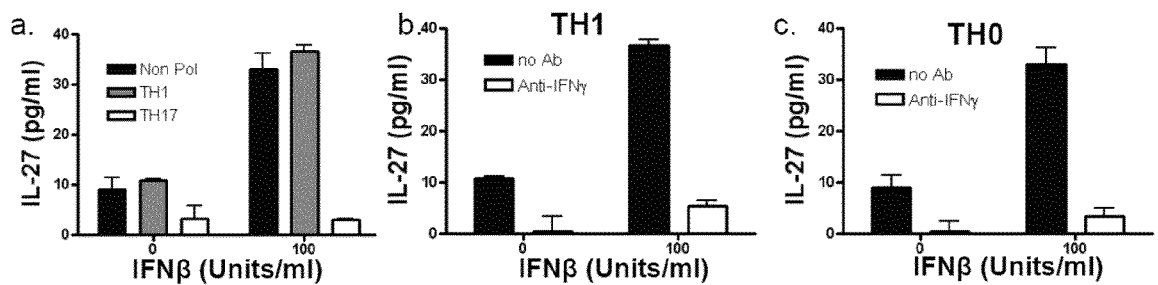
FIG. 12.a) IFN-β induces IL-27 in non-polarizing and TH1 conditions but not TH17 conditions. CD8 depleted spleen cells were stimulated with or without IFN-β in TH0 (non-polarizing), TH1 (IL-12), and TH17 (TGFβ/IL-6) conditions and IL-27 was analyzed by ELISA. IFN-β requires IFN-γ to induce IL-27 in non-polarizing conditions (b) and TH1 conditions (c). CD8 depleted spleen cells were stimulated with or without IFN-β in TH0 (non-polarizing), TH1 (IL-12) conditions in the presence or absence of anti-IFN-γ and IL-27 was analyzed by ELISA. Results for these experiments are the mean±SD of triplicates.

IL-27 is a key cytokine produced by dendritic cells and other APC's that induces IL-10 in CD4 cells. Furthermore, recent data has suggested that IFN-β induces DC's to express IL-27. Therefore, we analyzed the effect IFN-β has on the levels of IL-27 in non-polarizing, TH1 and TH17 culture conditions in the presence of APC's. We found that in both non-polarizing and TH1 culture conditions IL-27 was significantly up-regulated by IFN-β, whereas in TH17 conditions IL-27 was not elevated (FIG. 12a). This induction of IL-27 by IFN-β also required IFN-γ, since neutralizing IFN-γ inhibited IL-27 production (FIG. 12b, c).

Figure 13:
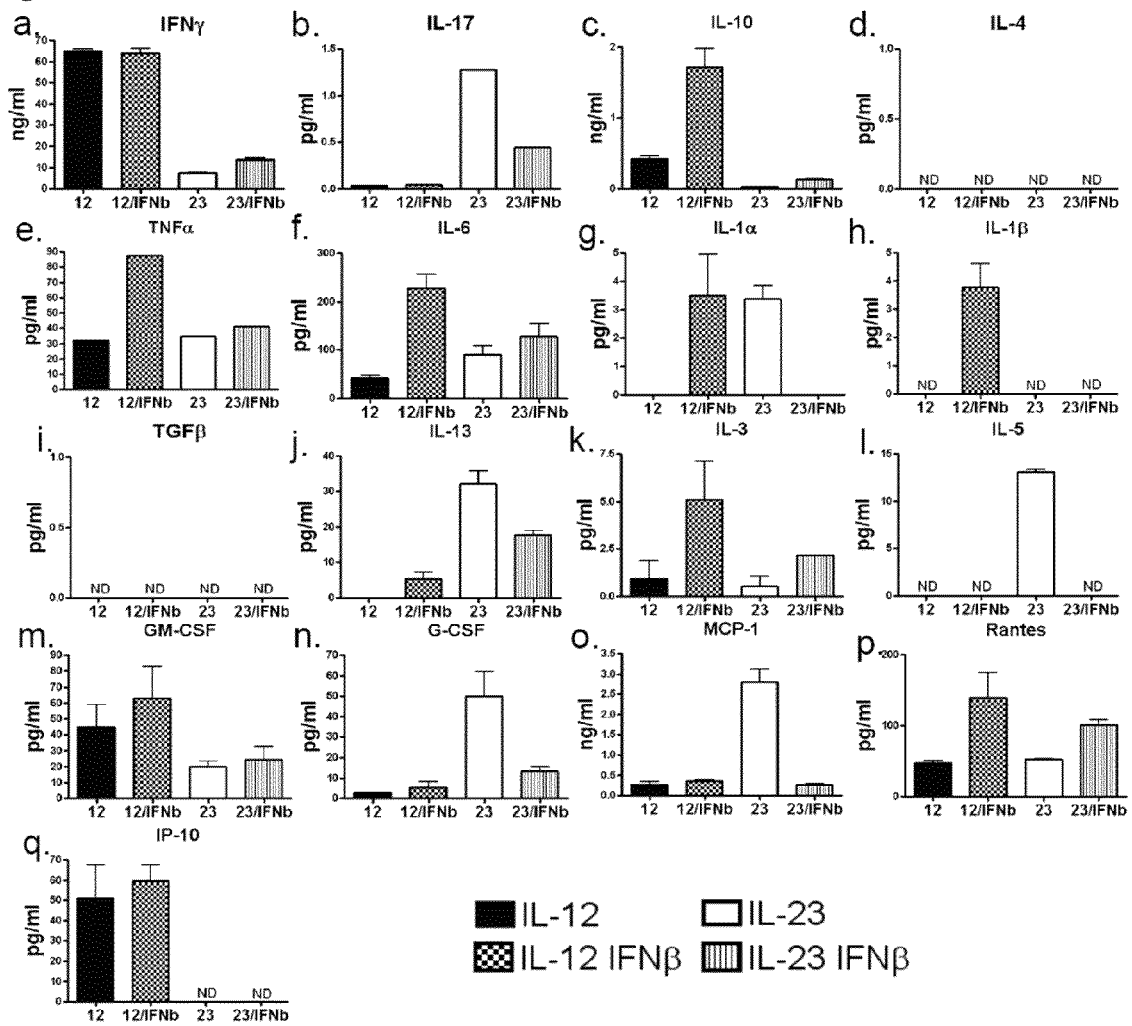
FIG. 13. (a-q) Effect of IFN-β on Chemokine/Cytokine profiles in antigen specific TH1 (IL-12) and TH17 (IL-23) differentiation. Lymph nodes from MOGp35-55 immunized mice were re-stimulated in MOGp35-55 for 3 days with IL-12 or IL-23 in the presence or absence of IFN-β. Chemokines and cytokines were assessed by Luminex multiplex analysis or ELISA.

Effects of IFN-β during antigen-driven Murine TH1 and TH17 differentiation. To test the effects of IFN-β in an antigen specific TH polarization, we assessed the effects of IFN-β during TH1 and TH17 differentiation during MOG-peptide re-stimulation. LN cells from MOG immunized mice were re-stimulated with MOG peptide and either IL-12 or IL-23, to polarize cells to TH1 and TH17 respectively, and cytokine and chemokine in culture supernatants were quantified by Luminex or ELISA (FIG. 13).

In agreement with our previous data, we found that IFN-β significantly reduced IL-17 production in TH17 cultures (FIG. 13b); greatly induced IL-10 production in TH1 cells but not in TH17 (FIG. 13c); and had no significant effect on IFN-γ production (FIG. 13a). In addition, IFN-β did not up-regulate IL-4 (FIG. 13d) and TGF-β (FIG. 13i), two cytokines that have been implicated in regulating autoimmunity. Another remarkable result was that in TH1 conditions, IFN-β induced TNF, IL-6, IL-1α and IL-1β (FIG. 13e-h); which are most usually considered highly pro-inflammatory cytokines, though in multiple sclerosis their role, especially TNF, can be protective. Another effect of interest was that in TH17 differentiation IFN-β inhibited expression of the chemokines G-CSF and MIP-1 (FIG. 13n,o).

Figure 3:
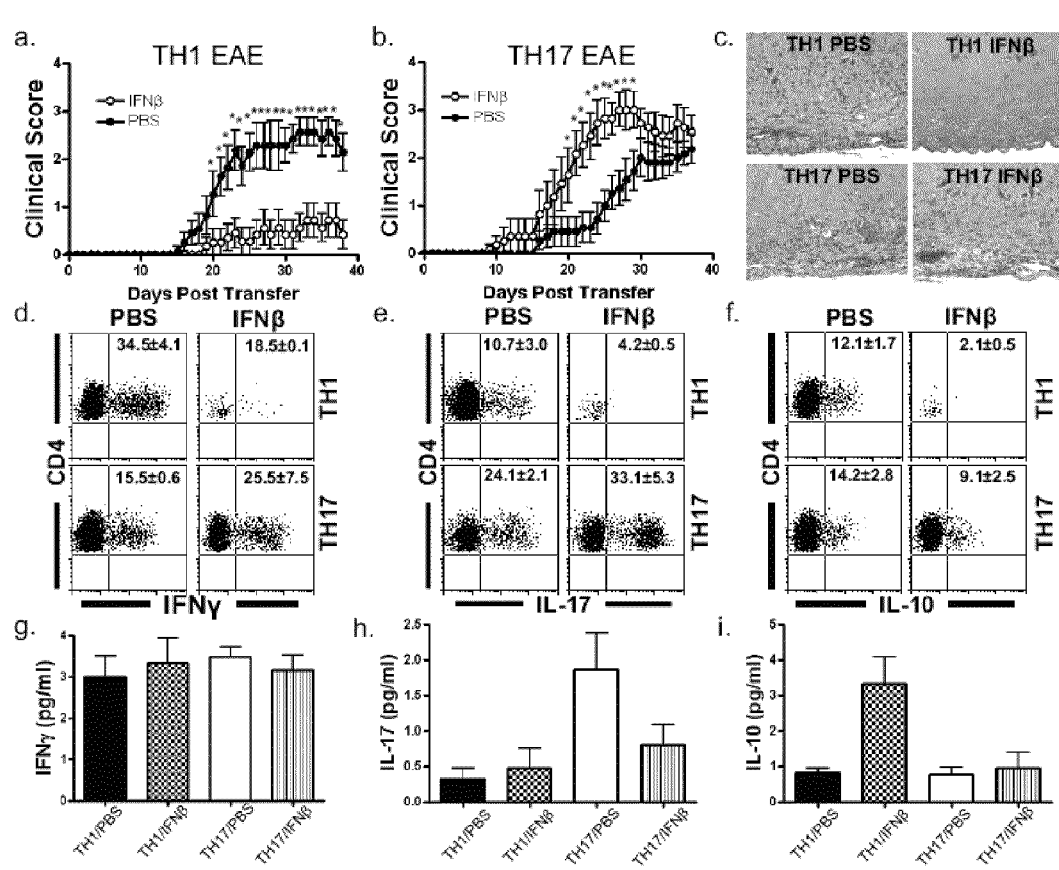
FIG. 3. IFN-β treatment blocks TH1 induced EAE but exacerbates TH17 induced EAE. (A and B) Clinical scores from mice with passive EAE induced by adoptive transfer of (A) TH1 and (B) TH17 cells that were treated with rmIFN-β or PBS every second day from day 0 to 10 post transfer (N=9 to 11 mice per group). *P<0.05. C) Histology of spinal cord sections from TH1 and TH17 induced EAE treated with IFN-β or PBS. Section of spinal cord were obtained 45 days after transfer and stained with H&E and Luxol fast blue. (D-F) Frequency of CD4$^+$ lymphocytes expressing IFN-γ (D), IL-17 (E) and IL-10 (F) in the spinal cords 45 day post transfer. The mean percentage±standard deviation (N=3 experiments) of cytokine positive cells is given. Each experiment is a pool from 2-3 mice per group. (G-I) Concentration of IFN-γ (G), IL-17 (H) and IL-10 (I) from supernatants of MOGp35-55 stimulated spleens taken from mice 45 days post transfer. Data represent mean and standard deviation of 3-4 mice per group.
Figure 14:
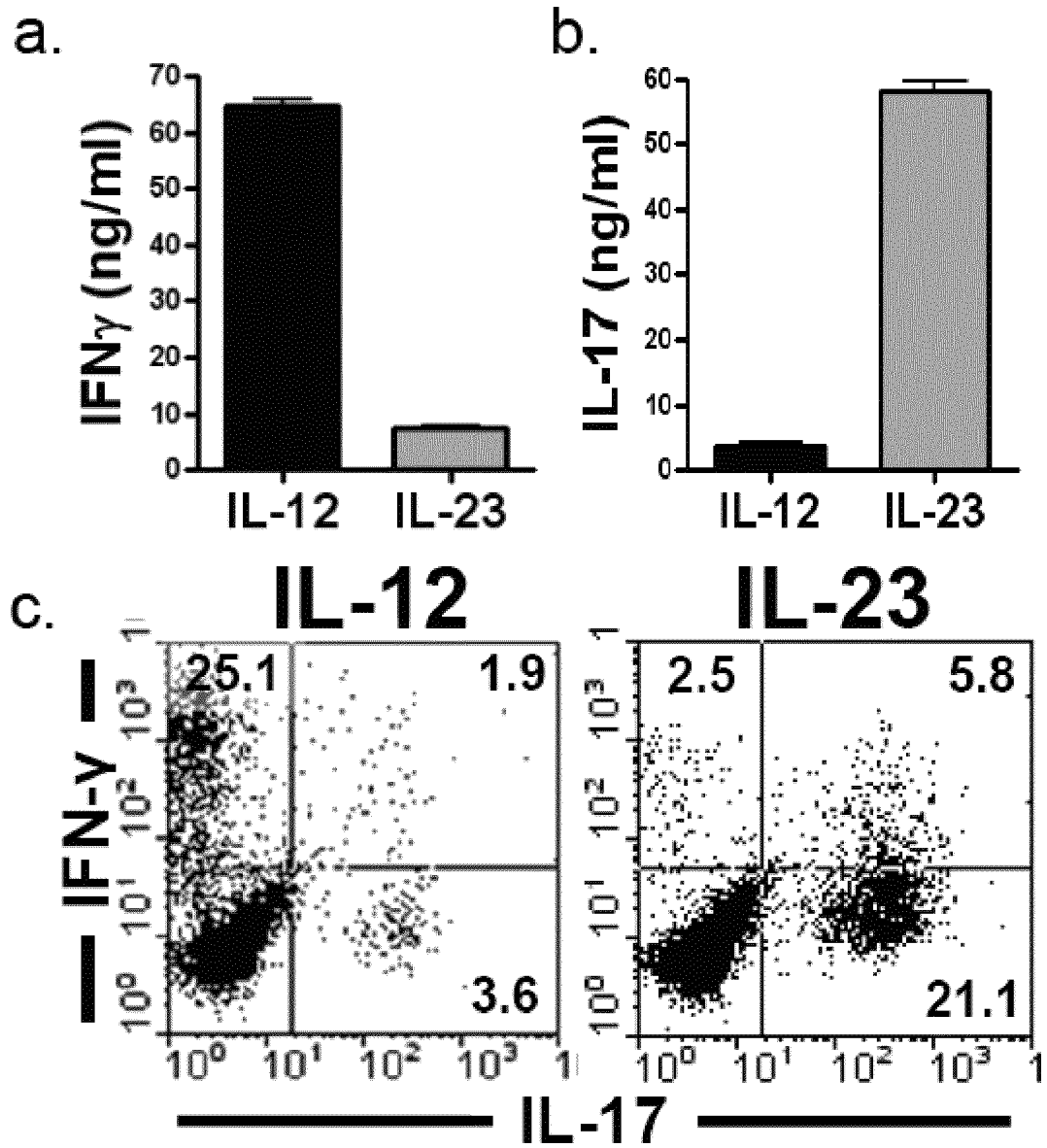
FIG. 14. IFN-γ and IL-17 production from TH1 and TH17 cells prior to adoptive transfer. Lymph nodes and spleen from MOGp35-55 immunized mice were re-stimulated in MOGp35-55 for 3 days with IL-12 or IL-23 and cytokines produced by CD4 T-cells were assessed by (a and b) ELISA and (c) intracellular flow cytometry.
Figure 15:
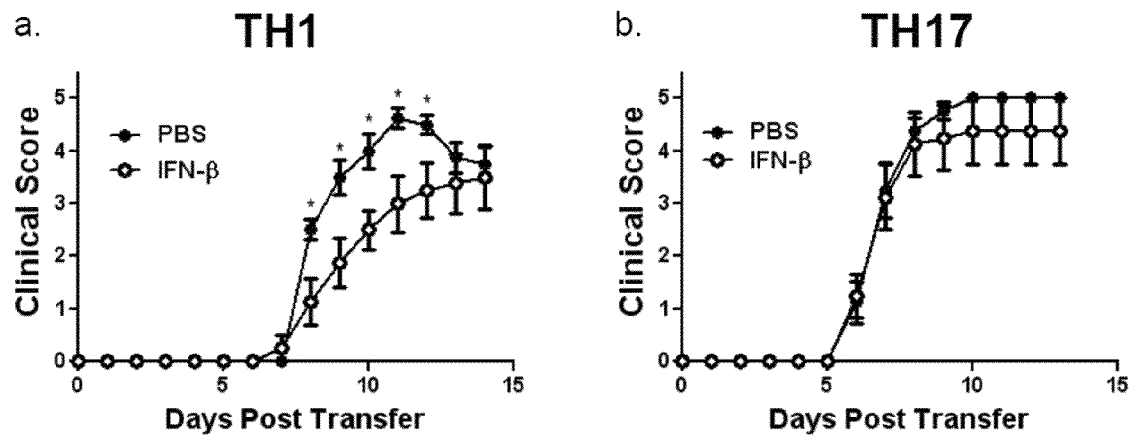
FIG. 15. Effect of IFN-β treatment in TH1 and TH17 induced EAE in SJL mice. Clinical scores from mice with passive EAE induced by adoptive transfer of (a) TH1 and (b) TH17 cells that were treated with rmIFN-β or PBS every second day from day 0 to 10 post transfer (N=6 mice per group). *P<0.05.

IFN-β treatment is effective in reducing severity in TH1 induced EAE but exacerbates disease in TH17 induced EAE. Our in vitro experiments demonstrate that IFN-β has anti-inflammatory effects in the differentiation TH1 and TH17 lineages. This led us to question whether IFN-β would be effective in treating EAE induced by TH1 or TH17 cells. For this, we re-stimulated LN and spleen cells from MOG immunized C57BL/6 mice in the presence of IL-12 (TH1) or IL-23 (TH17) and adoptively transferred these cells into healthy C57BL/6 recipient mice to induce EAE. The effector function of the TH1 and TH17 donor cells was assessed by ELISA and flow cytometry prior to transfer (FIG. 14). The recipient mice were then treated with IFN-β or PBS every second day from day 0-10 post transfer of cells. We found considerable difference in the effect of IFN-β treatment on the TH1 and TH17 induced EAE. IFN-β treatment significantly attenuated the progression of EAE symptoms in TH1 induced EAE (FIG. 3a), but in striking contrast, symptoms of TH17 induced EAE were exacerbated by IFN-β treatment (FIG. 3b). This was not a strain dependent phenomenon, specific for just C57BL/6. IFN-β treatment had a similar effect in the SJL/PLP EAE transfer model (FIG. 15a,b) In accordance with the clinical course of EAE, histological analysis demonstrated that IFN-β treatment blocked inflammation in the spinal cords of mice with TH1 EAE but not in TH17 EAE (FIG. 3c).

We have shown that IFN-β alters the differentiation of TH1 and TH17 cells in vitro. Therefore, we assessed the amount of IFN-γ, IL-17, and IL-10 produced in the CNS and spleens at day 45 post transfer. We found that the frequency of CD4 T-cells producing IL-17 and IFN-γ found in the spinal cord were decreased after IFN-β treatment of TH1 EAE (FIG. 3d,e), but in TH17 EAE both TH1 and TH17 cells were elevated with IFN-β (FIG. 3d,e). IL-10, on the other hand, was decreased in the spinal cords of either the TH1 or TH17 disease after IFN-β treatment (FIG. 3f).

Next, we assessed the effects IFN-β treatment has on T-cell function in TH1 and TH17 EAE in peripheral lymphoid organs. At day 45 post transfer, we re-stimulated spleen cells with MOG-peptide and assessed cytokine production from spleens by ELISA. In both TH1 and TH17 disease, IFN-γ production was not changed with IFN-β treatment (FIG. 3g). However, IFN-β did have differential effects on IL-17 and IL-10 in these disease models. In TH1 EAE, levels of IL-17 produced by spleens were low and treatment with IFN-β did not affect the production of this cytokine (FIG. 3h). However, in TH17 EAE, spleens produced higher amounts of IL-17 compared to TH1 EAE, and surprisingly, IL-17 was significantly reduced in the TH17 mice treated with IFN-β (FIG. 3h). In contrast, IL-10 production in spleens from TH1 diseases was significantly elevated by IFN-β (FIG. 3i); but in TH17 EAE, IL-10 remained very low after treatment (FIG. 3i).

Figure 4:
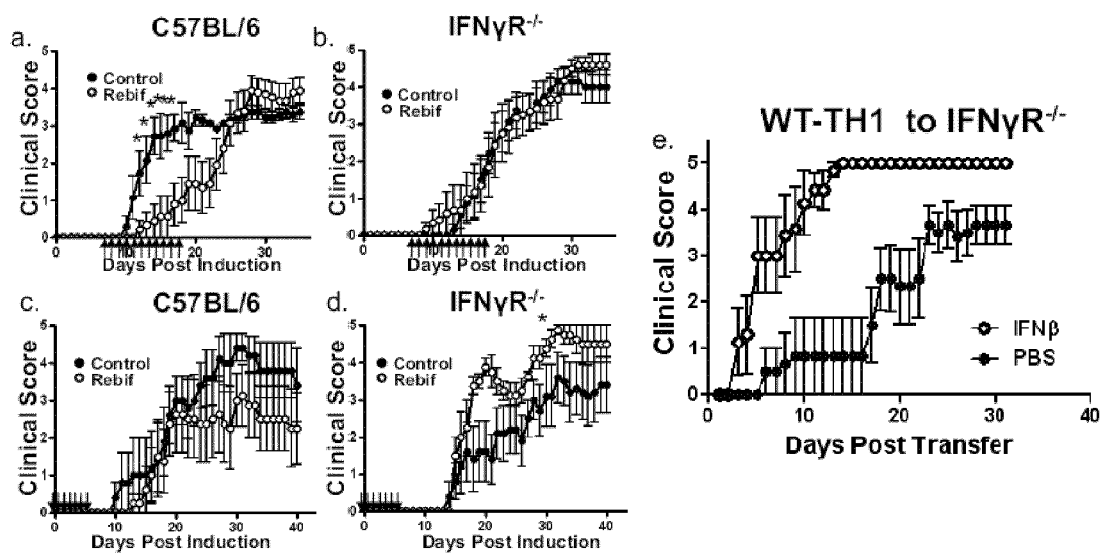
FIG. 4. IFN-β treatment requires IFN-γ signaling to suppress EAE symptoms. (A and B) Clinical scores from active EAE in (A) C57BL/6 and (B) IFNγR$^{-/-}$ mice that were treated with Rebif or PBS daily from day 7 to day 17 post EAE induction (N=7 to 9 mice per group). (C and D) Clinical scores from active EAE in (C) C57BL/6 and (D) IFNγR$^{-/-}$ mice treated daily with rmIFN-β of PBS from day 10 to day 17 post EAE induction (N=4 to 5 mice per group). E) Clinical scores from IFNγR$^{-/-}$ mice with passive EAE induced by adoptive transfer of WT TH1 and treated with IFN-β or PBS every second day from day 0 to 10 post transfer (N=6). Treatment doses indicated with arrows. *P<0.05.
Figure 16:
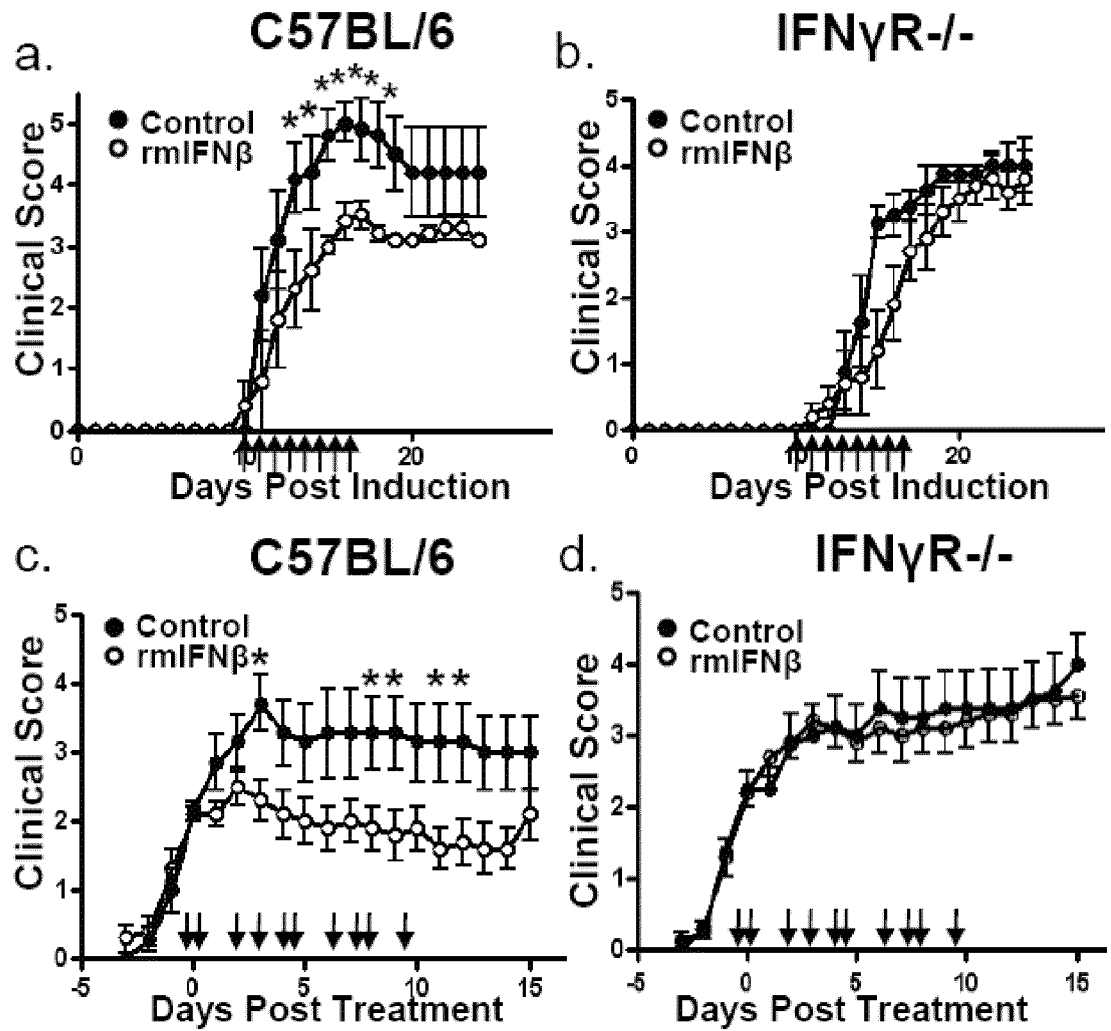
FIG. 16. (a and b) Clinical scores from (a) C57BL/6 and (b) IFNγR−/− mice treated daily with rmIFN-β of PBS from day 10 to day 17 post EAE induction (N=4 to 5 mice per group). (c and d) Clinical scores from (c) C57BL/6 and (d) IFNγR−/− mice treated daily for 10 days with rmIFN-β or PBS beginning at disease score of 2 or 3 (N=6 to 9 mice per group). Treatment doses indicated with arrows. *P<0.05.

IFN-β treatment requires IFN-γ signaling to suppress EAE. IFN-β treatment is highly effective in TH1 induced EAE, and IFN-β requires IFN-γ to suppress IL-17 and induce IL-10 in cultures; we therefore speculated that IFN-β treatment would require IFN-γ to effectively treat active EAE. To explore this hypothesis, we tested the efficacy of IFN-β treatment of $MOG_{35-55}$ induced EAE in C57BL/6 mice and IFNγR$^{-/-}$ mice. Daily injections of Rebif, one of the popular forms of IFN-β used to treat RRMS, beginning seven days after EAE induction, significantly delayed the onset and reduced the severity of EAE symptoms in the C57BL/6 mice (FIG. 4a). This protective effect of IFN-β treatment was transient, since the mice developed severe symptoms after the withdrawal of treatment, on day 18 post induction of disease. In contrast to the C57BL/6 mice, IFN-β treatment had no effect on the development of disease in IFNγR$^{-/-}$ mice (FIG. 4b). Similar to Rebif treatment, recombinant mouse IFN-β attenuated EAE in C57BL/6 mice (FIG. 16a) but not in IFNγR$^{-/-}$ mice (FIG. 16b).

In another regimen, modeling disease prevention, mice were treated daily with Rebif from day 0 to day 6 post induction of EAE. With this regimen, it was striking that the IFNγR$^{-/-}$ mice had a trend of more severe symptoms when treated with IFN-β compared to controls (FIG. 5d); similar to the effect IFN-β had on TH17 induced EAE (FIG. 3b). In contrast, IFN-β treatment with this regimen in C57BL/6 mice was slightly protective (FIG. 4c).

Next we tested whether IFN-β treatment can reverse the progression of EAE after the onset of symptoms. We treated C57BL/6 and IFNγR$^{-/-}$ mice with rmIFN-β at the clinical score of 2 or 3. We found that rmIFN-β treatment attenuated the progression of symptoms in C57BL/6 mice scores compared to PBS treated mice (FIG. 16c). In accordance with the other regimens, IFN-β did not attenuate the disease in the IFNγR$^{-/-}$ mice (FIG. 16d).

Figure 17:
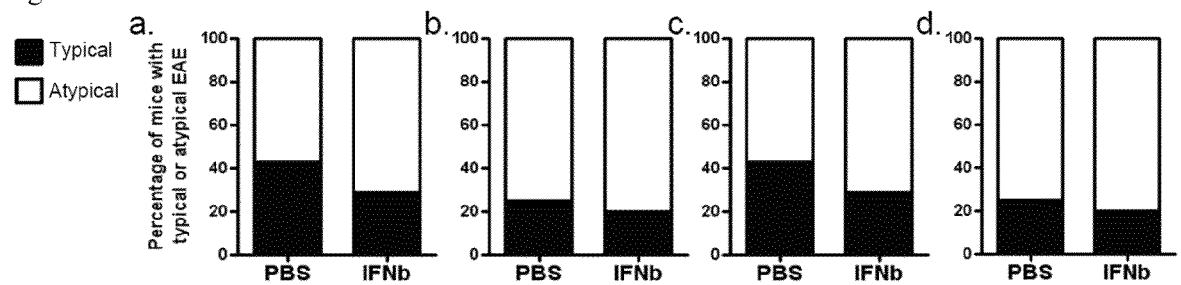
FIG. 17. Percentage of IFNγR−/− treated displaying typical or atypical EAE symptoms after treatment with: (a) Rebif or PBS daily from day 7 to day 17 post EAE induction, (b) rmIFN-β or PBS from day 10 to day 17 post EAE induction, (c) Rebif or PBS from day 0 to day 6 post EAE induction, and (d) rmIFN-β or PBS daily for 10 days beginning at disease score of 2 or 3.

The typical clinical manifestation of EAE in C57BL/6 mice is a progressive ascending paralysis which starts in the tail and leads to forelimb paralysis. In mice with decreased IFN-γ signaling, EAE symptoms are atypical and characterized by defects in proprioception with axial rotatory movement and ataxia with little hind limb paralysis. In our experiments, we observed that 60-80% of the IFN-γR$^{-/-}$ mice exhibited atypical EAE (scoring described in the methods) and this was not affected by IFN-β treatment (FIG. 17).

Our in vitro data demonstrated that cooperative signaling of IFN-β and IFN-γ indirectly induces IL-10 in CD4 T-cells via APCs. To test whether this occurs in disease, we induced EAE in IFNγR$^{-/-}$ recipient mice by transferring WT encephalogenic TH1 cell and treated with rmIFN-β or PBS every second day from day 0 to 10. Strikingly, we found that the recipient mice treated with IFN-β exhibited severe acute clinical symptoms which were significantly increased compared to the PBS treated mice (FIG. 4e).

Figure 18:
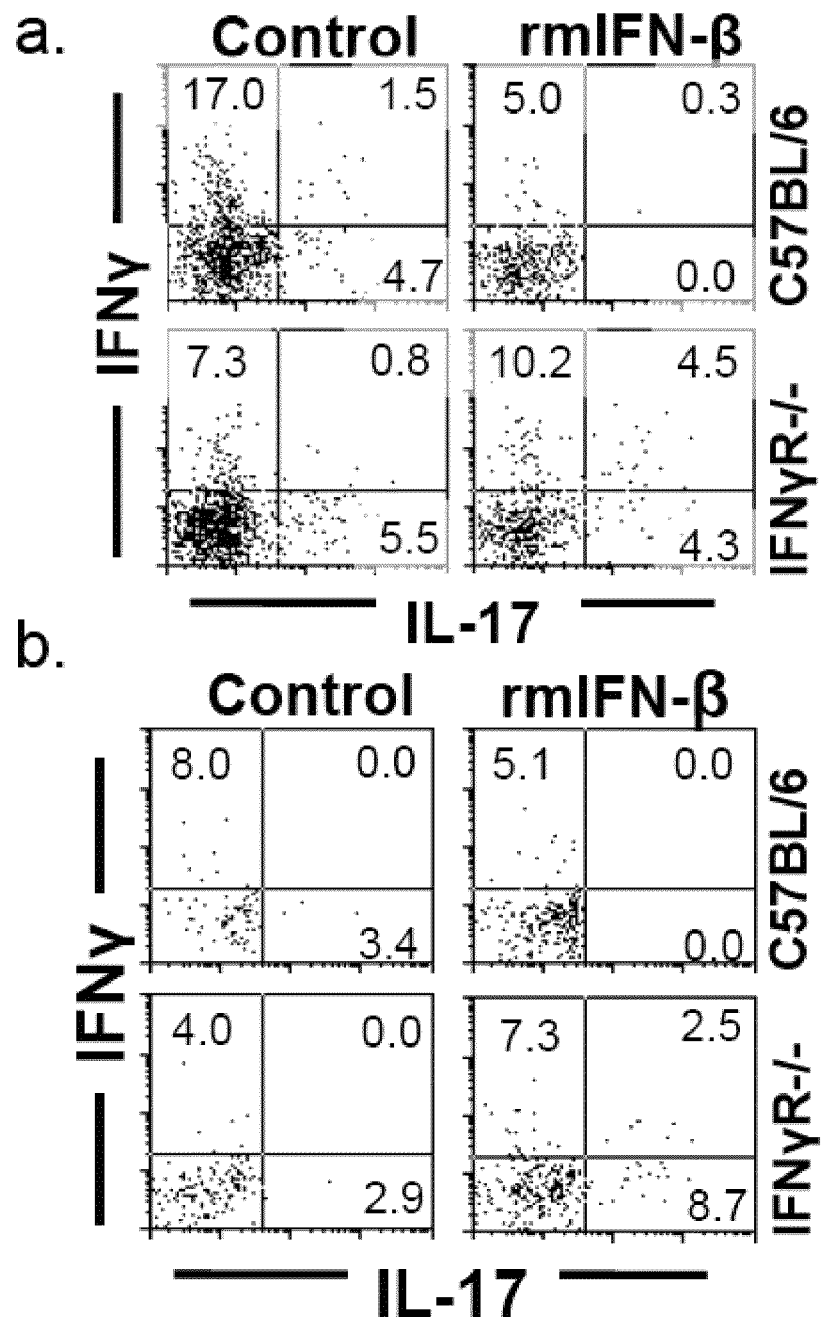
FIG. 18. Frequencies of the IFN-γ and IL-17 producing CD4 T-cells in the spinal cords (a) brainstem/cerebellum (b) 12 days post induction of EAE in C57BL/6 or IFNγR−/− mice treated with rmIFN-β or PBS.

Differential effects of IFN-β on infiltrating TH cells in WT and IFNγR$^{-/-}$ mice. In the CNS, we found that C57BL/6 mice treated with IFN-β had reduced frequencies of TH1 and TH17, as well as the population of CD4 cells co-expressing IL-17 and IFN-γ in spinal cords (FIG. 13a) and brainstem and cerebellum (FIG. 18b) 12 days post induction of disease. In contrast, IFN-β treatment increased the frequencies of these TH populations in the CNS of IFNγR$^{-/-}$ mice (FIG. 18a,b).

Figure 5:
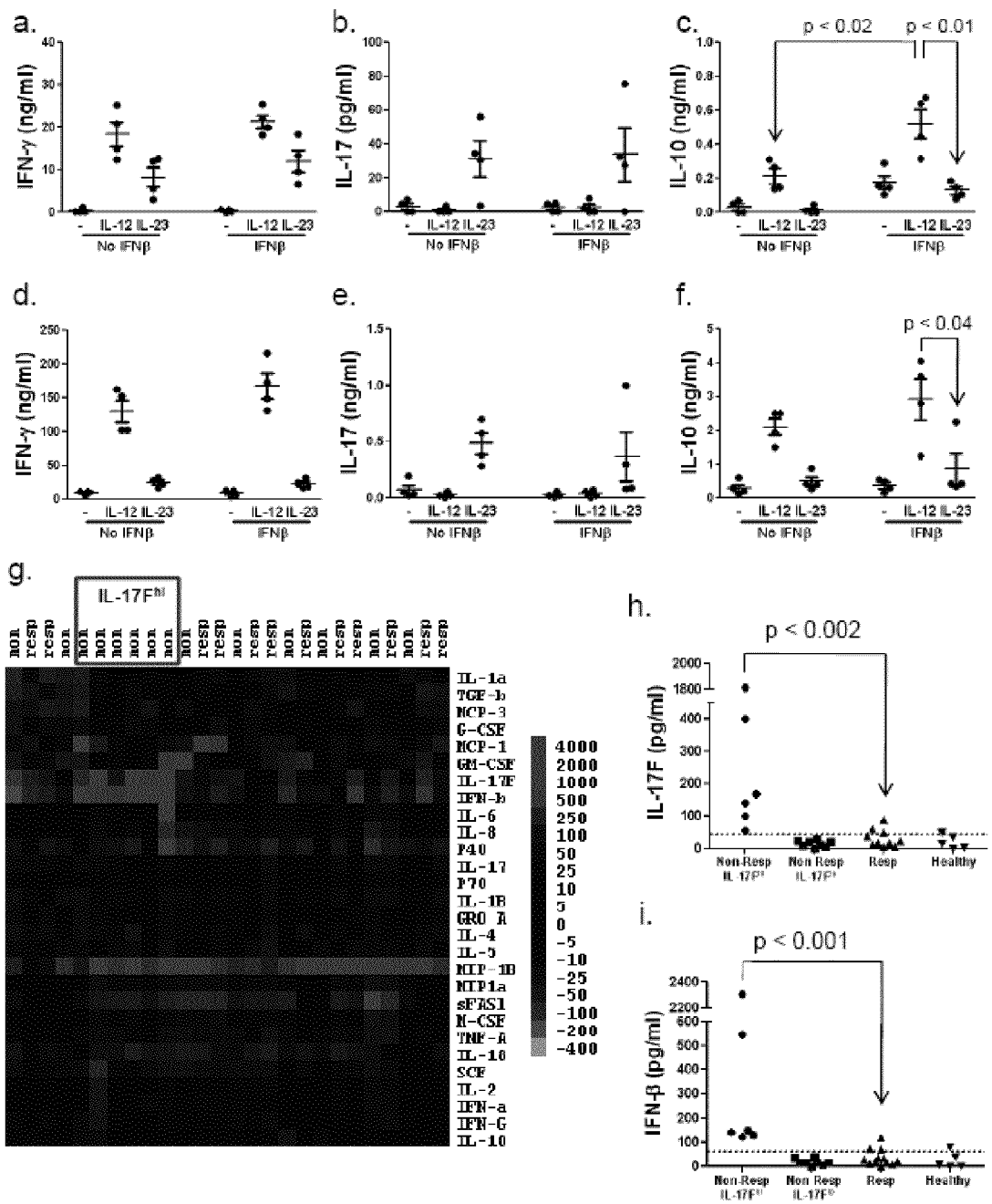
FIG. 5. (A-F) Effect of IFN-β on Human TH differentiation. Naïve human CD4 T-cells were cultured in non-polarizing, TH1 polarizing (IL-12) and TH17 polarizing (IL-23) conditions for 5 days (A-C) or 11 days (D-F) and IFNγ, IL-17A and IL-10 were assessed by ELISA. Day 11 cultures were further reactivated in the presence of beads coated with anti-CD3/CD28/CD2 Abs for 48 hrs prior to analysis. (G-I) Pre-Treatment cytokine profiles in serum of IFN-β responder and non-responder MS patients. G) Relative cytokine levels in responder and non-responder MS patients. Relative cytokine levels in serum from responder and non-responder MS patients were depicted as difference in relation to healthy controls. Samples were analyzed by hierarchical clustering, and displayed as a heat map where red represents increased levels, black represents similar levels and green represents decreased levels of cytokine compared to healthy controls. H) Concentration of IL-17F in subsets of pre-treatment MS patients and healthy control. Cytokine concentrations were calculated from a standard linear regression of known quantities of IL-17F. I) Concentration of IFN-β in subsets of pre-treatment MS patients and healthy control. Cytokine concentrations were calculated from a standard linear regression of known quantities of IFN-β.

Effect of IFN-β on Human T helper differentiation. To determine the effects of IFN-β on human T helper cell differentiation, we stimulated naïve CD4 cells from 4 donors for 5 and 11 days in non-polarizing, TH1 polarizing (IL-12) and TH17 polarizing (IL-23) in the presence or absence of IFN-β. We found that IFN-β had no effect on IFN-γ production in the all polarizing conditions after 5 or 11 days of culture (FIG. 5a, d). IL-17 production was also not effected by IFN-β after 5 days of culture (FIG. 5b). However, by day 11, IL-17 was inhibited by IFN-β during TH17 differentiation of 3 donors (578 ng/ml to 85 ng/ml, 696 ng/ml to 304 ng/ml, 284 ng/ml to 90 ng/ml) and in one donor IFN-β increased IL-17 production (385 pg/ml to 998 pg/ml) (FIG. 5e). During TH1 polarization, IFN-β significantly increased IL-10 production by day 5 (FIG. 5c) in all donors and the induction of IL-10 was greater in TH1 compared to the non-polarizing and TH17 polarizing conditions on both day 5 and day 11 (FIG. 5c,f).

Figure 19:
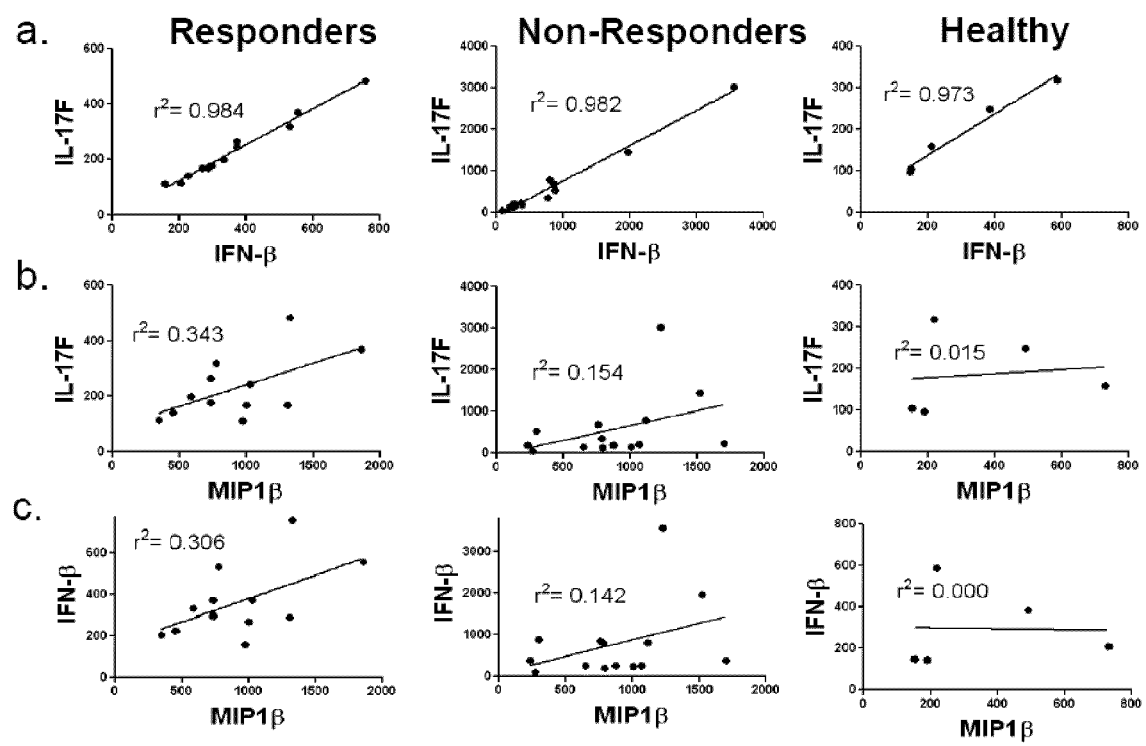
FIG. 19. Correlation of a) IL-17F vs IFN-β levels, b) IL-17F vs MIP1β levels and c) IFN-β vs MIP1β in serum from responders, non-responders and healthy controls. $R^2$ values close to 1 demonstrate that the cytokines are positively correlated.
Figure 20:
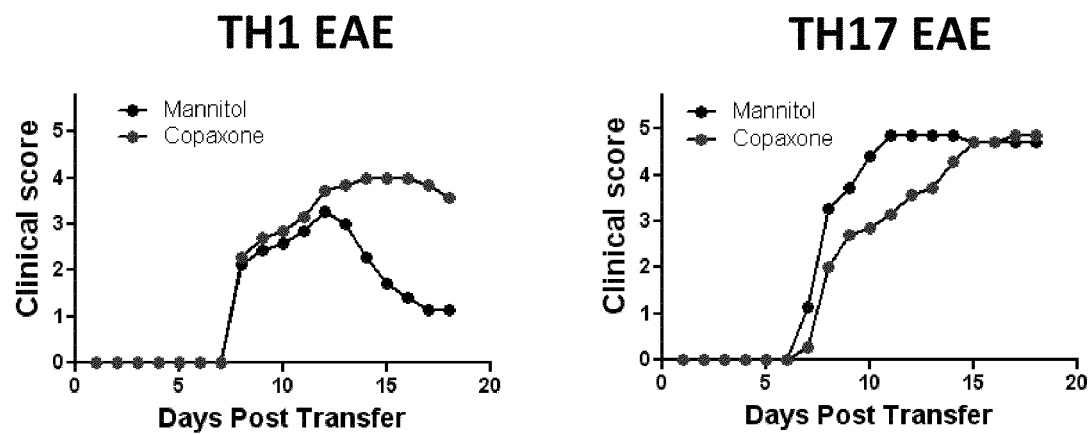
FIG. 20. Comparison of the effect of copaxone and control on TH1 and TH17 induced disease.

Cytokine Profiles Before Treatment of RRMS patients responding to IFN-β versus non-responders. We analyzed the pre-treatment levels of 26 cytokines/chemokines in the serum of RRMS patients, 12 were classified as responders and 14 as non-responders to IFN-β treatment. The median relapse rate in the two years following initiation of IFN-β treatment in the non-responders was 2, while it was 0 in the responder population. Likewise, the median number of steroid interventions was 2 in the non-responders and 0 in the responders (Table 1). Cluster analysis of the cytokine profiles grouped 5 non-responders together (FIG. 5g). This group of non-responders had significantly elevated serum concentrations of both IL-17F and IFN-β compared to the responders (FIG. 5h,i). Furthermore, we found there was a significant correlation with IL-17F and IFN-β levels found in the serum of responders, non-responders and healthy individuals (FIG. 19a). This strong correlation was not found in comparing IL-17F or IFN-β to MIP1β (Supplementary FIG. 14b,c) or other analytes.

IFN-β is one of the most popular treatments for MS. However, a major limitation with IFN-β is that 30-50% of MS patients do not respond to treatment. Therefore, in the clinical setting, it would desirable to identify responders and non-responders prior to the initiation of treatment. In a series of mouse experiments, we identified that mice with TH1 EAE respond to IFN-β treatment, whereas mice with TH17 EAE are non-responders.

In TH1 EAE, an outcome strongly correlated with effective IFN-β treatment was the induction of IL-10. IL-10 has immune suppressive properties such as inhibiting the pro-inflammatory cytokine production and antigen presentation by dendritic cells. Thus, increased IL-10 after IFN-β stimulation is likely a critical contributing factor for attenuating neuro-inflammation. Given that IFN-β treatment inhibited TH1 EAE, we speculated that effective IFN-β treatment depended on high IFN-γ levels during the progression of EAE. In fact, we found that in active EAE in C57BL/6 mice, where TH1 cells are found in high abundance during acute EAE, IFN-β treatment was effective in wild type mice, but worsened EAE in mice deficient in IFN-γ receptor. Furthermore, by inducing EAE by transfer of WT encephalitogenic TH1 cells into IFNγR$^{-/-}$ recipients, we found that the role IFN-γ plays in IFN-β therapy is to target non-T-cells. In accordance to these EAE data, our cell culture experiments reveal that the induction of IL-10 by IFN-β in CD4 T-cells requires the presence of APCs and also requires cooperative IFN-γ signaling.

In TH17 EAE, IFN-β treatment exacerbates EAE. This is in opposition to one popular hypothesis on the mechanism of IFN-β treatment; that it attenuates disease by inhibiting the differentiation of TH17 cells. We find that IFN-β, in synergy with IFN-γ, inhibits IL-17 production. Yet, IFN-β is ineffective in treating TH17 induced EAE and, in fact, increases symptoms in these mice.

We analyzed cytokine and chemokine levels in serum from RRMS patients prior to the initiation of IFN-β treatment. After treatment began, disease course was monitored for two years or longer and the patients were classified as responders and non-responders. All non-responders had relapses during first 2 years of IFN-β treatment where the responders had none. During relapses, the non-responders received steroids therapy which has powerful immune suppressive activity that would attenuate disease progression in these patients. Therefore, it is quite reasonable to describe the clinical course of the non-responders as exacerbated compared to the responders. Strikingly, we found a subset of non-responders that have high serum levels of the TH17 cytokine, IL-17F. IL-17F has been shown to be produced by TH17 cells in EAE suggesting that this group of MS patient is skewed towards a TH17 disease. Furthermore, these patients have high levels of endogenous IFN-β in their serum compared to the responders. These data show that there is striking correlation in the concentration IL-17F and IFN-β in serum, demonstrating that these two cytokines are associated biologically.

Without limiting the invention, it can be hypothesized that IFN-β is pro-inflammatory during TH17 biased disease. Therefore, not only would IFN-β treatment be ineffective, it could worsen symptoms. This hypothesis is supported by our observations in EAE, where symptoms were worsened by IFN-β treatment in TH17 induced EAE, and in RRMS, where patients with high IL-17F have exacerbated disease.

In addition, neuromyelitis optica (NMO), another demyelinating disorder closely related to MS, also provides evidence for this hypothesis. IFN-β treatment of individuals with NMO induces severe relapses. It has been shown that there are high levels of IL-17 found in the CSF of patients with NMO. The disease processes of NMO and the group of non-responders with high levels of IL-17F are likely similar.

Manipulating the effects of cytokines has been a popular and at times effective strategy for the development of treatments for MS. However, our data demonstrate that IFN-β is a double-edged sword. In the context of a TH1 response with high IFN-γ levels, IFN-β is anti-inflammatory and is effective in attenuating disease. However, in the context of a TH17 response, with high levels of IL-17A/F, IFN-β is pro-inflammatory and IFN-β can exacerbate disease.

A direct result of this work is the utility of a test for IL-17F prior to embarking with therapy using IFN-β. This will reduce the morbidity of IFN-β, as it would preclude those whose clinical symptoms are likely to worsen when it is used. And it would select those patients who would benefit from the drug. In an contemporary environment where economic impacts of medical decision making is more and more important, the virtues of excluding certain patients has further urgency. And here the exclusion would save not only the unnecessary expenditure of funds, it would also save individuals from undesired complications. IL-17F is thus one of the first biomarkers that could govern whether or not a high priced recombinant drug is used in the clinic.

Materials and Methods

Mice. C57BL/6 and B6.129S7-Ifngr1$^{tm1Agt}$/J (IFNγR$^{-/-}$) mice were purchased from Jackson Laboratory (Bar Harbor, Me.) and bred at UAB and/or Stanford. B6 Stat1−/− mice were provided by R. Lorenz (UAB). All animals were housed and treated in accordance to National Institutes of Health guidelines.

EAE induction and treatment. Age and sex matched C57BL/6 and IFNγR$^{-/-}$ mice were induced with EAE by an immunization 150 μg of MOG p35-55 (Biosynthesis) emulsified in CFA followed by an intraperitoneal injection of with 500 ng of *Bordetella pertussis* toxin (Difco Laboratories) in PBS at the time of, and two days following immunization. Mice treated with 1 ug/ml Rebif (Serono) were received daily injections from day 0 to day 6 or day 7 to day 17 post induction of EAE. Mice treated with 1000 units of rmIFN-β (RandD) received daily injections from day 10 to day 17. Typical EAE symptoms monitored daily using a standard clinical score ranging: 1) Loss of tail tone, 2) incomplete hind limb paralysis, 3) complete hind limb paralysis, 4) forelimb paralysis, 5) moribund/dead. Atypical EAE symptoms were scored as follows: 1) hunched appearance, slight head tilt, 2) severe head tilt, 3) slight axial rotation/staggered walking, 4) severe axial rotation/spinning, 5) moribund/dead.

Adoptive Transfer. EAE was induced in C57BL/6 mice and after 10 days of spleens and lymph node cells were isolated and re-stimulated with MOG p35-55 with 10 ng/ml of IL-12 or IL-23 for 3 days. Thirty million cells were adoptively transferred in healthy C5LBL/6 recipient mice. Mice were treated with 1000 U/dose of rmIFN-β or PBS every second day from day 0-10 post transfer and examined daily for clinical signs. For histopathological analysis, spinal cords of EAE mice were fixed in 10% formaldehyde. Paraffin sections (6 μM thick) were stained with LFB and H&E.

Isolation of Mononuclear cells from CNS. Infiltrating cells were isolated from spinal cords or brainstem/cerebellum as previously described (26). Briefly, CNS homogenates were obtained from 3-4 perfused animals and incubated with collagenase (2 mg/ml) and DNAse (5 units/ml) for 1 h at 37° C.; mononuclear cells were purified by two step Percoll gradient centrifugation.

Mouse TH differentiation. Spleen cells from C57BL/6 or STAT1$^{-/-}$ mice were depleted of CD8 T-cells by magnetic sorting using biotinylated anti-CD8 (53-6.7, BD Bioscience) and anti-biotin beads (Miltenyi) and cultured at $2.5 \times 10^6$/ml in 96 or 48 well plates in media (RPMI 1640 supplemented with 2 mM L-glutamine, 1 mM sodium pyruvate, 0.1 mM non-essential amino acids, 100 U ml$^{-1}$ penicillin, 0.1 mg ml$^{-1}$ streptomycin, 0.5 μM 2-mercaptoethanol and 10% fetal calf serum). These cells were stimulated for 3 or 5 days with 1 μg/ml of anti-CD3 (145-2C11, Ebioscience) in the following conditions: non-polarizing, TH1 (10 ng/ml IL-12) TH17 polarizing (1 ng/ml rhTGF-β and 20 ng/ml rmIL-6; R&D Systems), TH1 polarizing (10 ng/ml IL-12; R&D Systems) or inducible T-reg polarizing (TGF-β 1 ng/ml) in the presence or absence of recombinant mouse IFN-β (100 U/ml). Where indicated, 10 μg/ml of purified anti-IFN-γ (XMG1.2, Ebioscience), anti-IL-10 (JES5-2A5, Ebioscience) or anti-IL-27p28 (R&D Systems) was added to the cultures for their neutralizing effects.

Naïve (CD62$^+$) and activated/memory (CD62$^-$) CD4 T cells were obtained by magnetic selection (Miltenyi) and stimulated with 1 μg/ml of anti-CD3 in the presence of antigen presenting cells (T-cell depleted splenocytes) at a 1:5 ratio in 96 flat bottom wells in non-polarizing, TH1 or TH17 conditions (IL-6/TGFβ) or IL-23 (10 ng/ml) alone. Purified CD4$^+$ T-cells cultured in the absence of antigen presenting cells were stimulated by plate bound anti-CD3 (5 μg/ml) and anti-CD28 (0.5 μg/ml).

Antigen specific TH differentiation, LN cells from MOG p35-55 immunized mice were re-stimulated with MOG p35-55 for 3 days in 10 ng/ml IL-12 or IL-23 in the presence or absence of IFN-β.

Intracellular Flow Cytometry, ELISA and Multiplex Analysis of Mouse Cytokines. Mononuclear cells from spinal cords or cultured cells were stimulated with 50 ng/ml of PMA and 500 ng/ml of ionomycin (Sigma-Aldrich) in the presence of Golgi-stop (BD Biosciences) for 4 h. Cells were then incubated with anti-CD16/32 (2.4G2, FcR block) surface staining with anti-CD4FITC or anti-CD4PerCP (BD Biosciences). The cells were fixed and permeabilized with Cytofix/Cytoperm (BD Biosciences) and stained with anti-IFNγ-Cy5 (BD Biosciences), anti-IL-17PE (Ebioscience), anti-IL-10 PE (Ebioscience) or anti-FoxP3 (Ebioscience). Samples were acquired on a FACSCalibur or FACScan flow cytometer (BD Biosciences) and data analysis was conducted using WinMDI software (TSRI). ELISA kits for IL-17 (R&D Systems), IL-10 (BD Biosciences), IFN-γ (BD Biosciences), and IL-27p28 (R&D Systems) were used to analyze the supernatants from 3-4 day cultures. IL-4, TNF, IL-6, IL-1α, IL-1β, TGF-β, IL-13, IL-3, IL-5, GM-CSF, G-CSF, MCP-1, Rantes and IP10 were analyzed in supernatants by multiplex bead analysis (Panomics) according to the protocol recommended by the manufacturer.

T-Cell Proliferation. $5 \times 10^5$ spleen cells, depleted of CD8 T-cells, were cultured in triplicate in 96-well plates with 1 μg/ml anti-CD3 in the presence of the indicated concentration of rmIFN-β. After 48 hrs, cultures were pulsed with [3H] thymidine for an additional 18 hrs, and incorporation of thymidine was determined.

In vitro STAT1 activation. Splenocytes from C57BL/6 and IFNγR$^{-/-}$ were stimulated for 15 mins. with 100 units of rmIFN-β. Cells were fixed with 1.6% paraformaldehyde and permeablized with 100% methanol before staining with anti-CD4-FITC (Ebioscience) and anti-pSTAT1-PE (BD Biosciences). The amount of total STAT1 was analyzed by SDS-PAGE, transferred to nitrocellulose membrane, probed with anti-STAT1 (Cell Signaling), and the signal visualized by chemiluminescence.

Human TH differentiation. Peripheral blood mononuclear cells were prepared from buffy coats obtained from healthy donors (Stanford Blood Center) by centrifugation through Ficoll (Histopaque 1077; Sigma). CD4$^+$ T cells were isolated by two rounds of magnetic bead depletion of CD19$^+$, CD14$^+$, CD56$^+$, CD16$^+$, CD36$^+$, CD123$^+$, CD8$^+$, T cell receptor-γ and T cell receptor-δ positive and glycophorin A-positive cells (CD4$^+$ T Cell Isolation Kit II) on an AutoMACS instrument (Miltenyi Biotec). Subsequently, naive CD45RA$^+$ T cells were obtained by two rounds of depletion with anti-CD45RO and anti-CD25 magnetic beads (Miltenyi Biotec). T cells (CD4$^+$CD45RO$^-$CD25$^-$) were cultured for 5 days in 24-well flat-bottomed plates (Falcon) at a density of $5 \times 10^5$ cells per well in Yssel's media containing 1% human AB serum (Gemini Bio-Products) along with beads coated with anti-CD2, anti-CD3 and anti-CD28 (1 bead per 10 cells; T Cell Activation/Expansion Kit, Miltenyi Biotec) in nonpolarizing conditions (no cytokines), TH1-polarizing conditions (human IL-12 (5 ng/ml); R&D Systems) or TH17-polarizing conditions (human IL-23 (50 ng/ml; DNAX)) in the presence or absence of human IFN-β (100 U/ml; PBL). Cells were split and were cultured for an additional period of 6 d in the presence of the various cytokines and IL-2 (100 U/ml; R&D Systems). For day 5 cultures, cytokines were directly assayed from cell supernatants. For Day 11 cultures, $1 \times 10^6$ cells per ml were stimulated with T cell-activation beads in the presence of IL-2 and culture supernatants were collected or 48 h and cytokines were assayed.

MS Patients Clinical Classification and Serum Collection. Twenty-six closely monitored RRMS patients receiving IFNβ treatment for at least 12 months were identified from the outpatient clinic as responders or non-responders to IFNβ therapy at the MS Center Amsterdam, the Netherlands. The patients were classified based on EDSS (Extended Disability Status Scale) progression and the number of relapses and steroid interventions (3 days of 1000 mg/day i.v. methylprednisolone) in the two years before initiation of treatment as compared to the first two years after starting treatment (see Table 1). Two MS neurologists, blinded to the laboratory data, independently classified the selected patients as responder or non-responder. In case of disagreement there was a consensus meeting afterwards. Serum samples were obtained at a fixed time of the day just before starting IFNβ therapy. The study design received approval from the institutional Medical Ethics Board of the VU University Medical Center, Amsterdam, the Netherlands. All patients signed written informed consent.

ELISA and Multiplex Analysis of Human cytokines. Supernatants from TH differentiation cultures were assayed for IL-17, IL-10 and IFN-γ by ELISA (Ebioscience). Analysis of cytokines in the sera from MS patients and healthy controls was performed by multiplex bead analysis (Panomics) according to the protocol recommended by the manufacturer. Multiplex results were analysed using Gene Cluster software to identify features with significant differences in antibody reactivity and the patient samples were ordered using a hierarchical clustering algorithm and the results presented as a heat map using TreeView software.

Statistical analysis. EAE data are presented as means±SEM and statistical significance was determined using a two tailed Mann-Whitney test with a value of P<0.05 was considered significant. STAT1 activation and ELISA data are presented as means±1 standard deviation and statistics significance was determined using a two tailed student T-test.

TABLE 1

Demographic and clinical characteristics of patients with relapsing remitting multiple sclerosis and their clinical response to IFNβ therapy

|  | Responder | Non-responder |
|---|---|---|
| Number | 12 | 14 |
| Female/Male (n) | 10/2 | 11/3 |
| Median age at onset (yr) | 27.6 [24.5; 35.8] | 26.7 [19.3; 36.0] |
| Median age at start IFNβ (yr) | 33.5 [30.3; 39.5] | 33.0 [23.0; 37.8] |
| Median EDSS score around start IFNβ | 2.5 [2.0; 3.5] | 2.5 [1.8; 4.3] |
| Relapse rate in 2 yrs before start IFNβ | 2 [2-3] | 2 [1-3] |
| Relapse rate in 2 yrs after start IFNβ | 0 [0; 0] | 2 [1.5; 2.0] |
| Steroid interventions before start IFNβ (n) | 0 [0; 2] | 1 [0; 3] |
| Steroid interventions after start IFNβ (n) | 0 [0; 0.5] | 2 [1; 3] |
| Duration of IFNβ treatment (mnths) | 80 [46; 141] | 56 [38; 104] |
| Avonex | 4 | 5 |
| Rebif | 2 | 8 |
| Betaferon | 6 | 1 |

Median values are shown with 25 and 75 percentiles.
IFNb = Interferon-beta.
EDSS = Expanded Disability Status Scale Example 2

Expression of IL-17A and IL-17F in NMO Samples

Figure 21:
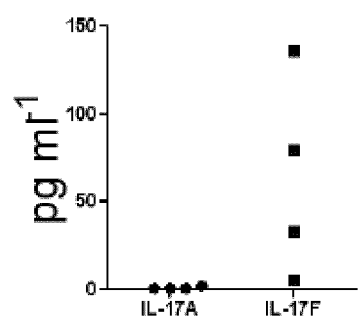
FIG. 21A-21C, differential expression of IL-17A and IL-17F in NMO and EAE.
Figure 21:
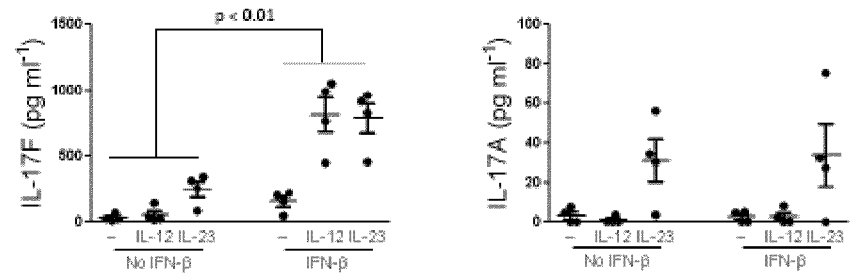
Figure 21:
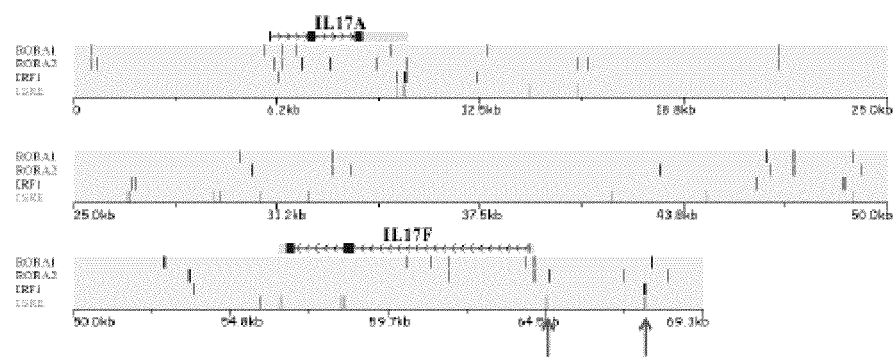
Figure 22:
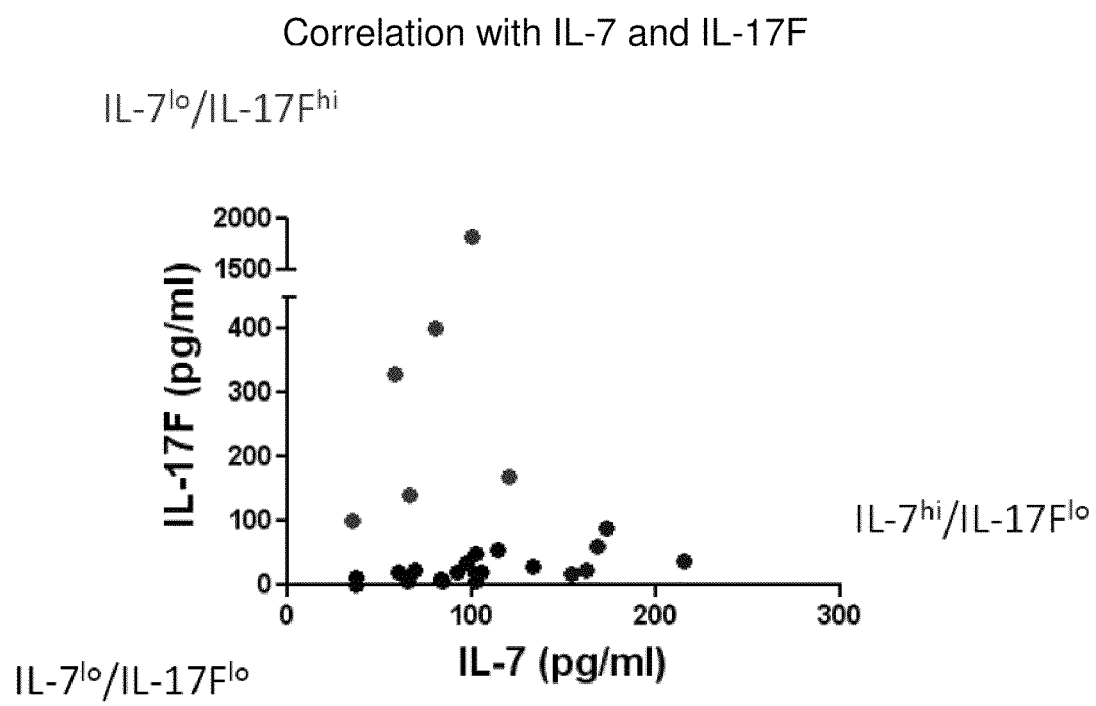
FIG. 22. Inverse Correlation of IL-7 and IL-17F in patients.
Figure 23:
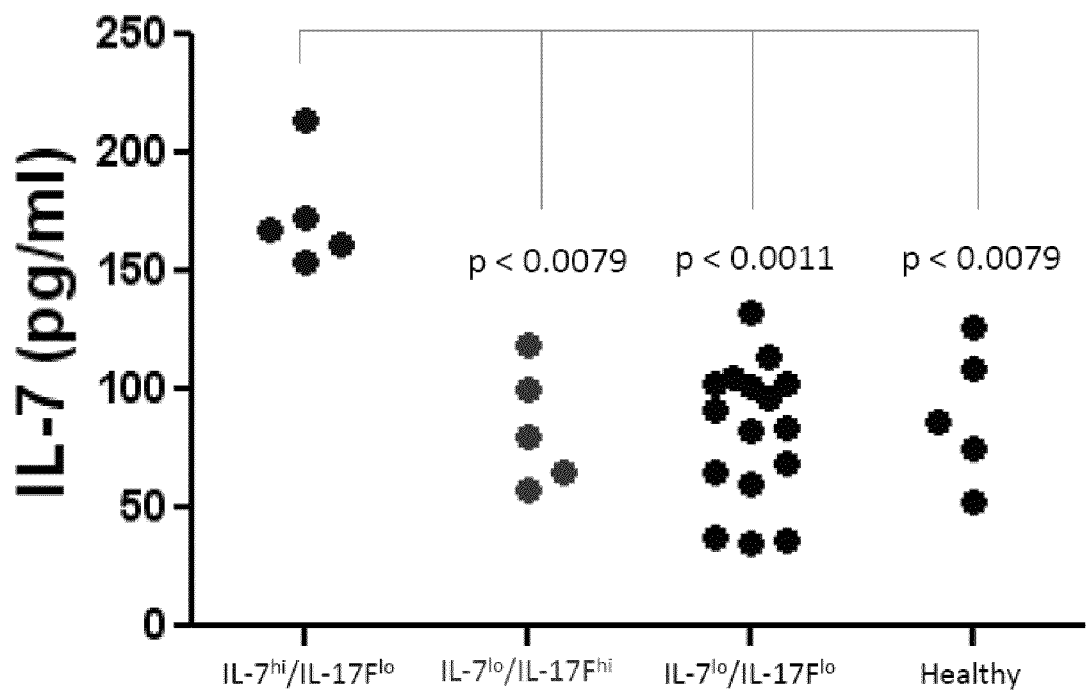
FIG. 23. Serum levels of IL-7 and IL-17F in patient categories, compared to a normal sample.
Figure 24:
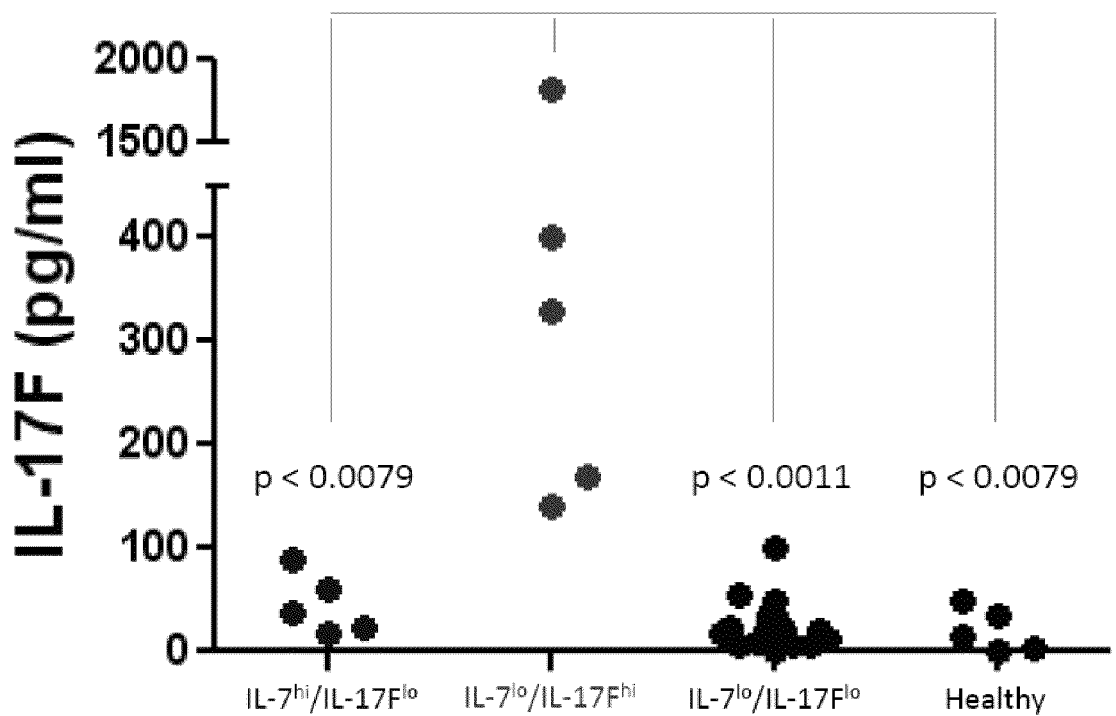
FIG. 24. Serum levels of IL-17 in patient categories, compared to a normal sample.
Figure 25:
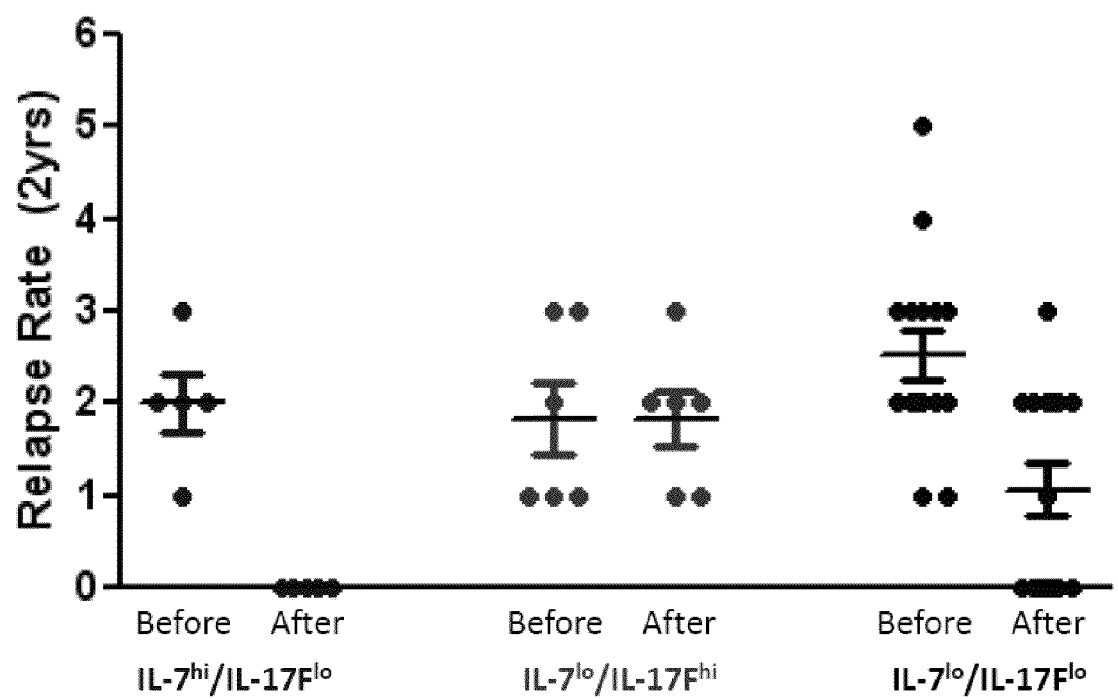
FIG. 25. Relapse Rate after 2 years on β-IFN in reference to levels of IL-7 and IL-17F.

In serum sample from an NMO patient, it was found that while levels of IL-17F were significantly increased over baseline, the levels of IL-17A remained low (shown in FIG. 21A). In response to IFN-b, human CD4 T cells increase secretion of IL-17F but not IL-17A, (shown in FIG. 21B). This response may be due to the presence of putative Type 1 interferon responsive elements upstream of IL-17F but not IL-17A, (shown in FIG. 21C).

Example 3

We compared analyte levels across the 3 treatment groups (Avonex, Betaferon, or Rebif) before treatment is given (at baseline) using analysis of variance (ANOVA) and Kruskal-Wallis tests to determine if baseline values differed among the treatment groups. These tests are described in standard introductory statistics texts such as Glantz 2005: Primer of Biostatistics: Sixth Edition, Stanton Glantz McGraw-Hill Medical; 6 edition (Apr. 15, 2005); ISBN-13: 978-0071435093, herein incorporated by reference. These are respectively parametric and nonparametric methods to test for quantitative differences in a response variable (analyte) as a function of a categorical variable (treatment group). The data contained 14 patients labeled responder=0, which are non-responders, and 12 patients labeled responder=1, which are responders. We did not include the healthy subjects in these analyses. The dataset includes data for 54 analytes. See Table 2. Assignment of subjects to treatment groups (Avonex, Betaferon, or Rebif) was non-random.

TABLE 2

| Sample ID | ENA78 | IFN-b | EOTAXIN | IL-10 | FGFb | IL-12-P70 | G-CSF | IL-12P40 | GM-CSF | IL-13 | IL-15 | IL-17 | GRO ALPH | IL-17F | AHGF | IL-18 | ICAM-1 | IL-1a |
|---|---|---|---|---|---|---|---|---|---|---|---|---|---|---|---|---|---|---|
| 201292 | 614.75 | 194.25 | 250.25 | 155 | 41 | 33.5 | 74 | 230.5 | 290.5 | 55.5 | 26.5 | 61.75 | 36.75 | 121 | 735.75 | 152.5 | 10911.25 | 98 |
| 634246 | 137 | 880.75 | 168 | 11 | 16 | 12 | 30.5 | 143.25 | 26 | 12.25 | 13 | 19.25 | 12.5 | 522.5 | 325.5 | 86.5 | 4388.75 | 53 |
| 825371 | 504.5 | 852 | 672.5 | 26.5 | 32 | 31.5 | 43.25 | 164.75 | 68.5 | 43.25 | 59 | 44 | 45.5 | 680.5 | 217.75 | 213.25 | 11496 | 169 |
| 1030489 | 737.5 | 287 | 952 | 53 | 45.25 | 55.75 | 76 | 91.5 | 151.75 | 111.5 | 42 | 97.5 | 58.25 | 168.5 | 551.75 | 267.5 | 8633.5 | 168 |
| 1141513 | 1276 | 372.25 | 1017.5 | 62.5 | 57 | 30.75 | 55.75 | 268 | 60.75 | 34 | 33.25 | 58 | 71.75 | 243.75 | 856 | 265.75 | 12736.75 | 113.5 |
| 1326051 | 77.75 | 99.5 | 181 | 15.25 | 14.5 | 10.5 | 17 | 105 | 33.25 | 15 | 12 | 18 | 14 | 49 | 184.25 | 27.75 | 8342.5 | 30.25 |
| 2628013 | 2309 | 776.25 | 553 | 43.5 | 40.5 | 46.5 | 89 | 262 | 121.25 | 64.25 | 35 | 83.5 | 68.5 | 339.75 | 649.5 | 183.25 | 11600 | 143.25 |
| 2889512 | 399.75 | 373.75 | 1197 | 43.5 | 25 | 52 | 107.5 | 296 | 111 | 86.25 | 42 | 95.5 | 75 | 265.75 | 193.25 | 45 | 9214 | 135 |
| 3193413 | 521 | 1449.75 | 742 | 44 | 52.75 | 32.5 | 48.5 | 138 | 60.75 | 32.5 | 31.75 | 40 | 66.75 | 1262.5 | 320.5 | 120 | 10631 | 100.25 |
| 3256985 | 1517.75 | 555.75 | 762.5 | 49.25 | 92.25 | 63.5 | 92.75 | 331 | 124.75 | 86 | 43 | 114.5 | 62.5 | 368.5 | 569.25 | 106 | 19429 | 134 |
| 3514566 | 154.75 | 269 | 1040.5 | 33.5 | 18 | 45.25 | 86 | 343.25 | 377 | 44.25 | 44.5 | 45 | 45.5 | 168.75 | 413.5 | 209.5 | 8008.5 | 151 |
| 3723343 | 177.5 | 264.25 | 481.75 | 14.25 | 18 | 24.5 | 83 | 131.5 | 98.5 | 43 | 29 | 39.75 | 42 | 197.5 | 504 | 139.5 | 12351.25 | 117.25 |
| 3958469 | 487 | 757.75 | 509.25 | 50.5 | 46 | 18.5 | 89.25 | 215 | 263.5 | 78.75 | 49 | 65.5 | 63 | 484.25 | 467.25 | 94.5 | 11085 | 181.75 |
| 4023341 | 3898.5 | 3558.25 | 608.5 | 60.5 | 47.5 | 48 | 73 | 1112 | 582.75 | 50 | 39.5 | 87.5 | 97.5 | 3030.75 | 348 | 236.5 | 12340 | 150.75 |
| 4393232 | 295 | 296 | 542.5 | 39 | 39 | 33.5 | 41.5 | 254.5 | 108.25 | 41.25 | 32.25 | 48.5 | 41 | 178.5 | 802 | 227.5 | 7122.25 | 109 |
| 4812525 | 578.25 | | 508.75 | | 53 | | 83.25 | | 1877 | | | | 77 | | 1309 | | 13835.75 | |
| 4924078 | 503.5 | | 572 | | 11.5 | | 36.5 | | 58.5 | | | | 19.5 | | 457.5 | | 5621 | |
| 5025882 | 1129 | | 1249.5 | | 75 | | 89 | | 96 | | | | 89 | | 962.75 | | 13052.75 | |
| 5661422 | 89.5 | | 598.75 | | 18.5 | | 39.5 | | 28.5 | | | | 34 | | 137 | | 10697.5 | |
| 6043240 | 211 | | 372 | | 14.5 | | 50 | | 65.5 | | | | 31.5 | | 176.5 | | 9520.75 | |
| 7037244 | 716.75 | | 679.75 | | 33 | | 83.5 | | 158.5 | | | | 47.5 | | 445.5 | | 11460.5 | |
| 7125158 | 613 | | 735.5 | | 73.5 | | 29.5 | | 100.75 | | | | 70.5 | | 771 | | 18241.5 | |
| 8161710 | 834.75 | | 213.5 | | 126 | | 114.5 | | 90.75 | | | | 90.5 | | 840.75 | | 18396 | |
| 8963130 | 207.5 | | 614.5 | | 44.5 | | 130.75 | | 76.75 | | | | 46 | | 260.75 | | 10798.5 | |
| 9090819 | 546.75 | | 440.5 | | 52 | | 89.25 | | 205 | | | | 89.25 | | 744 | | 14657 | |
| 9305897 | 818.25 | | 639.5 | | 29.5 | | 67 | | 99.5 | | | | 83.25 | | 431 | | 3135 | |
| H10 | 132.75 | | 702 | | 11.5 | | 40.5 | | 144.25 | | | | 38 | | 210.75 | | 436.25 | |
| H11 | 366.75 | | 281.25 | | 11 | | 51.5 | | 66.5 | | | | 33.5 | | 24.25 | | 5943 | |
| H7 | 161.25 | | 1245.25 | | 16.75 | | 66.5 | | 96.75 | | | | 53.5 | | 349 | | 7661.75 | |
| H8 | 265.75 | | 570.25 | | 12 | | 72.75 | | 35 | | | | 26.5 | | 321.25 | | 1055.25 | |
| H9 | 256.75 | | 323.5 | | 11.5 | | 64 | | 58 | | | | 34.25 | | 157.75 | | 3340.5 | |

| Sample ID | IFN-a |
|---|---|
| 201292 | 33.5 |
| 634246 | 13.25 |
| 825371 | 65.5 |
| 1030489 | 46.75 |
| 1141513 | 51.75 |
| 1326051 | 12 |
| 2628013 | 31 |
| 2889512 | 14 |
| 3193413 | 30 |
| 3256985 | 72.25 |
| 3514566 | 13.5 |
| 3723343 | 14.5 |
| 3958469 | 9.5 |
| 4023341 | 52.75 |
| 4393232 | 40.75 |

TABLE 2-continued

| Sample ID | IL-1B | IL-1RA | IL-2 | IL-4 | IL-5 | IL-6 | IL-7 | IL-8 | IP10 | LEPTIN | LIF | M-CSF |
|---|---|---|---|---|---|---|---|---|---|---|---|---|
| 4812525 | 39.5 | 253 | 66 | | | 39.5 | | 51.25 | 31.5 | | 135 | 283 | 125.5 |
| 4924078 | 9.5 | 225.5 | 24 | | | 15.75 | | 19 | 10.5 | | 142 | 43.75 | 48.5 |
| 5025882 | 173.75 | 803.5 | 176.5 | | | 54 | | 79 | 62 | | 782.5 | 197 | 173 |
| 5661422 | 17.5 | 389 | 32 | | | 16.75 | | 27.25 | 10.5 | | 185.25 | 132 | 68.5 |
| 6043240 | 19 | 205.5 | 31.75 | | | 23.5 | | 52.5 | 34.75 | | 114.25 | | 179 |
| 7037244 | 20 | 267.25 | 70 | | | 36.5 | | 55 | 55.5 | | 186 | 62.25 | 96.25 |
| 7125158 | 54 | 531 | 68.25 | | | 32.5 | | 55 | 28.75 | | 318 | 82.25 | 180 |
| 8161710 | 80.5 | 374 | 91.75 | | | 61 | | 70.25 | 43 | | 218 | 160 | 156 |
| 8963130 | 41 | 1968.25 | 62.25 | | | 56.25 | | 38.25 | 75.75 | | 1443.75 | 177.75 | 116 |
| 9090819 | 39 | 333.25 | 107.75 | | | 46 | | 81.75 | 123 | | 199.75 | 319.25 | 213 |
| 9305897 | 30.5 | 157.75 | 58 | | | 59.25 | | 77 | 60.25 | | 111 | 296 | 120.5 |
| H10 | 7 | 586.75 | 58.75 | | | 50.5 | | 52.5 | 121 | | 318 | 204 | 131.75 |
| H11 | 10.25 | 145.5 | 25.25 | | | 46.5 | | 53.5 | 56.5 | | 97 | 169.75 | 112.75 |
| H7 | 12.5 | 210.25 | 54.5 | | | 17.75 | | 45 | 49.5 | | 158.75 | 24 | 160 |
| H8 | 13.5 | 148.5 | 27.5 | | | 28 | | 51 | 32.75 | | 104 | 70 | 99 |
| H9 | 8 | 385 | 31 | | | 28.5 | | 50.75 | 60.5 | | 249 | 53.5 | 120 |
| | | | | | | 18.5 | | 76.25 | 44 | | | 43.5 | |
| | | | | | | | | | 33 | | | | |
| | | | | | | | | | 38.5 | | | | |

| Sample ID | IL-1B | IL-1RA | IL-2 | IL-4 | IL-5 | IL-6 | IL-7 | IL-8 | IP10 | LEPTIN | LIF | M-CSF |
|---|---|---|---|---|---|---|---|---|---|---|---|---|
| 201292 | 68 | 93.75 | 23 | 67.75 | 59 | 58.75 | 120.75 | 75.75 | 416.75 | 3302.5 | 53.5 | 56 |
| 634246 | 25 | 45.5 | 9.5 | 43.25 | 26.5 | 22.5 | 39.75 | 16.5 | 160.5 | 2582.75 | 22.5 | 16 |
| 825371 | 57.5 | 85.25 | 37.75 | 80.75 | 49.5 | 30.25 | 76 | 35.5 | 159.75 | 1038 | 44.5 | 28.5 |
| 1030489 | 128.75 | 122.75 | 51.5 | 119.75 | 67 | 54 | 188.25 | 76.25 | 898.75 | 1110 | 86.75 | 51.25 |
| 1141513 | 85.25 | 154 | 45 | 98.75 | 67 | 44.5 | 114.5 | 124 | 485.25 | 1818.25 | 49.25 | 69 |
| 1326051 | 22.75 | 28.5 | 7.25 | 36 | 29 | 9.5 | 42.5 | 15.5 | 86.5 | 1261.25 | 18 | 40 |
| 2628013 | 105.5 | 124.5 | 33.25 | 107.5 | 107 | 40.75 | 136 | 47.25 | 372.25 | 9198.25 | 73.5 | 16.75 |
| 2889512 | 138.5 | 40.25 | 16.5 | 143.5 | 55 | 15.5 | 269 | 21 | 230.25 | 4454 | 122.25 | 68.5 |
| 3193413 | 55.75 | 90.25 | 44.5 | 50.5 | 66 | 29 | 67 | 54.5 | 362 | 3092 | 39.5 | 124.5 |
| 3256985 | 133.75 | 168.5 | 62.5 | 102 | 107 | 64.25 | 207 | 105.25 | 200.75 | 9433 | 95 | 18.75 |
| 3514566 | 92.25 | 49 | 15.5 | 44 | 45 | 14.25 | 121.5 | 49.75 | 170 | 2327.5 | 65 | 16 |
| 3723343 | 80 | 70.5 | 16 | 84.25 | 104 | 20.5 | 80 | 15.5 | 330 | 7973.75 | 45.75 | 12.25 |
| 3958469 | 83.5 | 47 | 19.5 | 116.25 | 114.5 | 15 | 213.25 | 14.5 | 263.25 | 7041.5 | 83.5 | 59 |
| 4023341 | 121.5 | 128 | 50.5 | 129.25 | 153 | 2445.25 | 118 | 367.25 | 511 | 9968 | 71 | 47.75 |
| 4393232 | 86.5 | 134.5 | 51 | 84 | 116 | 28.5 | 108 | 46 | 157 | 9251.75 | 51.75 | 72.75 |
| 4812525 | 112.5 | 153.5 | 39.5 | 106 | 61.5 | 38 | 97.25 | 155 | 216.5 | 2993.25 | 58.5 | 11.5 |
| 4924078 | 51.5 | 55.5 | 5.5 | 46.25 | 80 | 7 | 42.25 | 12 | 184.5 | 6895 | 31.75 | 71 |
| 5025882 | 100.5 | 140.75 | 176.75 | 132.75 | 50.5 | 63.25 | 143.5 | 88 | 492 | 462.75 | 86.75 | 15.5 |
| 5661422 | 29.25 | 69.5 | 7.5 | 60.5 | 25.75 | 13.75 | 69.5 | 29 | 1969.5 | 1397 | 40.5 | 12 |
| 6043240 | 41 | 53 | 11.5 | 52.5 | 33.5 | 17 | 75.25 | 16.5 | 1651.75 | 707 | 24.25 | 23.5 |
| 7037244 | 88 | 75.75 | 23.25 | 98.5 | 76.5 | 20 | 125 | 31.5 | 360.5 | 5504.25 | 61 | 93.5 |
| 7125158 | 102.25 | 143.5 | 43.25 | 124 | 99.5 | 40.75 | 121.5 | 84 | 198.5 | 6938.25 | 63.25 | 154.25 |
| 8161710 | 135 | 166.25 | 69.25 | 130 | 110.75 | 74 | 160.5 | 211 | 335.5 | 5568 | 86 | 62 |
| 8963130 | 96.5 | 176.25 | 30 | 203.25 | 113.5 | 28.5 | 93 | 59 | 765 | 6945.5 | 60.5 | 64 |
| 9090819 | 122 | 103 | 64 | 161.25 | 177.25 | 52.5 | 199 | 65 | 491.25 | 11485.75 | 111.25 | 26.5 |
| 9305897 | 51.25 | 129.75 | 32 | 85 | 121.75 | 33.75 | 98.5 | 40.75 | 288.75 | 7645.5 | 51.5 | 9.5 |
| H10 | 91 | 24.5 | 12 | 99.25 | 51 | 16.5 | 153.25 | 13.5 | 248.5 | 3304.5 | 61.25 | 10.5 |
| H11 | 61.75 | 37.5 | 14 | 65.25 | 83.5 | 16.75 | 88 | 7.5 | 923.75 | 4263.75 | 41 | 12 |
| H7 | 55 | 24.5 | 20 | 74 | 42 | 13.25 | 130.25 | 15.75 | 165.5 | 385.25 | 65.5 | 11 |
| H8 | 41 | 27.25 | 11.5 | 47.5 | 35 | 9 | 61 | 10 | 549.75 | 778.25 | 27 | 11.5 |
| H9 | 23 | 20.5 | 13 | 59.5 | 22.75 | 13.25 | 101.25 | 11.5 | 264.5 | 458.75 | 36.5 | |

TABLE 2-continued

| Sample ID | MCP-1 | MCP-3 | TGF-b | TNF-A | MIG | TNF-B | MIP-1B | V-CAM-1 | MIP1a | VEGF | NGF | PAI-1 | PDGFBB | RANTES | Resistin | uresponder | SCF | sFAS ligan |
|---|---|---|---|---|---|---|---|---|---|---|---|---|---|---|---|---|---|---|
| 201292 | 25.5 | 128.25 | 57.25 | 89 | 84.5 | 29 | 795 | 8736.25 | 63.75 | 107.75 | 26.75 | 9771.5 | 6220.75 | 9241 | 6772 | 0 | 53 | 317.25 |
| 634246 | 862 | 40 | 38.5 | 14 | 77 | 5.5 | 300.25 | 5759.25 | 29 | 78.25 | 12.5 | 7039 | 5384 | 7148 | 5247.25 | 0 | 24.25 | 149 |
| 825371 | 49.5 | 68.25 | 88.75 | 61.75 | 75.5 | 14.5 | 761 | 10073.5 | 51 | 218.5 | 70 | 9904.5 | 5020 | 7629.5 | 5263 | 0 | 129.75 | 218.25 |
| 1030489 | 144.25 | 150 | 130.25 | 106 | 188.25 | 22.5 | 1309 | 3245.25 | 79.25 | 262.5 | 62 | 11177 | 7600 | 10247 | 6085.5 | 1 | 96.5 | 306.5 |
| 1141513 | 568.5 | 134 | 86 | 97.5 | 36.5 | 46.5 | 1023.5 | 11877.75 | 92 | 287.25 | 39.5 | 10807 | 7707 | 7699.25 | 8418.25 | 1 | 144.75 | 422 |
| 1326051 | 37 | 73 | 17.75 | 19.5 | 23.5 | 7.5 | 275.25 | 1129.5 | 18.25 | 25.5 | 12 | 4078 | 2995.25 | 4079.25 | 2980.5 | 0 | 21.5 | 63.5 |
| 2628013 | 110.5 | 115.25 | 98.75 | 103.25 | 153.5 | 22.25 | 785.5 | 10526.5 | 70.75 | 321 | 49 | 10443.25 | 5839.25 | 9729.25 | 6154 | 0 | 104.5 | 298 |
| 2889512 | 247.5 | 203 | 229.25 | 47.25 | 96.25 | 6.25 | 732.5 | 3710.75 | 34.75 | 830.75 | 47 | 8107.5 | 8324.75 | 8227.5 | 5767.25 | 1 | 78 | 95 |
| 3193413 | 22 | 72.25 | 92 | 57.75 | 32 | 39.5 | 638.75 | 10360.75 | 80.5 | 119.75 | 37.5 | 9635.5 | 5214.5 | 9180.5 | 4954.5 | 0 | 66.5 | 374.5 |
| 3256985 | 130 | 115.75 | 152.5 | 167.5 | 203.5 | 81 | 1856.75 | 12740.5 | 120 | 419.5 | 59.5 | 10678.5 | 7882 | 10719.5 | 9382.25 | 1 | 118 | 442.25 |
| 3514566 | 78 | 114 | 146.5 | 55.5 | 92 | 7.5 | 999.5 | 5502.5 | 37.25 | 129.25 | 43.75 | 10328.75 | 8531.25 | 9802 | 7018.5 | 0 | 29 | 99.75 |
| 3723343 | 93 | 107.25 | 124.25 | 16.5 | 223 | 6 | 1068 | 3545 | 28.5 | 422.75 | 34 | 8534.5 | 7517.5 | 8571 | 5009 | 0 | 58.75 | 122 |
| 3958469 | 136 | 217 | 278.5 | 19.5 | 101 | 4 | 1324 | 2670.5 | 21.75 | 454.5 | 89.5 | 9069.75 | 8442.5 | 8085.25 | 3618 | 1 | 68 | 101 |
| 4023341 | 144.25 | 109.5 | 129.5 | 124 | 256 | 33.75 | 1228.5 | 11194.75 | 78 | 237 | 67 | 10476.5 | 6155.5 | 9824.5 | 9030.5 | 0 | 169 | 341 |
| 4393232 | 125 | 87.25 | 108.75 | 65.75 | 86.25 | 27 | 731.25 | 12355.75 | 69 | 325.5 | 46.25 | 9948 | 7185.25 | 9935 | 7435.75 | 1 | 142 | 280 |
| 4812525 | 177.75 | 87.5 | 229.25 | 126.5 | 89.75 | 44 | 1007.25 | 12423 | 88.25 | 311 | 33.25 | 10481.25 | 8080 | 10990 | 9722.25 | 0 | 177.75 | 412 |
| 4924078 | 63.5 | 47.25 | — | 22 | 78 | 3.5 | 451 | 3669.25 | 18.5 | 80.5 | 14.5 | 3170.25 | 3852 | 8622 | 4453.25 | 1 | 34.75 | 107.75 |
| 5025882 | 266 | 108.75 | | | 164.5 | | 1110 | | 125 | | 178.5 | 10542.75 | 6806.75 | 9120.75 | 8487.25 | | 368.25 | 273.75 |
| 5661422 | 112.5 | 63.5 | | | 107.25 | | 231.25 | | 25.75 | | 12.5 | 7969 | 5808.5 | 4633.5 | 6157.5 | | 30.5 | 102.5 |
| 6043240 | 23.5 | 81.25 | | | 168.75 | | 343.75 | | 23 | | 88 | 8664.5 | 6868.75 | 7258.75 | 4490.5 | | 76 | 91.5 |
| 7037244 | 89 | 132 | | | 69.5 | | 871.75 | | 56.5 | | 59 | 10281.25 | 5376 | 8596.5 | 6288.25 | | 73 | 156.25 |
| 7125158 | 523.5 | 112.75 | | | 109.25 | | 770.75 | | 92.5 | | 52.75 | 10582 | 6351 | 10371 | 7864.75 | | 127 | 394 |
| 8161710 | 146.75 | 137.25 | | | 114 | | 1698.75 | | 136.5 | | 60 | 10231.5 | 5924.75 | 10025.5 | 8831 | | 150.5 | 640 |
| 8963130 | 83.25 | 95.5 | | | 319 | | 1523 | | 70.75 | | 37 | 9963.5 | 6058.25 | 9988.75 | 7885.5 | | 87.75 | 317 |
| 9090819 | 180.75 | 147.25 | | | 164.5 | | 586.25 | | 84 | | 74.75 | 7615.75 | 6935.25 | 9362.5 | 8132 | | 138 | 281 |
| 9305897 | 99 | 67.75 | | | 101.25 | | 973.25 | | 56 | | 49.25 | 6700.5 | 6257 | 9462.75 | 8567 | | 114 | 234 |
| H10 | 80 | 131.75 | | | 17 | | 218 | | 19.5 | | 62 | 8875.75 | 7068.5 | 7052 | 4636.5 | | 36.5 | 110.5 |
| H11 | 52 | 107.25 | | | 151.75 | | 189.5 | | 13.5 | | 34 | 7527 | 6475 | 7856 | 2954 | | 69.5 | 81.5 |
| H7 | 61.5 | 125.25 | | | 96.5 | | 730 | | 26.25 | | 49.75 | 4789.5 | 6321.75 | 7654.25 | 4295.5 | | 41.25 | 91 |
| H8 | 58 | 92.75 | | | 92.5 | | 153 | | 17.75 | | 29.5 | 8444.75 | 7014.75 | 7534 | 2958.25 | | 62.5 | 66.5 |
| H9 | 48 | 100 | | | 25.5 | | 490 | | 19.5 | | 46.25 | 8620.25 | 5254.5 | 7541.5 | 1657 | | 38.75 | 90 |

| Sample # | age onset | disease_d | gender | dob |
|---|---|---|---|---|
| 201292 | 19.67 | 0.58 | f | 17 Jun. 1982 |
| 634246 | 26.84 | 9.29 | f | 30 Aug. 1962 |
| 825371 | 47.3 | 2.79 | m | 28 May 1944 |
| 1030498 | 23.3 | 18.74 | m | 28 Mar. 1959 |
| 1141513 | 29.8 | 0.45 | f | 13 Feb. 1971 |
| 1326051 | 37.77 | 5.27 | f | 23 Jan. 1954 |
| 2628013 | 14.65 | 3.11 | f | 22 May 1985 |
| 2889512 | 47.44 | 2.87 | f | 24 May 1946 |
| 3193413 | 25.95 | 1.16 | f | 02 Feb. 1975 |
| 3256985 | 27.56 | 1.48 | f | 01 Jan. 1976 |
| 3514566 | 24.04 | 10.39 | f | 01 Jan. 1962 |
| 3723343 | 30.35 | 5.77 | f | 24 Jan. 1961 |
| 3958469 | 27.67 | 2.92 | f | 31 Oct. 1966 |
| 4023341 | 31.15 | 5.25 | f | 21 Mar. 1963 |
| 4393232 | 33.78 | 4.89 | f | 15 Jun. 1968 |
| 4812525 | 36.25 | 6.97 | m | 14 Mar. 1957 |
| 4924078 | 36.47 | 1.71 | f | 10 Jan. 1959 |

TABLE 2-continued

| Sample ID | IFNb treatment | | | | | | | | | | atreatment | IFN most u | | EDSS start |
|---|---|---|---|---|---|---|---|---|---|---|---|---|---|---|
| 5025882 | | 289.5 | 143.75 | 114.5 | 32.5 | 12738 | 440.25 | | | 18.33 | 10.82 | 0 | Rebif | m | 02 Feb. 1972 | 2 |
| 5661422 | | 45.25 | 55.25 | 40 | 6 | 5259.5 | 79.5 | | | 22.43 | 4.73 | 0 | Avonex | f | 11 Mar. 1969 | 5.5 |
| 6043240 | | 32.25 | 53 | 26 | 4 | 6410.5 | 95.5 | | | 27.35 | 5.21 | 1 | Rebif | f | 26 May 1964 | 2.5 |
| 7037244 | | 88 | 115.25 | 50.75 | 9.5 | 6540.5 | 206.75 | | | 22.57 | 1.48 | 0 | Avonex | f | 10 Jul. 1975 | 1 |
| 7125158 | | 201 | 91 | 114.5 | 57.5 | 10136.5 | 194 | | | 25.79 | 1.65 | 1 | Avonex | f | 17 Aug. 1973 | 3.5 |
| 8161710 | | 232.75 | 151 | 165.5 | 109.25 | 12735 | 268.25 | | | 17.95 | 2.27 | 0 | Avonex | f | 02 Jun. 1981 | 4 |
| 8963130 | | 237 | 79.5 | 73.5 | 27.5 | 11719 | 268 | | | 26.52 | 3.26 | 0 | Betaferon | f | 25 Jul. 1972 | 1 |
| 9090819 | | 148 | 154.75 | 155.5 | 24 | 10785.5 | 404.5 | | | 23.61 | 8.85 | 0 | Rebif | f | 04 Nov. 1969 | 6 |
| 9305897 | | 62.75 | 85 | 80.75 | 10.5 | 9602.5 | 208.25 | | | 38.21 | 1.55 | 1 | Rebif | f | 28 Apr. 1965 | 4 |
| H10 | | 33.5 | 124.25 | 31 | 2 | 2493.25 | 95 | | | | | healthy | | | | 3 |
| H11 | | 26 | 138.5 | 36 | 3 | 1727.5 | 261.5 | | | | | healthy | | | | 4.5 |
| H7 | | 47.5 | 107 | 46.5 | 3.75 | 3413.5 | 191.5 | | | | | healthy | | | | 3.5 |
| H8 | | 22 | 55.5 | 26 | 4.75 | 2259.75 | 117.5 | | | | | healthy | | | | 1.5 |
| H9 | | 63.5 | 65 | 15 | 4 | 2067.5 | 151.25 | | | | | healthy | | | | 2 |

| Sample ID | IFNb treatment | | doo | dod | relapse rate | ivmp 2 yrs | | relapse rate | ivmp 2 yrs | atreatment | IFN most u | EDSS start |
|---|---|---|---|---|---|---|---|---|---|---|---|---|
| 201292 | 16.09.02 | | 15.02.2002 | 15.06.2002 | 2 | 0 | | 2 | 2 | 17 | Rebif | 2 |
| 634246 | 15.10.98 | | 01.07.1989 | 01.07.1989 | 3 | 3 | | 2 | 1 | 12 | Avonex | 5.5 |
| 825371 | 01.07.94 | | 15.09.1991 | 01.10.1993 | 1 | 1 | | 1 | 2 | 174 | Rebif | 2.5 |
| 1030489 | 09.04.01 | | 15.07.1982 | 15.07.1982 | 1 | 0 | | 0 | 0 | 77 | Avonex | 1 |
| 1141513 | 15.05.01 | | 01.12.2000 | 01.02.2001 | 1 | | | 0 | | 46 | Avonex | 3.5 |
| 1326051 | 06.02.97 | | 01.11.1991 | 01.07.1992 | 3 | | | 2 | | 56 | Avonex | 4 |
| 2628013 | 24.02.03 | | 15.01.2000 | 15.07.2000 | 2 | | | 1 | 1 | 70 | Avonex | 1 |
| 2889512 | 15.09.96 | | 01.11.1993 | 01.04.1995 | 3 | 2 | | 0 | 0 | 147 | Betaferon | 6 |
| 3193413 | 13.05.02 | | 15.03.2001 | 05.03.2002 | 3 | 1 | | 0 | 2 | 35 | Rebif | 4 |
| 3256985 | 17.01.05 | | 26.07.2003 | 15.08.2003 | 2 | 2 | | 0 | 1 | 36 | Rebif | 3 |
| 3514566 | 07.06.96 | | 15.01.1986 | 29.01.1986 | 3 | | | 2 | 1 | 150 | Betaferon | 4.5 |
| 3723343 | 10.03.97 | | 01.06.1991 | 01.07.1991 | 2 | 1 | | 2 | 2 | 121 | Rebif | 3.5 |
| 3958469 | 02.06.97 | | 01.01.1994 | 22.01.1997 | 1 | 0 | | 1 | 0 | 130 | Betaferon | 1.5 |
| 4023341 | 15.08.99 | | 15.05.1994 | 15.05.1994 | 1 | | | 2 | | 112 | Avonex | 2 |
| 4393232 | 31.01.05 | | 15.02.2002 | 15.01.2003 | 3 | | | 0 | | | Betaferon | 3 |
| 4812525 | 03.06.00 | | 15.06.1993 | 19.05.1998 | 2 | 0 | | 2 | 0 | 96 | Rebif | 1 |
| 4924078 | 15.03.97 | | 01.07.1995 | 25.06.1996 | 4 | 0 | | 0 | 0 | 141 | Betaferon | 2 |
| 5025882 | 26.03.01 | | 01.06.1990 | 06.08.1998 | 2 | 1 | | 2 | 3 | 93 | Avonex | 3.5 |
| 5661422 | 06.05.96 | | 15.08.1991 | 15.10.1994 | 5 | 3 | | 3 | 3 | 37 | Betaferon | 5.5 |
| 6043240 | 15.12.96 | | 01.10.1991 | 22.04.1992 | 2 | | | 0 | | 46 | Betaferon | 3.5 |
| 7037244 | 26.07.99 | | 01.02.1998 | 03.07.1998 | 3 | 0 | | 2 | 2 | 47 | Rebif | 5 |
| 7125158 | 22.01.01 | | 01.06.1999 | 01.12.2000 | 2 | 0 | | 0 | 0 | 95 | Avonex | 2 |
| 8161710 | 20.08.01 | | 15.05.1999 | 15.07.2001 | 3 | 3 | | 3 | 3 | 50 | Rebif | 2.5 |
| 8963130 | 06.05.02 | | 01.02.1999 | 01.08.1999 | 1 | 1 | | 1 | 1 | 39 | Rebif | 2 |
| 9090819 | 22.04.02 | | 15.06.1993 | 11.05.1999 | 0 | 2 | | 2 | 2 | 80 | Avonex | 2 |
| 9305897 | 31.01.05 | | 15.07.2003 | 19.08.2004 | 2 | 0 | | 0 | 0 | 26 | Rebif | 2 |
| H10 | | | | | | | | | | | | |
| H11 | | | | | | | | | | | | |
| H7 | | | | | | | | | | | | |
| H8 | | | | | | | | | | | | |
| H9 | | | | | | | | | | | | |

The p values of the analytes from each test are shown in Table 3. It is noted that the p values in these analyses may be made stronger with increasing sample size.

TABLE 3

| | GENBANK ACCESSION # | p_anova | p_kw |
|---|---|---|---|
| ENA78/CXCL5 (epithelial-derived neutrophil-activating peptide 78) | CAG33709 | 0.113 | 0.032 |
| Eotaxin1/CCL11 | EAW80209 | 0.722 | 0.957 |
| FGFb/FGF2/HBGH-2/fibroblast growth factor 2 basic/heparin-binding growth factor 2 | NP_001997 | 0.041 | 0.052 |
| G-CSF/CSF3 Granulocyte Colony-stimulating factor | CAG46689 | 0.215 | 0.383 |
| GM-CSF Granulocyte-macrophage colony-stimulating factor | AAA52578 | 0.714 | 0.889 |
| Gro-Alpha/CXCL1 | AAP13103 | 0.467 | 0.19 |
| HGF/Hepatocyte growth factor | AAA64297 | 0.192 | 0.226 |
| ICAM1/Intercellular adhesion molecule 1 | NP_000192 | 0.391 | 0.059 |
| IFN-α2/Interferon alpha 2 | CAA72532 | 0.015 | 0.023 |
| IFN-β/Interferon-beta | AAC41702 | 0.504 | 0.474 |
| IFN-γ/Interferon-gamma | NP_000610 | 0.355 | 0.231 |
| IL-10/Interleukin 10 | CAG46825 | 0.844 | 0.429 |
| IL-12p40/interleukin-12 subunit beta | NP_002178 | 0.822 | 0.838 |
| IL-12p70/Interleukin-12 p 70: dimer of p40(NP_002178) and p35 | NP_000873 | 0.387 | 0.394 |
| IL-13/interleukin-13 | AAH96140 | 0.856 | 0.895 |
| IL-15/interleukin-15 | CAG46804 | 0.309 | 0.702 |
| IL-17A/interleukin-17A | NP_002181 | 0.345 | 0.343 |
| IL-17F/interleukin-17F | NP_443104 | 0.505 | 0.384 |
| IL-18/interleukin-18 | CAG46798 | 0.179 | 0.197 |
| IL-1alpha/interleukin-1 alpha | CAG33695 | 0.96 | 0.622 |
| IL-1B/interleukin-1 beta | AAH08678 | 0.701 | 0.609 |
| IL-1RA/interleukin receptor antagonist: | CAA36262 | 0.025 | 0.026 |
| IL-2/interleukin 2 | AAA59140 | 0.033 | 0.049 |
| IL-4/interleukin 4 | AAH70123 | 0.366 | 0.369 |
| IL-5/interleukin 5 | NP_000870 | 0.423 | 0.588 |
| IL-6/interleukin 6 | CAG29292 | 0.033 | 0.001 |
| IL-7/interleukin 7 | AAC63047 | 0.997 | 0.86 |
| IL-8/interleukin 8 | CAG46948 | 0.04 | 0.027 |
| IP10/CXCL10/Interferon gamma-induced protein 10 | NP_001556 | 0.904 | 0.758 |
| Leptin | AAH69323 | 0.622 | 0.792 |
| LIF/leukemia inhibitory factor | AAA51699 | 0.928 | 0.784 |
| M-CSF/Macrophage colony-stimulating factor | AAA59573 | 0.005 | 0.004 |
| MCP-1/CCL2/monocyte chemotactic protein-1 | NP_002973 | 0.027 | 0.024 |
| MCP-3/CCL7/monocyte-specific chemokine 3 | AAH92436 | 0.96 | 0.777 |
| MIG/CXCL9/Monokine induced by gamma interferon | NP_002407 | 0.98 | 0.893 |
| MIP-1B/CCL4/Macrophage inflammatory protein-1β | AAI04228 | 0.082 | 0.126 |
| MIP-1a/CCL3/Macrophage inflammatory protein-1α | AAH71834 | 0.006 | 0.01 |
| NGF/Nerve growth factor | CAA37703 | 0.887 | 0.816 |
| PAI-1/SERPINE1/Plasminogen activator inhibitor-1 | AAH10860 | 0.375 | 0.196 |
| PDGFBB/Platelet-derived growth factor subunit B | CAG46606 | 0.623 | 0.407 |
| RANTES/CCL5/Regulated upon Activation, Normal T-cell Expressed, and Secreted | AAH08600 | 0.285 | 0.28 |
| Resistin/adipose tissue-specific secretory factor (ADSF)/C/EBP-epsilon-regulated myeloid-specific secreted cysteine-rich protein (XCP1) | NP_001180303 | 0.203 | 0.142 |
| SCF/Stem Cell Factor | AAB35922 | 0.209 | 0.225 |
| sFAS ligand/Fas ligand/FasL | AAC50071 | 0.003 | 0.004 |
| TGF-a/Transforming Growth Factor Alpha | AAA61159 | 0.062 | 0.022 |
| TGF-b/Transforming Growth Factor Beta | NP_000651 | 0.574 | 0.952 |
| TNF-A/Tumor necrosis factor | CAA78745 | 0.085 | 0.043 |
| TNF-B/LTA/Lymphotoxin-alpha | CAA78746 | 0.006 | 0.009 |
| VCAM/Vascular cell adhesion protein 1 | AAA61269 | 0.138 | 0.116 |
| VEGF/Vascular endothelial growth factor | CAC19513 | 0.836 | 0.963 |

We performed the analysis using the analyte values both on their original scale and also on a log transformed scale. Log transformation may produce more normal distributions, which are helpful for parametric analyses such as ANOVA. The analysis results were largely consistent whether we analyzed on the original scale or on the log transformed scale.

There are 11 analytes that differed significantly across the 3 treatment groups before treatment was given (at baseline). Analytes that differed significantly across the 3 treatment groups before treatment are shown in Table 4.

TABLE 4

| Analyte | P value anova | P value Kruskal Wallis |
|---|---|---|
| sFAS.ligand | 0.003 | 0.004 |
| M.CSF | 0.005 | 0.004 |
| MIP1a | 0.006 | 0.01 |
| TNF.B | 0.006 | 0.009 |
| IFN.a | 0.015 | 0.023 |
| IL.1RA | 0.025 | 0.026 |
| MCP.1 | 0.027 | 0.024 |
| IL.2 | 0.033 | 0.049 |
| IL.6 | 0.033 | 0.001 |
| IL.8 | 0.04 | 0.027 |
| FGFb | 0.041 | 0.052 |

Example 4

We next compared pre-treatment analyte levels in responders versus non-responders using a t-test to determine if analyte values differed between responders and non-responders. The t-test is a special case of ANOVA when there are only two values of the categorical variable (responder/non-responder). See Glantz, supra. Table 5 shows the p-values of the analytes as determined by t-test.

TABLE 5

| Analyte | p_ttest | CI_ttest.1 | CI_ttest.2 |
|---|---|---|---|
| PDGFBB | 0.015374 | −2284.59 | −266.669 |
| IL.7 | 0.028474 | −91.8783 | −5.58599 |
| TGF.b | 0.063443 | −83.9913 | 2.467461 |
| IFN.b | 0.080245 | −65.3494 | 1070.79 |
| IL.13 | 0.08365 | −35.1825 | 2.355128 |
| IL.17F | 0.085865 | −64.4635 | 911.6778 |
| EOTAXIN | 0.086362 | −418.893 | 29.96899 |
| IL.1a | 0.089047 | −65.729 | 4.996873 |
| MCP.3 | 0.098099 | −60.6014 | 5.488308 |
| LIF | 0.146334 | −36.1731 | 5.708798 |
| VEGF | 0.208181 | −223.061 | 51.19174 |
| IL.5 | 0.296316 | −48.5198 | 15.43647 |
| TGF.a | 0.29787 | −159.233 | 498.1854 |
| IL.1B | 0.300051 | −43.1399 | 13.878 |
| LEPTIN | 0.307564 | −4115.91 | 1353.317 |
| IL.8 | 0.311607 | −31.118 | 93.55845 |
| RANTES | 0.319789 | −2021 | 687.6705 |
| IL.12.P70 | 0.337475 | −20.4104 | 7.279434 |
| IL.6 | 0.359357 | −210.853 | 559.7814 |
| IL.17 | 0.399055 | −36.3172 | 14.97795 |
| IFN.a | 0.41062 | −16.4768 | 38.97675 |
| GM.CSF | 0.435472 | −182.542 | 410.4056 |
| IL.12P40 | 0.484255 | −109.784 | 225.0457 |
| V.CAM.1 | 0.492394 | −2041.89 | 4125.04 |
| ENA78 | 0.518156 | −456.282 | 881.3476 |
| sFAS.ligand | 0.575165 | −85.4454 | 150.368 |
| ICAM.1 | 0.60113 | −2412.46 | 4078.667 |
| NGF | 0.640608 | −34.0582 | 21.3618 |
| GRO.ALPHA | 0.652072 | −24.4468 | 15.58969 |
| MCP.1 | 0.656315 | −194.146 | 124.5623 |
| IL.2 | 0.67596 | −22.3306 | 33.84845 |
| PAI.1 | 0.681899 | −1332.55 | 2003.119 |
| SCF | 0.701381 | −47.7067 | 69.80198 |

TABLE 5-continued

| Analyte | p_ttest | CI_ttest.1 | CI_ttest.2 |
|---|---|---|---|
| MIP1a | 0.704577 | −22.8849 | 33.33731 |
| MIG | 0.753942 | −49.5531 | 67.54119 |
| TNF.B | 0.765154 | −18.1007 | 24.30906 |
| M.CSF | 0.771988 | −25.8778 | 34.44329 |
| MIP.1B | 0.784956 | −398.082 | 304.1893 |
| G.CSF | 0.801559 | −20.8131 | 26.65836 |
| IFN.G | 0.816049 | −30.1689 | 23.99626 |
| TNF.A | 0.8204 | −43.4463 | 34.74984 |
| IL.4 | 0.850446 | −36.9998 | 30.74389 |
| Resistin | 0.850806 | −1684.56 | 1400.369 |
| IL.1RA | 0.854994 | −34.4234 | 41.19128 |
| IP10 | 0.859147 | −336.002 | 399.966 |
| FGFb | 0.869545 | −20.2798 | 23.82744 |
| HGF | 0.871704 | −257.452 | 219.7136 |
| IL.18 | 0.93563 | −66.7212 | 72.21522 |
| IL.15 | 0.953459 | −14.8909 | 14.06352 |
| IL.10 | 0.974916 | −24.5552 | 25.32305 |

Two analytes, PDGF BB and IL-7, have significant p-values for discriminating responders from non-responders by t-test. Table 6 shows the p-values of the top 10 analytes for discriminating responder from non-responder (t-test).

TABLE 6

| Analyte | p-value t-test |
|---|---|
| PDGFBB | 0.015 |
| IL.7 | 0.028 |
| TGF.b | 0.063 |
| IFN.b | 0.080 |
| IL.13 | 0.084 |
| IL.17F | 0.086 |
| EOTAXIN | 0.086 |
| IL.1a | 0.089 |
| MCP.3 | 0.098 |
| LIF | 0.146 |

Example 5

We next performed a chi-square test to determine if there is an association between treatment group and response/non-response. See Glantz, supra. The chi-square test is a test of association between two categorical variables, in this case treatment group (Avonex, Betaferon, or Rebif) with and without response (responder/non-responder). We found a significant association (p-value=0.02772). See Table 5 and Table 7.

TABLE 7

|  | Non-Responders | Responders |
|---|---|---|
| Avonex | 5 | 4 |
| Betaferon | 1 | 6 |
| Rebif | 8 | 2 |

Example 6

We next quantified the ability of individual analytes to discriminate between responder/non-responder using the area under the ROC curve (AUROC). The AUROC is a measure of the ability of an analyte to identify responder versus non-responder. The area under the ROC curve (AUROC) is described in standard texts on statistics for diagnostic tests such as Pepe 2004: The Statistical Evaluation of Medical Tests for Classification and Prediction (Oxford Statistical Science Series) by Margaret Sullivan Pepe, Oxford University Press, USA; 1 edition (Dec. 16, 2004); ISBN-13: 978-0198565826, herein incorporated by reference. Table 8 shows the AUROC for the analytes.

TABLE 8

| analyte | roc_area |
|---|---|
| PDGFBB | 0.833333 |
| IL.7 | 0.708333 |
| IL.1a | 0.702381 |
| IL.13 | 0.681548 |
| EOTAXIN | 0.678571 |
| MCP.3 | 0.672619 |
| NGF | 0.672619 |
| IFN.b | 0.666667 |
| TGF.b | 0.666667 |
| IL.17F | 0.660714 |
| LIF | 0.651786 |
| IL.5 | 0.645833 |
| IL.10 | 0.639881 |
| TGF.a | 0.625 |
| VEGF | 0.619048 |
| IL.17 | 0.610119 |
| MCP.1 | 0.610119 |
| ICAM.1 | 0.607143 |
| IFN.G | 0.60119 |
| IL.1B | 0.60119 |
| LEPTIN | 0.60119 |
| GM.CSF | 0.598214 |
| IL.12.P70 | 0.589286 |
| RANTES | 0.589286 |
| IP10 | 0.577381 |
| V.CAM.1 | 0.577381 |
| TNF.B | 0.574405 |
| HGF | 0.571429 |
| sFAS.ligand | 0.571429 |
| IL.6 | 0.565476 |
| IFN.a | 0.559524 |
| M.CSF | 0.559524 |
| IL.8 | 0.550595 |
| MIG | 0.550595 |
| IL.4 | 0.547619 |
| IL.15 | 0.544643 |
| GRO.ALPHA | 0.53869 |
| IL.2 | 0.535714 |
| SCF | 0.535714 |
| TNF.A | 0.529762 |
| MIP1a | 0.52381 |
| IL.1RA | 0.517857 |
| ENA78 | 0.517857 |
| PAI.1 | 0.517857 |
| FGFb | 0.511905 |
| G.CSF | 0.511905 |
| MIP.1B | 0.505952 |
| IL.12P40 | 0.5 |
| IL.18 | 0.5 |
| Resistin | 0.5 |

Table 9 shows the area under the ROC curve for the top 10 analytes.

TABLE 9

| analyte | ROC area |
|---|---|
| PDGFBB | 0.833333333 |
| IL.7 | 0.708333333 |
| IL.1a | 0.702380952 |
| IL.13 | 0.681547619 |
| EOTAXIN | 0.678571429 |
| MCP.3 | 0.672619048 |
| NGF | 0.672619048 |
| IFN.b | 0.666666667 |
| TGF.b | 0.666666667 |

We also examined the association of pre-treatment analytes with response/non-response in linear regression models that included treatment group as a covariate, to see which analytes are significant predictors of response after controlling for treatment group. See Table 10.

TABLE 10

| | p.analyte | p.Avonex | p.Betaferon |
|---|---|---|---|
| RANTES | 0.048 | 0.129 | 0.093 |
| IL.5 | 0.055 | 0.192 | 0.059 |
| IL.7 | 0.061 | 0.365 | 0.079 |
| MIP.1B | 0.064 | 0.09 | 0.066 |
| PDGFBB | 0.065 | 0.226 | 0.156 |
| IL.13 | 0.083 | 0.277 | 0.09 |
| IL.12.P70 | 0.092 | 0.273 | 0.063 |
| HGF | 0.098 | 0.296 | 0.051 |
| IL.17 | 0.105 | 0.354 | 0.06 |
| IL.1B | 0.113 | 0.289 | 0.084 |
| IL.1a | 0.114 | 0.403 | 0.101 |
| TGF.b | 0.129 | 0.209 | 0.144 |
| LIF | 0.132 | 0.306 | 0.087 |
| NGF | 0.138 | 0.318 | 0.086 |
| IL.15 | 0.143 | 0.165 | 0.084 |
| EOTAXIN | 0.143 | 0.331 | 0.136 |
| VEGF | 0.145 | 0.222 | 0.095 |
| MCP.3 | 0.146 | 0.348 | 0.092 |
| TNF.A | 0.148 | 0.284 | 0.062 |
| FGFb | 0.161 | 0.213 | 0.054 |
| IFN.G | 0.168 | 0.328 | 0.066 |
| MIP1a | 0.168 | 0.24 | 0.058 |
| IL.2 | 0.169 | 0.33 | 0.058 |
| M.CSF | 0.173 | 0.207 | 0.049 |
| GRO.ALPHA | 0.175 | 0.284 | 0.081 |
| sFAS.ligand | 0.179 | 0.179 | 0.058 |
| LEPTIN | 0.184 | 0.179 | 0.112 |
| ENA78 | 0.185 | 0.376 | 0.059 |
| IL.1RA | 0.185 | 0.191 | 0.065 |
| Resistin | 0.187 | 0.21 | 0.069 |
| IFN.b | 0.195 | 0.196 | 0.213 |
| IL.10 | 0.201 | 0.263 | 0.086 |
| SCF | 0.209 | 0.306 | 0.068 |
| TNF.B | 0.236 | 0.214 | 0.059 |
| IL.4 | 0.239 | 0.279 | 0.075 |
| IL.17F | 0.269 | 0.232 | 0.188 |
| MCP.1 | 0.296 | 0.68 | 0.072 |
| IL.18 | 0.429 | 0.26 | 0.092 |
| IFN.a | 0.439 | 0.274 | 0.086 |
| G.CSF | 0.465 | 0.194 | 0.122 |
| GM.CSF | 0.474 | 0.224 | 0.112 |
| IP10 | 0.507 | 0.251 | 0.107 |
| V.CAM.1 | 0.52 | 0.219 | 0.097 |
| IL.8 | 0.55 | 0.271 | 0.096 |
| MIG | 0.689 | 0.258 | 0.112 |
| PAI.1 | 0.736 | 0.249 | 0.11 |
| ICAM.1 | 0.833 | 0.265 | 0.131 |
| IL.12P40 | 0.883 | 0.261 | 0.118 |
| IL.6 | 0.939 | 0.265 | 0.162 |
| TGF.a | 0.968 | 0.262 | 0.146 |

Table 11 shows the p-values for analytes after controlling for treatment group.

TABLE 11

| | p.analyte | p.Avonex | p.Betaferon |
|---|---|---|---|
| RANTES | 0.048 | 0.129 | 0.093 |
| IL.5 | 0.055 | 0.192 | 0.059 |
| IL.7 | 0.061 | 0.365 | 0.079 |
| MIP.1B | 0.064 | 0.09 | 0.066 |
| PDGFBB | 0.065 | 0.226 | 0.156 |
| IL.13 | 0.083 | 0.277 | 0.09 |
| IL.12.P70 | 0.092 | 0.273 | 0.063 |
| HGF | 0.098 | 0.296 | 0.051 |

Example 8

Quantitation of IL-7

Quantitation of IL-7 is of particular interest. As shown in FIGS. 22-25, determination of these cytokine levels distinguishes individuals who have a high probability of responsiveness to a therapy from those who have a low probability of responsiveness. Assessment in a patient thus allows improved care, where patients classified as a responder, who have high levels of circulating IL-7, and who have low levels of circulating IL-17, can be treated with an appropriate agent, e.g. β-IFN, while patients classified as a non-responder can be treated with alternative agents. Patients can be classified upon initial presentation of symptoms, and can be further monitored for status over the course of the disease to maintain appropriate therapy.

Example 9

Trial for Assessing Cytokine Profiles in RRMS

In a small cohort of 26 patients with RRMS, it was found that high serum levels of IL-17F and IFN-β prior to the initiation of IFN-β treatment were associated with non-responsiveness to therapy (see Axtell et al. (2010) *Nature Med*, 16:406-412). These findings are verified in a larger, appropriately powered independent cohort. Further, the effects of therapy on cytokine levels in a longitudinal study of RRMS patients treated with IFN-β are examined. It is determined whether IL-17F levels change as therapy progresses and if treatment failures correlate with changes in IL-17F. Initial data has identified high levels of IL-7 that are predictive of a good response to IFN-β. Cytokines of interest for analysis also include PDGFBB, IL13 and eotaxin. Methods for assessment of patient outcomes are described previously in the instant specification. Study design and analysis include the methods set forth in PRISMS (Prevention of Relapses and Disability by Interferon β-1a Subcutaneously in Multiple Sclerosis) Study Group, Lancet 1998; 352: 1498-504; Kappos et al. N Engl J Med 2010; 362:387-401; Segal et al. *Lancet Neurol* 2008; 7: 796-804; Kappos et al. *Lancet* 2008; 372: 1463-72; and Mikol et al. *Lancet Neurol* 2008; 7: 903-14.

Study Oversight.

Steering-committee members develop the protocol and monitor the ongoing study. Data are collected by the investigators.

Patients.

Key eligibility criteria are an age of 18 to 55 years; a diagnosis of multiple sclerosis, according to the revised McDonald criteria16; a relapsing-remitting course; one or more documented relapses in the previous year or two or more in the previous 2 years; and a score of 0 to 5.5 on the Expanded Disability Status Scale (EDSS; which ranges from 0 to 10, with higher scores indicating greater disability).

Key exclusion criteria are relapse or corticosteroid treatment within 30 days before randomization, active infection, macular edema, diabetes mellitus, immune suppression (drug- or disease-induced), or clinically significant systemic disease.

The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Determination of Cytokine Profiles Prior to and During IFN-β Therapy in RRMS.

The initial finding that that high serum levels of IL-17F and IFN-β prior to the initiation of IFN-β treatment were associated with non-responsiveness to therapy is confirmed in a larger independent cohort containing at least 41 patients who are β-IFN non-responders. A determination of IL-7 levels, for example as shown in FIGS. 22-25, is also performed.

Study Design.

To ensure that all assessments remained unbiased regarding the study-group assignments (i.e., unaffected by awareness of them), an independent, specially trained and certified examining neurologist determined all the EDSS scores; this examining neurologist or a trained technician administered the Multiple Sclerosis Functional Composite (MSFC; comprising the average of the scores on the timed 25-foot walk, the 9-hole peg test, and the paced auditory serial-addition test with a 3-second interstimulus interval, with each converted to a z score [with the combined study population at baseline as the reference population], with higher scores representing improvement). Another independent physician monitored patients for 6 or more hours after administration of the first dose of the study drug. MRI scans are analyzed at a central MRI evaluation center by radiologists who are unaware of the study-group assignments, and an independent data and safety monitoring board evaluated the safety and overall benefit-risk profiles.

Experimental Procedure.

Blood is drawn prior to institution of therapy with the approved IFN-β preparations. Every six months over the next 24 months, a patient will undergo a venipuncture to obtain serum for multiplex determination of the 28 analytes on the Luminex bead system, as described in Example 1. Power calculations indicate that 41 patients who are non-responders will be required. It has been found that 'high IL-17F' is seen in approximately 25%-33% of patients with RRMS seen in the Stanford clinics, therefore 120 patients from the clinics will be screened and followed.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. Usa* 95, 14863-14868. The data is clustered with Tree View, as described by Axtell et al, supra.

Clinical assessments are performed at screening and at randomization (baseline), and study visits, including safety assessments, are scheduled after randomization. The primary end point was the annualized relapse rate, defined as the number of confirmed relapses per year. Relapses are verified by the examining neurologist within 7 days after the onset of symptoms. To constitute a confirmed relapse, the symptoms must have been accompanied by an increase of at least half a point in the EDSS score, of one point in each of two EDSS functional system scores, or of two points in one EDSS functional-system score (excluding scores for the bowel-bladder or cerebral functional systems).

The key secondary end point was the time to confirmed disability progression, defined as an increase of one point in the EDSS score (or half a point if the baseline EDSS score was equal to 5.5), confirmed after 3 months, with an absence of relapse at the time of assessment and with all EDSS scores measured during that time meeting the criteria for disability progression. Other secondary end points included the time to a first relapse, time to disability progression (confirmed after 6 months), changes in the EDSS score and MSFC z score between baseline and 24 months, number of gadolinium-enhancing lesions, proportion of patients free from gadolinium-enhancing lesions, number of new or enlarged lesions on T2-weighted MRI scans, proportion of patients free from new or enlarged lesions on T2-weighted scans, volumes of hyperintense lesions on T2-weighted scans and hypointense lesions on T1-weighted scans, change in brain volume between baseline and 24 months, and safety and tolerability measures. Specifications of the adverse-event monitoring procedure, as defined in the study protocol, are the same as those in TRANSFORMS.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9, with a sample size of 41 or more per group, for a result with significance of 0.035. A sample size of 100 is obtainable in a small multi-center trial and would increase the power of the trial.

Power and Sample Size estimates for One ROC Curve Power Analysis. The table below shows the required sample size for each of two groups (N+ and N−) and the corresponding power to show that the area under the ROC curve for the biomarkers is significantly better than chance (AUC=0.5).

Numeric Results for Testing AUC0=AUC1 with Continuous Data Test Type=Two-Sided. FPR1=0.0. FPR2=1.0. B=1.000. Allocation Ratio=1.000

| Power | N+ | N− | AUC0' | AUC1' | Diff | AUC0 | AUC1 | Diff | Alpha | Beta |
|---|---|---|---|---|---|---|---|---|---|---|
| 0.90044 | 172 | 172 | 0.5000 | 0.6000 | 0.1000 | 0.5000 | 0.6000 | 0.1000 | 0.05000 | 0.09956 |
| 0.80034 | 129 | 129 | 0.5000 | 0.6000 | 0.1000 | 0.5000 | 0.6000 | 0.1000 | 0.05000 | 0.19966 |
| 0.90219 | 75 | 75 | 0.5000 | 0.6500 | 0.1500 | 0.5000 | 0.6500 | 0.1500 | 0.05000 | 0.09781 |
| 0.80568 | 57 | 57 | 0.5000 | 0.6500 | 0.1500 | 0.5000 | 0.6500 | 0.1500 | 0.05000 | 0.19432 |
| 0.90457 | 41 | 41 | 0.5000 | 0.7000 | 0.2000 | 0.5000 | 0.7000 | 0.2000 | 0.05000 | 0.09543 |
| 0.80322 | 31 | 31 | 0.5000 | 0.7000 | 0.2000 | 0.5000 | 0.7000 | 0.2000 | 0.05000 | 0.19678 |
| 0.90496 | 25 | 25 | 0.5000 | 0.7500 | 0.2500 | 0.5000 | 0.7500 | 0.2500 | 0.05000 | 0.09504 |
| 0.80052 | 19 | 19 | 0.5000 | 0.7500 | 0.2500 | 0.5000 | 0.7500 | 0.2500 | 0.05000 | 0.19948 |

See Hanley, J. A. and McNeil, B. J. 1983. 'A Method of Comparing the Areas under Receiver Operating Characteristic Curves Derived from the Same Cases.' Radiology, 148, 839-843. September, 1983; Obuchowski, N. and McClish, D. 1997. 'Sample Size Determination for Diagnostic Accuracy Studies Involving Binormal ROC Curve Indices.' Statistics in Medicine, 16, pages 1529-1542.

Report Definitions

Power is the probability of rejecting a false null hypothesis.
N+ is the sample size from the positive (diseased) population.
N− is the sample size from the negative (non-diseased) population.
Alloc Ratio is the Sample Allocation Ratio (R=N−/N+).
AUC0' is the adjusted area under the ROC curve under the null hypothesis.
AUC1' is the adjusted area under the ROC curve under the alternative hypothesis.
Diff' is AUC1−'AUC0. This is the adjusted difference to be detected.
AUC0 is the actual area under the ROC curve under the null hypothesis.
AUC1 is the actual area under the ROC curve under the alternative hypothesis.
Diff is AUC1−AUC0. This is the difference to be detected.
Alpha is the probability of rejecting a true null hypothesis.
Beta is the probability of accepting a false null hypothesis.
FPR1, FPR2 are the lower and upper bounds on the false positive rates.
B is the ratio of the standard deviations of the negative and positive groups.

Summary Statements. A sample of 172 from the positive group and 172 from the negative group achieve 90% power to detect a difference of 0.1000 between the area under the ROC curve (AUC) under the null hypothesis of 0.5000 and an AUC under the alternative hypothesis of 0.6000 using a two-sided z-test at a significance level of 0.05000. The data are continuous responses. The AUC is computed between false positive rates of 0.000 and 1.000. The ratio of the standard deviation of the responses in the negative group to the standard deviation of the responses in the positive group is 1.000.

A sample of 129 from the positive group and 129 from the negative group achieve 80% power to detect a difference of 0.1000 between the area under the ROC curve (AUC) under the null hypothesis of 0.5000 and an AUC under the alternative hypothesis of 0.6000 using a two-sided z-test at a significance level of 0.05000. The data are continuous responses. The AUC is computed between false positive rates of 0.000 and 1.000. The ratio of the standard deviation of the responses in the negative group to the standard deviation of the responses in the positive group is 1.000.

The aggregate annualized relapse rate was estimated by means of a negative binomial regression model with adjustment for study group, country, number of relapses within 2 years before baseline, and EDSS score at baseline. The time to relapse or progression was estimated with the use of the Kaplan-Meier method. The times to disability progression (confirmed after 3 or 6 months) are compared in the main analysis by means of the log-rank test and in the supportive analysis by means of a Cox proportional-hazards model with adjustment for study group, country, baseline EDSS score, and age.

Clinical Classification and Serum Collection of Subjects with Multiple Sclerosis.

82 or more RRMS patients will be identified at the Stanford MS Clinic. Patients with RRMS receiving IFN-β treatment for at least 12 months as responders or nonresponders to IFN-β therapy will be studied. Two neurologists, blinded to the laboratory data, will classify the patients as responder or nonresponder on the basis of the Expanded Disability Status Scale progression, the number of relapses and steroid interventions in the 2 years before initiation of treatment compared to the 2 years after starting treatment. This is the protocol in Axtell et al, supra. Serum samples will be obtained the day before starting IFN-β therapy Example 10

Trial for Assessing Cytokine Profiles in Secondary Progressive Multiple Sclerosis (SPMS)

The association of biomarkers, including biomarkers associated with Th17 cells, with development of Secondary Progressive Multiple Sclerosis (SPMS) and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes and study design are described previously in the instant specification, in Example 9. Study design and analysis include the methods set forth in European Study Group on Interferon β-1b in Secondary Progressive MS, Lancet 1998; 352: 1491-97

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. Usa* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 11

Trial for Assessing Cytokine Profiles in Primary Progressive Multiple Sclerosis (PPMS)

The association of biomarkers, including biomarkers associated with Th17 cells, with development of Primary Progressive Multiple Sclerosis (PPMS) and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification, and in Example 9. Study design and analysis include the methods set forth in Hawker et al. Ann Neurol 2009; 66:460-471.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. Usa* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 12

Trial for Assessing Cytokine Profiles in Neuromyelitis Optica (NMO)

The association of biomarkers, including biomarkers associated with Th17 cells, with development of Neuromyelitis Optica (NMO) and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification, and in Kira (2010) Pathophysiology, "Neuromyelitis optica and opticospinal multiple sclerosis: Mechanisms and pathogenesis." Study design and analysis include the methods set forth in Jacob et al. ARCH NEUROL/VOL 65 (NO. 11), November 20; 1443.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) Nature Medicine, 8:295-301; Robinson et al. (2003) Nature Biotechnology, 21:1033-9; Ousman et al. (2007) Nature 448:474-479; Han et al. (2008) Nature, 451:1076-1081; and Eisen et al. (1998) Proc. Natl. Acad. Sci. Usa 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 13

Trial for Assessing Cytokine Profiles in Psoriasis

The association of biomarkers, including biomarkers associated with Th17 cells, with development of Psoriasis and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Papp et al. Lancet 2008; 371: 1675-84; Leonardi et al. Lancet 2008; 371: 1665-74; and Mrowietz et al, (1998) Br. J. Derm, 138:456-460.

See also Wilson et al. (2007) Nat Immunol 8 (9), 950-957; Ortega et al. (2009) J Leukoc Biol 86 (2), 435-443; Cargill et al. (2007) Am J Hum Genet 80 (2), 273-290; Nair et al. (2008) J Invest Dermatol 128 (7), 1653-1661; Krueger et al. (2007) N Engl J Med 356 (6), 580-592; Kimball et al. (2008) J Am Acad Dermatol; Segal, B. M. et al. (2008) Lancet Neurol 7 (9), 796-804; Coimbra et al. Br J Dermatol 163 (6), 1282-1290; Hueber et al. Sci Transl Med 2 (52), 52ra72; Hida et al. (2000) Immunity 13 (5), 643-655; Seckin et al. (2004) Pediatr Dermatol 21 (5), 577-579; Downs and Dunnill (2000) C. Clin Exp Dermatol 25 (4), 351-352.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) Nature Medicine, 8:295-301; Robinson et al. (2003) Nature Biotechnology, 21:1033-9; Ousman et al. (2007) Nature 448:474-479; Han et al. (2008) Nature, 451:1076-1081; and Eisen et al. (1998) Proc. Natl. Acad. Sci. Usa 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 14

Trial for Assessing Cytokine Profiles in Systemic Lupus Erythematosis (SLE)

The association of biomarkers, including biomarkers associated with Th17 cells, with development of Systemic Lupus Erythematosis (SLE) and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Merrill et al. (2010) Arth. & Rheum. 62:222-223; and Furie, et al. (2009) Arthritis & Rheumatism 61:1143-1151.

See, also Mok et al. (2010) J Rheumatol. 37(10):2046-52; Crispin and Tsokos (2010) Curr Opin Rheumatol. 22(5):499-503; Nalbandian et al. (2009) Clin Exp Immunol. 157(2):209-15; Tanasescu et al. (2010) Eur J Intern Med. 21(3):202-7.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. Usa* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 15

Trial for Assessing Cytokine Profiles in Ulcerative Colitis and Crohn's Disease

The association of biomarkers, including biomarkers associated with Th17 cells, with development of ulcerative colitis and Crohn's Disease and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Ghosh et al. N Engl J Med 2003; 348:24-32; Sandborn et al. Gastroenterology 2008; 135:1130-1141; and Rutgeerts et al. N Engl J Med 2005; 353:2462-76. See also Abraham and Cho (2009) Annu Rev Med. 60:97-110.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 16

Trial for Assessing Cytokine Profiles in Ankylosing Spondylitis

The association of biomarkers, including biomarkers associated with Th17 cells, with development of ankylosing spondylitis and response to therapies relating to Th17 is cells is determined in an appropriately powered independent cohort. It is determined whether biomarker levels, which can include IL-17A, IL-17F, and IL-23 without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Calin et al. Ann Rheum Dis 2004; 63:1594-1600. See also Mei et al. (2011) Clin. Rheumatol. 30:269-273; and Shen et al. (2009) Arthr. & Rheum. 60:1647-1656).

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 17

Trial for Assessing Cytokine Profiles in Rheumatoid Arthritis (RA)

The association of biomarkers, including biomarkers associated with Th17 cells, with development of rheumatoid arthritis and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Wang et al. (2011) Rheum. Int.; Weinblatt et al. N Engl J Med 2010; 363:1303-12; and Genovese et al. N Engl J Med 2010; 363:1303-12.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 18

Trial for Assessing Cytokine Profiles in Diabetes Mellitus Type 1 (IDDM)

The association of biomarkers, including biomarkers associated with Th17 cells, with development of IDDM and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Genovese et al. (2008) Arthritis & Rheum. 58(10): 2968-2980. See also van Sickle et al. (2009) Cytokine 48:290-294.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 19

Trial for Assessing Cytokine Profiles in Asthma

The association of biomarkers, including biomarkers associated with Th17 cells, with development of asthma and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Corren et al. (2010) Am J Respir Crit Care Med 181:788-796; and Busse et al. (2008) Am J Respir Crit Care Med 178:1002-1008. See also Nakajima et al. (2010) Immune Network 10:1.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 20

Trial for Assessing Cytokine Profiles in Chronic Obstructive Pulmonary Disorder (COPD)

The association of biomarkers, including biomarkers associated with Th17 cells, with development of COPD and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Tashkin et al. N Engl J Med 2008; 359:1543-54. See also Hong and Lee (2010) Imm. Net. 10(4):109.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 21

Trial for Assessing Cytokine Profiles in Chronic Hepatitis

The association of biomarkers, including biomarkers associated with Th17 cells, with development of chronic hepatitis and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Fried et al. (2002) N Engl J Med. 347(13): 975. See also Wu et al. Journal of Gastroenterology and Hepatology 25 (2010) 750-757; Zhang et al. (2010) Hepatology (2010) 51:81-91).

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 22

Trial for Assessing Cytokine Profiles in Amyotrophic Lateral Sclerosis (ALS)

The association of biomarkers, including biomarkers associated with Th17 cells, with development of ALS and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Aggarwal et al. (2010) *Lancet Neurol* 9: 481-88. See also Geser et al. (2010) Neuropathology 30(2):103-12; Rentzos et al. (2010) Acta Neurol Scand. 122(6):425-9.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 23

Trial for Assessing Cytokine Profiles in Alzheimer's Disease (AD)

The association of biomarkers, including biomarkers associated with Th17 cells, with development of Alzheimer's Disease and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Gold et al. (2010) Dement Geriatr Cogn Disord 30:131-146. See also Saresella ET AL. (2010) Brain Behav Immun.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 24

Trial for Assessing Cytokine Profiles in Parkinson's Disease

The association of biomarkers, including biomarkers associated with Th17 cells, with development of Parkinson's Disease and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Hauser et al. (2010) Movement Disorders 25(15): 2542-2549. See also Reynolds et al. J Immunol. 2010 Mar. 1; 184(5):2261-71.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine*, 8:295-301; Robinson et al. (2003) *Nature Biotechnology*, 21:1033-9; Ousman et al. (2007) *Nature* 448:474-479; Han et al. (2008) *Nature*, 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 25

Trial for Assessing Cytokine Profiles in Frontotemporal Lobar Degeneration (FTLD)

The association of biomarkers, including biomarkers associated with Th17 cells, with development of FTLD and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Boxer et al. (2009) Alzheimer Dis Assoc Disord. 23(3): 211-217. See also Geser et al. (2010) Neuropathology 30(2):103-12; Hu et al. (2010) Neurology.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 26

Trial for Assessing Cytokine Profiles in atherosclerosis/cardiovascular disease

The association of biomarkers, including biomarkers associated with Th17 cells, with development of atherosclerosis and cardiovascular disease and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Sever et al. (2003) Lancet 361:1149-1158.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

Example 27

Trial for Assessing Cytokine Profiles in Obesity/Metabolic Syndrome

The association of biomarkers, including biomarkers associated with Th17 cells, with development of atherosclerosis and cardiovascular disease and response to therapies relating to Th17 is cells is determined in an appropriately powered independent cohort. It is determined whether biomarker levels, which can include IL-17A, IL-17F, and IL-23, without limitation, change as therapy progresses and if treatment failures correlate with changes. Cytokines of interest for analysis also include PDGFBB, IL13 and eotaxin. Methods for assessment of patient outcomes are described previously in the instant specification; study design and analysis include the methods set forth in Hofso et al. European Journal of Endocrinology 163 735-745.

Study Oversight.

Steering-committee members develop the protocol and monitor the ongoing study. Data are collected by the investigators.

Patients.

Key eligibility criteria and key exclusion criteria are as set forth in Example 9. The study is conducted in accordance with the International Conference on Harmonisation Guidelines for Good Clinical Practice and the Declaration of Helsinki. The protocol is approved by the site's institutional review board; patients give written informed consent before any study-related procedures are performed.

Experimental Procedure.

Blood is drawn prior to institution of therapy. Every six months over the next 24 months, a patient will undergo a venipuncture to obtain serum for multiplex determination of the 28 analytes on the Luminex bead system, as described in Example 1.

Outcome Measures and Statistics.

Multiplex measurement of cytokine and chemokine markers is performed, classifying responders with Statistical Analysis of Microarrays as described in Example 1 (for additional methodology see Axtell et al., supra. Robinson et al. (2002) *Nature Medicine,* 8:295-301; Robinson et al. (2003) *Nature Biotechnology,* 21:1033-9; Ousman et al. (2007) *Nature* 448:474-479; Han et al. (2008) *Nature,* 451:1076-1081; and Eisen et al. (1998) *Proc. Natl. Acad. Sci. USA* 95, 14863-14868. The data is clustered with Tree View, as described by Axtell et al, supra. Clinical assessments are performed at screening and at randomization (baseline), and study visits, including safety assessments, are scheduled after randomization.

Power Calculations and Bioinformatic Analysis of Human Data with a 28 Analyte Array.

Statistical Analysis of Microarrays (SAM) and Prediction Analysis of Microarray (PAM) algorithms are used. Power calculations are performed using bioinformatics.mdanderson.org/MicroarraySampleSize/MicroarraySampleSize.aspx with a set of 28 genes, a false positive rate of 1, a desired fold change of 1.5 or more, with a power of 0.8 and a standard deviation of 0.9. Power and Sample Size estimates for One ROC Curve Power Analysis are as described in Example 9.

What is claimed is:

1. A method for assessing prognosis for responsiveness of a human multiple sclerosis patient to interferon beta, comprising:
    analyzing a blood sample from said patient with an antibody-based assay and detecting the quantity of IL-17F present in the sample to provide a quantitative dataset for IL-17F;
    comparing the quantity of IL-17F in the sample to a control quantity, wherein the control quantity is the quantity of IL-17F in a blood sample from a human multiple sclerosis subject that is responsive to interferon beta,
    detecting an increased the quantity of IL-17F in the sample as compared to the control quantity;
    correlating the increased quantity of IL-17F in the sample as compared to the control quantity with an assessment that the patient is a non-responder to interferon beta;
    providing to said multiple sclerosis patient an assessment of responsiveness to interferon beta, and
    administering a non-interferon beta multiple sclerosis therapeutic agent to the patient.

2. The method of claim 1, wherein the dataset further comprises quantitative data for the marker PDGFBB.

3. The method of claim 1, wherein the dataset further comprises quantitative data for the marker IL-13.

4. The method of claim 1, wherein the dataset further comprises quantitative data for the marker IL-7.

5. The method of claim 1, wherein the dataset further comprises quantitative data for at least one marker selected from the group consisting of: IL-17A, interferon beta, eotaxin, IL-12p70, RANTES, IL-1alpha, MCP3, TGFbeta, NGF, IL-5, MIP-1beta, HGF, IL-23, IL-8, and IL-6.

6. The method of claim 1, wherein the dataset further comprises quantitative data for at least one marker selected from the group consisting of: IL-7, PDGFBB, IL-13, IL-17A, interferon beta, eotaxin, IL-12p70, RANTES, IL-1alpha, MCP3, TGFbeta, NGF, IL-5, MIP-1beta, HGF, IL-23, IL-8, and IL-6.

7. A method for assessing prognosis for responsiveness of a human relapsing remitting multiple sclerosis (RRMS) patient to interferon beta, comprising:
    analyzing a blood sample from said patient with an antibody-based assay and detecting the quantity of IL-17F present in the sample to provide a quantitative dataset for IL-17F;
    comparing the quantity of IL-17F in the sample to a control quantity, wherein the control quantity is the quantity of IL-17F in a blood sample from a human RRMS subject that is responsive to interferon beta;
    detecting a quantity of IL-17F in the sample that is not increased as compared to the control quantity;
    correlating the quantity of IL-17F in the sample as compared to the control quantity with an assessment that the patient is a responder to interferon beta; and
    administering an interferon beta to the patient.

8. The method of claim 7, wherein said interferon beta is Betaseron.

9. The method of claim 7, wherein said interferon beta is Rebif.

10. The method of claim 7, wherein said interferon beta is Extavia.

11. A method for assessing prognosis for responsiveness of a human multiple sclerosis patient to interferon beta, comprising:

analyzing a blood sample from said patient with an antibody-based assay and detecting the quantity of IL-17F present in the sample to provide a quantitative dataset for IL-17F;

comparing the quantity of IL-17F in the sample to a control quantity, wherein the control quantity is the quantity of IL-17F in a blood sample from a human multiple sclerosis subject that is responsive to interferon beta, detecting an increased the quantity of IL-17F in the sample as compared to the control quantity;

correlating the increased quantity of IL-17F in the sample as compared to the control quantity with an assessment that the patient is a non-responder to interferon beta;

providing to said multiple sclerosis patient an assessment of responsiveness to interferon beta, and administering glatiramer acetate to the patient.

12. The method of claim 1, further comprising administering BG-12 to the patient.

13. The method of claim 1, further comprising administering an anti-IL-12/23 drug to the patient.

14. The method of claim 13, wherein said anti-IL-12/23 drug is ustekinumab.

15. The method of claim 13, wherein said anti-IL-12/23 drug is briakinumab.

16. The method of claim 1, wherein the multiple sclerosis is Relapsing Remitting Multiple Sclerosis.

17. The method of claim 1, wherein the multiple sclerosis is Secondary Progressive Multiple Sclerosis.

18. The method of claim 1, wherein the multiple sclerosis is Primary Progressive Multiple Sclerosis.

19. The method of claim 1, further comprising assessing a clinical factor in the patient.

* * * * *